United States Patent
Crowe et al.

(10) Patent No.: US 11,584,735 B2
(45) Date of Patent: Feb. 21, 2023

(54) SOLID FORMS OF A PLASMA KALLIKREIN INHIBITOR AND SALTS THEREOF

(71) Applicant: KALVISTA PHARMACEUTICALS LIMITED, Wiltshire (GB)

(72) Inventors: David Malcolm Crowe, Reading (GB); Edwin Aret, Weert (NL); Kiran Gandhi, Cambridge (GB); Ruben Henricus Carolus Adrianus Titus Lelieveld, Weert (NL); Emma Kay Sharp, Cambridge (GB); Richard Simon Todd, Salisbury (GB)

(73) Assignee: KalVista Pharmaceuticals Limited, Porton Down (GB)

( * ) Notice: Subject to any disclaimer, the term of this patent is extended or adjusted under 35 U.S.C. 154(b) by 0 days.

(21) Appl. No.: 16/767,717

(22) PCT Filed: Nov. 29, 2018

(86) PCT No.: PCT/GB2018/053466
§ 371 (c)(1),
(2) Date: May 28, 2020

(87) PCT Pub. No.: WO2019/106377
PCT Pub. Date: Jun. 6, 2019

(65) Prior Publication Data
US 2021/0171496 A1    Jun. 10, 2021

Related U.S. Application Data

(60) Provisional application No. 62/592,140, filed on Nov. 29, 2017.

(30) Foreign Application Priority Data

Nov. 29, 2017 (GB) ...................................... 1719881

(51) Int. Cl.
C07D 401/14    (2006.01)

(52) U.S. Cl.
CPC ........ *C07D 401/14* (2013.01); *C07B 2200/13* (2013.01)

(58) Field of Classification Search
None
See application file for complete search history.

(56) References Cited

U.S. PATENT DOCUMENTS

| 5,187,157 A | 2/1993 | Kettner et al. |
| 5,786,328 A | 7/1998 | Dennis et al. |

(Continued)

FOREIGN PATENT DOCUMENTS

| CA | 2730078 A1 | 1/2010 |
| CN | 101437577 A | 5/2009 |

(Continued)

OTHER PUBLICATIONS

Golub, et al., "Molecular Classification of Cancer: Class Discovery and Class Prediction by Gene Expression Monitoring", Science, Oct. 15, 1999, vol. 286, 531-537.

(Continued)

*Primary Examiner* — Sudhakar Katakam
*Assistant Examiner* — Jennifer C Sawyer
(74) *Attorney, Agent, or Firm* — BakerHostetler

(57) ABSTRACT

New solid forms of the plasma kallikrein inhibitor, 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide and its salts, are described.

15 Claims, 20 Drawing Sheets

(56) References Cited

U.S. PATENT DOCUMENTS

| | | |
|---|---|---|
| 7,101,878 B1 | 9/2006 | Anderson et al. |
| 8,207,378 B2 | 6/2012 | Steinmetzer et al. |
| 9,382,219 B2 | 7/2016 | Das et al. |
| 9,512,065 B2 | 12/2016 | Northen et al. |
| 9,533,987 B2 | 1/2017 | Davie et al. |
| 9,670,157 B2 | 6/2017 | Allan et al. |
| 9,738,641 B2 | 8/2017 | Edwards et al. |
| 9,834,513 B2 | 12/2017 | Allan et al. |
| 10,221,161 B2 | 3/2019 | Edwards et al. |
| 10,364,238 B2 | 7/2019 | Davie et al. |
| 10,611,758 B2 | 4/2020 | Davie et al. |
| 10,752,607 B2 | 8/2020 | Beaton et al. |
| 10,781,181 B2 | 9/2020 | Evans et al. |
| 2007/0254894 A1 | 11/2007 | Kane et al. |
| 2008/0038276 A1 | 2/2008 | Sinha et al. |
| 2008/0221091 A1 | 9/2008 | Gege et al. |
| 2009/0163545 A1 | 6/2009 | Goldfarb |
| 2010/0113782 A1 | 5/2010 | Bolin et al. |
| 2011/0152533 A1 | 6/2011 | Sinha et al. |
| 2012/0035168 A1 | 2/2012 | Brandl et al. |
| 2012/0298326 A1 | 11/2012 | Born |
| 2014/0213611 A1 | 7/2014 | Evans et al. |
| 2014/0378474 A1 | 12/2014 | Flohr et al. |
| 2015/0191421 A1 | 7/2015 | Northen et al. |
| 2015/0225450 A1 | 8/2015 | Evans et al. |
| 2015/0315198 A1 | 11/2015 | Li et al. |
| 2016/0039752 A1 | 2/2016 | Allan et al. |
| 2017/0305863 A1 | 10/2017 | Evans et al. |
| 2018/0319782 A1 | 11/2018 | Davie et al. |

FOREIGN PATENT DOCUMENTS

| | | |
|---|---|---|
| EA | 007934 B1 | 2/2007 |
| EA | 012882 B1 | 12/2009 |
| EA | 201200917 | 12/2012 |
| EA | 021359 | 5/2015 |
| EP | 1426364 A1 | 6/2004 |
| EP | 1568698 A1 | 8/2005 |
| EP | 2281885 A1 | 2/2011 |
| EP | 2807157 A1 | 12/2014 |
| EP | 3089746 A1 | 11/2016 |
| EP | 3224256 A1 | 10/2017 |
| JP | 2009-545611 A | 12/2009 |
| JP | 2010-520294 A | 6/2010 |
| JP | 2011-157349 A | 8/2011 |
| JP | 2013-532713 A | 8/2013 |
| RU | 2485114 C2 | 6/2013 |
| WO | 92/04371 A1 | 3/1992 |
| WO | 94/29335 A1 | 12/1994 |
| WO | 95/07921 A1 | 3/1995 |
| WO | 03/35076 A1 | 5/2003 |
| WO | 03/37274 A2 | 5/2003 |
| WO | 03/76458 A2 | 9/2003 |
| WO | 03/91226 A1 | 11/2003 |
| WO | 2004/062657 A1 | 7/2004 |
| WO | 2004/069792 A2 | 8/2004 |
| WO | 2005/049578 A1 | 6/2005 |
| WO | 2005/079800 A1 | 9/2005 |
| WO | 2005/123680 A1 | 12/2005 |
| WO | 2006/025714 A1 | 3/2006 |
| WO | 2006/091459 A2 | 8/2006 |
| WO | 2006/114313 A1 | 11/2006 |
| WO | 2007/001139 A1 | 1/2007 |
| WO | 2007/011626 A2 | 1/2007 |
| WO | 2007/113289 A1 | 10/2007 |
| WO | 2008/003697 A1 | 1/2008 |
| WO | 2008/016883 A2 | 2/2008 |
| WO | 2007/130842 A2 | 5/2008 |
| WO | 2008/049595 A1 | 5/2008 |
| WO | 2008/091692 A2 | 7/2008 |
| WO | 2008/119825 A2 | 10/2008 |
| WO | 2008/121670 A1 | 10/2008 |
| WO | 2009/012998 A1 | 1/2009 |
| WO | 2009/026407 A1 | 2/2009 |
| WO | 2009/083553 A1 | 7/2009 |
| WO | 2009/097141 A1 | 8/2009 |
| WO | 2009/106980 A2 | 9/2009 |
| WO | 2009/114677 A1 | 9/2009 |
| WO | 2010/142801 A1 | 12/2010 |
| WO | 2011/075684 A1 | 6/2011 |
| WO | 2011/094496 A2 | 8/2011 |
| WO | 2011/118672 A1 | 9/2011 |
| WO | 2012/004678 A1 | 1/2012 |
| WO | 2012/009009 A2 | 1/2012 |
| WO | 2012/017020 A1 | 2/2012 |
| WO | 2012/142308 A1 | 10/2012 |
| WO | 2012/174362 A1 | 12/2012 |
| WO | 2013/005045 A1 | 1/2013 |
| WO | 2013/048982 A1 | 4/2013 |
| WO | 2013/049096 A1 | 4/2013 |
| WO | 2013/111107 A1 | 8/2013 |
| WO | 2013/111108 A1 | 8/2013 |
| WO | 2013/120104 A2 | 8/2013 |
| WO | 2013/130603 A1 | 9/2013 |
| WO | 2014/006414 A1 | 1/2014 |
| WO | 2014/108406 A1 | 7/2014 |
| WO | 2014/108679 A1 | 7/2014 |
| WO | 2014/108685 A1 | 7/2014 |
| WO | 2014/113712 A1 | 7/2014 |
| WO | 2014/145986 A1 | 9/2014 |
| WO | 2014/188211 A1 | 11/2014 |
| WO | 2015/022546 A1 | 2/2015 |
| WO | 2015/022547 A1 | 2/2015 |
| WO | 2015/103317 A1 | 7/2015 |
| WO | 2015/134998 A1 | 9/2015 |
| WO | 2015/171526 A2 | 11/2015 |
| WO | 2015/171527 A1 | 11/2015 |
| WO | 2016/011209 A1 | 1/2016 |
| WO | 2016/029214 A1 | 2/2016 |
| WO | 2016/044662 A1 | 3/2016 |
| WO | 2016/083816 A1 | 6/2016 |
| WO | 2016/083818 A1 | 6/2016 |
| WO | 2016/083820 A1 | 6/2016 |
| WO | 2016/138532 A1 | 9/2016 |
| WO | 2017/001924 A1 | 1/2017 |
| WO | 2017/001926 A2 | 1/2017 |
| WO | 2017/001936 A2 | 1/2017 |
| WO | 2017/072020 A1 | 5/2017 |
| WO | 2017/072021 A1 | 5/2017 |
| WO | 2017/207983 A1 | 12/2017 |
| WO | 2017/207985 A1 | 12/2017 |
| WO | 2017/207986 A1 | 12/2017 |
| WO | 2017/207989 A1 | 12/2017 |
| WO | 2017/208002 A1 | 12/2017 |
| WO | 2017/208005 A1 | 12/2017 |
| WO | 2018/011628 A1 | 1/2018 |
| WO | 2019/030540 A1 | 2/2019 |
| WO | 2019/106359 A1 | 6/2019 |
| WO | 2019/106361 A1 | 6/2019 |
| WO | 2019/106375 A1 | 6/2019 |
| WO | 2019/106377 A1 | 6/2019 |
| WO | 2020/249977 A1 | 12/2020 |
| WO | 2020/249979 A1 | 12/2020 |
| WO | 2021/028645 A1 | 2/2021 |
| WO | 2021/028649 A1 | 2/2021 |
| WO | 2021/032933 A1 | 2/2021 |
| WO | 2021/032934 A1 | 2/2021 |
| WO | 2021/032935 A1 | 2/2021 |
| WO | 2021/032936 A1 | 2/2021 |
| WO | 2021/032937 A1 | 2/2021 |
| WO | 2021/032938 A1 | 2/2021 |
| WO | 2021/116679 A1 | 6/2021 |

OTHER PUBLICATIONS

Lala, et al., "Role of nitric oxide in tumor progression: Lessons from experimental tumors", Cancer and Metastasis Reviews, 1998, 17: 91-106.

Bryant et al., "Human Plasma Kallikrein-Kinin System: Physiological and Biochemical Parameters", Cardiovascular and Haematological Agents in Medicinal Chemistry, Jul. 2009, pp. 234-250.

Chemical Abstract Service, Chemcats, RN 1424383-07-2, Mar. 15, 2013.

(56) References Cited

OTHER PUBLICATIONS

Elman et al., "Randomized Trial Evaluating Ranibizumab Plus Prompt or Deferred Laser or Triamcinolone Plus Prompt Laser for Diabetic Macular Edema", Ophthalmology, Jun. 2010, 117(6), e35, pp. 1064-1077.
Zhang et al. "Discovery of Highly Potent Small Molecule Kallikrein Inhibitors" Medicinal Chemistry, 2006, 2, pp. 545-553.
Registry No. 956521-49-6, Chemical Library—FCG Group, Dec. 3, 2007, 1 page.
Registry No. 956529-72-9, Chemical Library—FCG Group, Dec. 3, 2007, 1 page.
Registry No. 956747-39-0, Chemical Library—FCG Group, Dec. 5, 2007, 1 page.
Remington's Pharmaceutical Sciences, 19.sup.th Edition, Gennaro, Mack Publishing Company, 1995, 5 pages.
Revenko et al.; "Selective depletion of plasma prekallikrein or coagulation factor XII inhibits thrombosis in mice without increased risk of bleeding"; Blood; Aug. 5, 2011; 118; p. 5302-5311.
Shori et al., "New Specific Assays for Tonin and Tissue Kallikrein Activities in Rat Submandibular Glands: Assays Reveal Differences in the Effects of Sympathetic and Parasympathetic Stimulation on Proteinases in Saliva", Biochemical Pharmacology, Mar. 17, 1992, 43(6), pp. 1209-1217.
Siebeck et al.; "Inhibition of Plasma Kallikrein With Aprotinin in Porcine Endotoxin Shock"; Journal of Trauma; Feb. 1993; vol. 34 No. 2; p. 193-198.
Stahl et al., "Handbook of Pharmaceutical Salts: Properties, Selection and Use", Wiley-VCH, Weinheim, Germany, 2002, 1 page.
STN Registry, "5-Pyrimidinecarboxamide, 1,6-dihydro-N-[1-(6-methyl-1 H-benzimidazol-2-yl)ethyl]-2-oxo-2-(1 H-1,2,4—triazol-1-ylmethyl)", CAS No. 1422635-37-7, Mar. 8, 2013.
STN Registry, "5-Pyrimidinecarboxamide, N-[1-(1 H-benzimidazol-2-yl)ethyl]-1,6-dihydro-6-oxo-2-(phenoxymethyl)", CAS No. 1434334-41-4, Jun. 5, 2013.
Sturzbecher et al., "Novel plasma kallikrein inhibitors of the benzamidine type", Brazilian J. med. Biol. Res., 1994, 27, 1929-1934.
Sturzebecher et al., "Inhibition of Human Mast Cell Tryptase by Benzamidine Derivatives", Biological Chemistry Hoppe-Seyler, Oct. 1992, 373(2), 1025-1030.
Tanaka et al., Thrombosis Research 2004, "Evaluation of a novel kallikrein inhibitor on hemostatic activation in vitro"; 113, 333-339.
Tang et al., "Expression, Crystallization, and Three-Dimensional Structure of the Catalytic Domain of Human Plasma Kallikrein" The Journal of Biological Chemistry vol. 280, No. 49, Dec. 2005, pp. 41077-41089.
Teno et al., "Development of Active Center-Directed Plasmin and Plasma Kallikrein Inhibitors and Studies on the Structure-Inhibitory Activity Relationship", Chem. Pharm. Bull., Jun. 1993, 41, 1079-1090.
Tombran-Tink et al., "Opthamology Research", Visual Dysfunction in Diabetes the Science of Patient Impairment and Health Care, 2012, 4 pages.
Tombran-Tink et al.; "Visual Dysfunction in Diabetes: The Science of Patient Impairment and Health Care"; Humana Press; 2012; p. 34.
Ulven et al.; "6-Acylamino-2-amino-4-methylquinolines as potent melanin-concentrating hormone 1 receptor antagonists: Structure-activity exploration of eastern and western parts"; Bioorganic & Medicinal Chemistry Letters; vol. 16 Issue 4; Feb. 2006; p. 1070-1075.
Wang et al., "Determination of In Vitro Permeability of Drug Candidates through a Caco-2 Cell Monolayer by Liquid Chromatography/Tandem Mass Spectrometry" J. Mass Spectrom 35(1); 71-76, 2000.
Wermuth et al., Handbook of Pharmaceutical Salts: Properties, Selection and Use, 2002 vol. 24, No. 3, p. 20.
Wermuth, "The Practice of Medicinal Chemistry", 2003, 2nd Ed., pp. 561-585.
Young et al., "Small Molecule Inhibitors of Plasma Kallikrein", Bioorg. Med. Chem. Letts., Apr. 2006, 16(7), pp. 2034-2036.

Ambinter Sari: "1 H-Pyrazole-4-carboxamides" In: Chemical Catalog, 11; Sep. 2011 (Sep. 11, 2011), Ambinter SARL, XP055601375.
Aulton's pharmaceutics the design and manufacture of medicines, 3rd Ed, Churchill LivingstoneElsevier, Hungary, 2007, p. 356.
Babu et al., "A Simple, Sensitive and Selective Fluorogenic Assay to Monitor Plasma Kallikrein Inhibitory Activity of BCX4161 in Activated Plasma", Journal of Allergy and Clinical Immunology, Feb. 2014, 133(2 Supp), Abstract AB40, p. 1.
Babu, "Drug Discovery at BioCryst Pharmaceuticals Inc.", Presentation, http://files.shareholder.com/downloads/BCRX/0x0x403076/97a18d6e-1621-4fc6--8f5fd0828bddab4f/, Sep. 16, 2010, 18 pages.
Baeriswyl et al., "A Synthetic Factor XIIa Inhibitor Blocks Selectively Intrinsic Coagulation Initiation", ACS Chem. Biol., 2015, 10(8), 1861-1870.
Bernstein et al., "Polymorphism in Molecular Crystals", 2002, pp. 1-8.
Bhoola et al., "Bioregulation of Kinins: Kallikreins, Kininogens and Kininases", Pharmacological Rev., Mar. 1992, 44(1), pp. 1-80.
Bhoola et al., "Kallikrein-Kinin Cascade" Encyclopedia of Respiratory Medicine, 2006, pp. 483-493.
Bird et al.; Effects of plasma kallikrein deficiency on haemostasis and thrombosis in mice: Murine Ortholog of the Fletcher Trait Thrombosis and Haemostasis; Mar. 8, 2012; vol. 107; p. 1141-1150.
Bjorkqvist et al., "Plasma kallikrein: the bradykinin-producing enzyme", Thrombosis and Haemotasis, 2013, 110, 399-407.
Bouckaert et al., "Synthesis, evaluation and structure-activity relationship of new 3-carboxamide coumarins as FXIIa inhibitors", European Journal of Medicinal Chemistry, 2016, 110, 181-194.
Brittain et al., "Polymorphism in Pharmaceutical Solids", 1999, 234-239.
Byrn et al., "Solid-State Chemistry of Drugs", 1999, 1-17, 233-247.
Caddick et al., "Convenient Synthesis of Protected Primary Amines from Nitriles", Tetrahedron Letters, Apr. 29, 2000, 41(18), 3513-3516.
Calderone et al., "1,2,3-Triazol-Carboxanilides and 1,2,3-Triazol-(N-Benzyl)-Carboxamides as BK-Potassium Channel Activators. XII" European Journal of Medicinal Chemistry 43, 2008, pp. 2618-2626.
Campbell, "Towards Understanding the Kallikrein-Kinin System: Insights from the Measurement of Kinin Peptides", Brazilian Journal of Medical and Biological Research, Jun. 2000, 33(6), 665-677.
Cannon, Chapter Nineteen in Burger's Medicinal Chemistry and Drug Discovery, Fifth Edition, vol. I: Principles and Practice, Wiley-Interscience 1995, pp. 783-802.
CAS abstract accession No. 1990:515202, corresponding to RIED et al. Liebigs Annalen der Chemie, 1990, 8, 2 pages.
CAS abstract accession No. 2013:1177162, corresponding to Ye et al. Chemical Science, 2013, 4(9), 4 pages.
CAS abstract accession No. 2013:1592386, corresponding to FR2989085 A1 (Commissariat Energie Atomique), 3 pages.
CAS abstract accession Nos. 2009:769551 and 2009:846114, corresponding to U.S. Publication 2009-0163545A1, 5 pages.
CAS extract for Compound 1180236-10-5; Sep. 4, 2009.
CAS extract for Compound 1180808-34-7; Sep. 6, 2009.
CAS Extract for Compound 1197490-19-9, dated Dec. 16, 2009, 1 page.
CAS Extract for Compound 120842-43-4, dated Apr. 18, 2011, 1 page.
CAS extract for Compound 1288265-35-9; May 1, 2011.
CAS extract for Compound 1288488-40-3; May 1, 2011.
CAS extract for Compound 1288531-53-2; May 1, 2011.
CAS extract for Compound 1293757-54-6; May 12, 2011.
CAS extract for Compound 1297493-36-7; May 19, 2011.
CAS Extract for Compound 1386962-55-5, dated Aug. 6, 2012, 1 page.
CAS Extract for Compound 1388550-15-9, dated Aug. 9, 2012, 1 page.
CAS Extract for Compound 1626023-22-0, dated Sep. 25, 2014, 1 page.
CAS Structures cited in WO201683818 Written Opinion dated Jun. 2, 2016, 290 pages.
Chemical & Engineering News, Feb. 24, 2003, pp. 32-35.

(56) References Cited

OTHER PUBLICATIONS

Chemical Abstracts Registry No. 1147797-44-1, indexed in the Registry file on STN CAS Online May 20, 2009.
Chemical Abstracts Registry No. 1217027-87-6, indexed in the Registry file on STN CAS Online Apr. 5, 2010.
Chemical Abstracts Registry No. 1241137-33-6, indexed in the Registry file on STN CAS Online Sep. 15, 2010.
Chemical Abstracts Registry No. 1295467-87-6, indexed in the Registry file on STN CAS Online May 16, 2011.
Chemical Abstracts Registry No. 1296846-83-7, indexed in the Registry file on STN CAS Online May 18, 2011.
Chemical Abstracts Registry No. 1297526-11-4, indexed in the Registry file on STN CAS Online May 19, 2011.
Chemical Abstracts Registry No. 1389653-06-8, indexed in the Registry file on STN CAS Online Aug. 12, 2012.
Chemical Abstracts Registry No. 1575116-26-5, indexed in the Registry file on STN CAS Online Mar. 28, 2014.
Chemical Abstracts Registry No. 942731-43-3, indexed in the Registry file on STN CAS Online Jul. 19, 2007.
Chilcote et al., "ASP-634: An Oral Drug Candidate for Diabetic MacularEdema", ARVO May 6-May 9, 2012, Fort Lauderdale, Florida, (Presentation 2240), 1 page.
Clermont et al., "Plasma Kallikrein Mediates Retinal Vascular Dysfunction and Induces Retinal Thickening in Diabetic Rats", Diabetes, May 2011, 60(5), pp. 1590-1598.
Collis et al., "BCX4161, An Oral Kallikrein Inhibitor: Safety and Pharmacokinetic Results of a Phase 1 Study in Healthy Volunteers", Journal of Allergy and Clinical Immunology, vol. 133, Issue 2, Supplement, Feb. 2014, p. AB39.
Colman et al.; "Plasma and tissue kallikrein in arthritis and inflammatory bowel disease" Immunopharmacology; Sep. 1999; vol. 43; p. 103-108.
Davis III et al.; "Biological activities of C1 inhibitor"; Molecular Immunology; Oct. 2008; vol. 45; p. 4057-4063.
Durairaj et al., "Prediction of Vitreal Half-Life Based on Drug Physiochemical Properties: Quantitative Structure-Pharmacokinetic Relationships (QSPKR)", Pharmaceutical Research, 2009, 26(5), 1236-1260.
Enamine website on Jul. 25, 2013 from the Internet Archive Way Back Machine {https://web.archive.org/web/20130725053127/http://www.enamine.net/index.php?option=com_content&task=view&id=22.
Evans et al., "Selective Inhibitors of Plasma Kallikrein", Immunopharmacology, May 1996, 32(1-3), pp. 115-116.
Feener et al.; "Role of plasma kallikrein in diabetes and metabolism"; Thrombosis and Haemostasis; Sep. 2013; vol. 110(3); p. 434-441.
Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), 60-71.
Greisbacher et al.; "Involvement of tissue kallikrein but not plasma kallikrein in the development of symptoms mediated by endogenous kinins in acute pancreatitis in rats"; British Journal of Pharmacology; Nov. 2002; vol. 137(5); p. 692-700.
Hilfiker et al., "Polymorphism: In the Pharmaceutical Industry", 2006, 1-19.
Ikeda et al.; "Host Stromal Bradykinin B2 Receptor Signaling Facilities Tumor-Associated Angiogenesis and Tumor Growth"; Cancer Research; Aug. 2004; vol. 64; p. 5178-5185.
International Patent Application No. PCT/GB2015/053613: International Search Report dated Jun. 2, 2016, 5 pages.
International Patent Application No. PCT/GB2015/053613: Written Opinion dated Jun. 2, 2016, 9 pages.
International Search Report for PCT/GB2014/051592 completed Jul. 23, 2014.
Jaffa et al., "Plasma Prekallikrein a Risk Marker for Hypertension and Nephropathy in Type 1 Diabetes", Diabetes, May 2003, vol. 52, 1215-1221.
Jaffa et al.; "A Risk Marker for Hypertension and Nephropathy in Type 1 Diabetes"; Diabetes; May 2003; vol. 52; p. 1215-1221.
Johansen et al., "Assay of Kallikrein Inhibitors and Levels of Acetone-Activated Kallikrein in Plasma Specimens From Reactors to Dextran or to Contrast Media", Bioscience Ed, Int J. Tiss. Reac., 1986, 185-192.
Katsuura et al., "Effects of a Highly Selective Synthetic Inhibitor of Plasma Kallikrein on Disseminated Intravascular Coagulation in Rats", Thrombosis Research, 1996, vol. 82, No. 4, 361-368.
Kenniston, J Bio Chem, "Inhibition of Plasma Kallikrein by a Highly Specific Active Site Blocking Antibody", vol. 289 (34), 2014, 23596-23608.
Kolte et al., "Biochemical Characterization of a Novel High-Affinity and Specific Kallikrein Inhibitor", British Journal of Pharmacology, Apr. 2011, 162(7), pp. 1639-1649.
Lehmann, "Ecallantide (DX-88), a Plasma Kallikrein Inhibitor for the Treatment of Hereditary Angioedema and the Prevention of Blood Loss in on-Pump Cardiothoracic Surgery", Expert Opinion Biol. Ther., Jul. 2008, 8(8), pp. 1187-1199.
Leinweber et al, "Possible Physiological Roles of Carboxylic Ester Hydrolases", Drug Metabolism Reviews, Jan. 1987, 18(4), pp. 379-439.
Liang et al., "Fast Dissolving Intraoral Drug Delivery Systems", Expert Opinion in Therapeutic Patents, Jun. 2001, 11(6), 981-986.
Lieberman et al. Pharmaceutical Dosage Forms: Tablets, Second Edition, vol. 2, 1989, XP008099925; 15 pages (front page and list of contents included), 145-157.
Lieberman et al., Pharmaceutical Dosage Forms: Tablets, vol. 1, 1980, pp. 145-157.
Liu et al.; "Hyperglycemia Induced Cerebral Hematoma Expansion is Mediated by Plasma Kallikrein"; Nat. Med.; Feb. 2011; vol. 17(2); p. 206-210.
Lussis et al.; "A single synthetic small molecule that generates force against a load"; Nature Nanotechnology; vol. 6; 2011; p. 553-557.
Lussis et al.; "A single synthetic small molecule that generates force against a load"; Nature Nanotechnology; vol. 6; 2011; p. S1-525 (Supplemental Information).
Luthin et al., "The Discovery of Novel Small Molecule Non-peptide Gonadotropin Releasing Hormone (GnRH) Receptor Antagonists" Bioorg Med Chem Lett, 12, 2002, pp. 3467-3470.
Marceau et al., "Bradykinin receptor ligands: therapeutic perspectives", Nature Review, Drug Discovery 2004, Oct. 2004, vol. 3, 845-852.
Marra et al, "Solution Formulation Development of a VEGF Inhibitor for Intravitreal Injection", 2011, 12(1), 362-370.
Maurice, "Review: Practical Issues in Intravitreal Drug Delivery", Journal of Ocular Pharmacology and Therapeutics, 2001, 17(4), 393-401.
MedicineNet (2004) Web:<http://www.medterms.com>.
Obach, "Prediction of human clearance of twenty-nine drugs from hepatic microsomal intrinsicclearance data: An examination of in vitro half-life approach and nonspecific binding tomicrosomes", Drug Metabolism and Disposition, 1999, 27(11), 1350-13592.
Okada et al., "Development of Potent and Selective Plasmin and Plasma Kallikrein Inhibitors and Studies on the Structure-Activity Relationship", Chem. Pharm. Bull., Sep. 2000, 48, pp. 1964-1972.
Pace, et al., "4-Hydroxy-5-pynolinone-3-carboxamide HIV-1 integrase inhibitors", Bioorganic & Medicinal Chemistry Letters., 18, Jun. 2008, pp. 3865-3869.
Patel, "Combination Therapy for Age-Related Macular Degeneration", Retina, Jun. 2009, 29(6), S45-S48.
Prassas, "Unleashing the therapeutic potential of human kallikrein-relatedserine proteases", Nature Reviews Drug Discovery, vol. 14, 183-202, 2015.
PubChem Compound 40150888 May 30, 2009.
PubChem Compound 51143945 May 3, 2011.
PubChem Compound 52011740 May 20, 2011.
PubChem Compound 52011741 May 20, 2001.
PubChem Compound 52011742 May 20, 2011.
PubChem Compound 52011935 May 20, 2011.
PubChem Compound 52011936 May 20, 2011.
PubChem Compound 52011937 May 20, 2011.
PubChem Compound 52011938 May 20, 2011.

(56) References Cited

OTHER PUBLICATIONS

PubChem Compound 55389827 Jan. 25, 2012.
PubChem Compound 55408484 Jan. 25, 2012.
PubChem Compound 55408530 Jan. 25, 2012.
PubChem Compound 55408677 Jan. 25, 2012.
PubChem Compound 55408742 Jan. 25, 2012.
PubChem Compound 55408894 Jan. 25, 2012.
PubChem Compound 55438190 Jan. 25, 2012.
PubChem Compound 55494217 Jan. 25, 2012.
PubChem Compound 55650494 Jan. 25, 2012.
PubChem Compound 60376550 Oct. 18, 2012.
PubChem Compound ID 22830339 Dec. 5, 2007.
PubChem Compound ID 24488625 Feb. 29, 2008.
PubChem Compound ID 38284485 May 29, 2009.
PubChem Compound ID 38284487 May 29, 2009.
PubChem Compound ID 46438580 Jul. 23, 2010.
Registry No. 1015534-45-8, Chemical Library—FCG Group, Apr. 18, 2008, 1 page.
Registry No. 1027627-81-1, Chemical Library—FCG Group, Jun. 12, 2008, 1 page.
Registry No. 1028093-96-0, Chemical Library—FCG Group, Jun. 13, 2008, 1 page.
Registry No. 1028094-50-9, Chemical Library—FCG Group, Jun. 13, 2008, 1 page.
Registry No. 1028096-34-5, Chemical Library—FCG Group, Jun. 13, 2008, 1 page.
Registry No. 1028361-95-6, Chemical Library—FCG Group, Jun. 16, 2008, 1 page.
Registry No. 1061709-51-0, Chemical Library—FCG Group, Oct. 15, 2008, 1 page.
Registry No. 1062408-24-5, Chemical Library—FCG Group, Oct. 17, 2008, 1 page.
Registry No. 1086603-37-3, Chemical Library—AKos Consulting and Solutions GmbH, CHEMCATS, dated Dec. 18, 2008, 1 page.
Registry No. 1086603-42-0, Chemical Library—AKos Consulting and Solutions GmbH, CHEMCATS, dated Dec. 18, 2008, 1 page.
Registry No. 1086603-52-2, Chemical Library—AKos Consulting and Solutions GmbH, CHEMCATS, dated Dec. 18, 2008, 1 page.
Registry No. 1094996-93-6, Chemical Library—AKos Consulting and Solutions GmbH, CHEMCATS, dated Jan. 22, 2009, 1 page.
Registry No. 1103271-51-7, Chemical Library—FCG Group, Feb. 9, 2009, 1 page.
Registry No. 1170030-40-6, Chemical Library—FCG Group, Jul. 29, 2009, 1 page.
Registry No. 1171669-07-0, Chemical Library—FCG Group, Aug. 2, 2009, 1 page.
Registry No. 1171693-25-6, Chemical Library—Ambinter, CHEMCATS, dated Aug. 2, 2017, 1 page.
Registry No. 1278351-92-0, Chemical Library—FCG Group, Apr. 11, 2011, 1 page.
Registry No. 1280842-43-4, Chemical Library—FCG Group, Apr. 18, 2011, 1 page.
Registry No. 1317328-27-0, Chemical Library—FCG Group, Aug. 14, 2011, 1 page.
Registry No. 1317855-54-1, Chemical Library—FCG Group, Aug. 15, 2011, 1 page.
Registry No. 1318167-86-0, Chemical Library—FCH Group, CHEMCATS, dated Aug. 15, 2011, 1 page.
Registry No. 1318604-27-1, Chemical Library—FCG Group, Aug. 16, 2011, 1 page.
Registry No. 1320653-15-3, Chemical Library—FCG Group, Aug. 21, 2011, 1 page.
Registry No. 1321195-15-6, Chemical Library—FCG Group, Aug. 21, 2011, 1 page.
Registry No. 1321521-84-9, Chemical Library—FCG Group, Aug. 12, 2011, 1 page.
Registry No. 1386189-59-8, Chemical Library—Ukrorgsyntez Ltd., CHEMCATS, dated Aug. 3, 2012, 1 page.
Registry No. 1390613-03-2, Chemical Library—FCG Group, Aug. 13, 2012, 1 page.
Registry No. 1569406-35-4, Chemical Library—FCG Group, Mar. 18, 2014, 1 page.
Registry No. 1570266-44-2, Chemical Library—FCG Group, Mar. 19, 2014, 1 page.
Registry No. 1572436-72-6, Chemical Library—FCG Group, Mar. 24, 2014, 1 page.
Registry No. 1572946-10-1, Chemical Library—FCG Group, Mar. 25, 2014, 1 page.
Registry No. 1573976-69-8, Chemical Library—FCG Group, Mar. 26, 2014, 1 page.
Registry No. 1575214-30-0, Chemical Library—FCG Group, Mar. 28, 2014, 1 page.
Registry No. 1580327-09-8, Chemical Library—FCH Group, Apr. 4, 2014, 1 page.
Registry No. 1625594-62-8, Chemical Library—FCG Group, Sep. 24, 2014, 1 page.
Registry No. 879195-72-9, Chemical Library—FCG Group, Apr. 4, 2006, 1 page.
Registry No. 879300-81-9, Chemical Library—FCG Group, Apr. 5, 2006, 1 page.
Registry No. 955867-36-4, Chemical Library—FCG Group, Nov. 23, 2007, 1 page.
Registry No. 955899-78-2, Chemical Library—FCG Group, Nov. 25, 2007, 1 page.
Registry No. 956190-38-8, Chemical Library—FCG Group, Nov. 28, 2007, 1 page.
Registry No. 956290-77-0, Chemical Library—FCG Group, Nov. 29, 2007, 1 page.
Registry No. 956444-80-7, Chemical Library—FCG Group, Dec. 2, 2007, 1 page.
DeNinno, M. P. et al., "1,5-Substituted nipecotic amides: Selective PDE8 inhibitors displaying diastereomer-dependent microsomal stability", Bioorganic & Medicinal Chemistry Letters, 2011, vol. 21, 3095-3098.
Registry No. 1572751-33-7, Chemical Library—FCH Group, dated Mar. 24, 2014.
Rodriguez-Spong, et al: General principles of pharmaceutical solid polymorphism: a supramolecular perspective; 56, 2004, 241-274.
Bastin et al., "Salt Selection and Optimisation Procedures for Pharmaceutical New Chemical Entities", Organic Process Research & Development, vol. 4, No. 5, Jul. 19, 2000, pp. 427-435.
Bernstein, "Polymorphism of Molecular Crystals," New York: Oxford Univ. Press, 2007, Chapter 7.3.2:, Bioavailability, pp. 324-330.
Kummerer, "Pharmaceuticals in the environment," Annual Review Of Environment and Resources, 2010, vol. 35, pp. 57-75.
Kuznetsova, Methodical Instructions, Irkutsk State University (GOUVPOIGU), General Physics Department, 2005.
Mashkovsky, Medicaments: A Guide for Doctors, Moscow, 2005, vol. 1, pp. 10-11.
Balbach et al. "Pharmaceutical evaluation of early development candidates "the 100 mg-approach"." International Journal of Pharmaceutics, 2004, 275 (1-2), pp. 1-12.
Singhal et al., "Drug polymorphism and dosage form design: a practical perspective", Advanced Drug Delivery Reviews, 2004, 56, pp. 335-347.
Caira M R, "Crystalline Polymorphism of Organic Compounds", Topics in Current Chemistry, Springer, Berlin, DE, (19980101), vol. 198, ISSN 0340-1022, pp. 163-208.
Clinical Pharmacokinetics: Theoretical, Applied, and Analytical Aspects: A Guide, Ed. by V.G. Kukes (Chapter 11.2: Relationship of the Crystal Structure of the Substance and the Pharmacokinetics and Efficiency of the Medicine, by I.G. Smirnova and V.V.), 432, 2009, 235-248.
Morisette et al., "High-through put crystallization: polymorphs, salts, co-crystals and solvates of pharmaceutical solids", Advanced drug delivery reviews, 2004, v.56, pp. 275-300 (section 1).
Promyshlennaya tekhnologiya lekarstv, Ed. by Prof. V.I. Chueshov, Kharkiv: National Pharmaceutical University Press (NFaU), 2002, vol. 2, Chapter 16.1-16.5, pp. 393-406.
Cicardi, DX-88 a recombinant inhibitor of human plasma kallikrein. Efficacy and safety in hereditary and acquired angioedema, Abstracts/Molecular Immunology, 40, 2003, pp. 197-198, Abstract 55.

(56) References Cited

OTHER PUBLICATIONS

Clermont, et al: IOVS, Plasma Kallikrein Mediates Vascular Endothelial Growth Factor—Induced Retinal Dysfunction and Thickening, May 2016, vol. 57, No. 6, 2391-2399.
Patel, et al: Allery and Asthma Proceedings; Ecallantide for treatment of acute attacks of acquired C1 esterase inhibitor deficiency; Jan.-Feb. 2013, vol. 34, No. 1, 72-77.
van den Elzen, et al: Clinic Rev Allerg Immunol; Efficacy of Treatment of Non-hereditary Angioedema; 2018, 54, 412-431.
Variankaval et al., "From Form to Function: Crystallization of Active Pharmaceutical Ingredients", AIChE Journal, 2008, vol. 54, No. 7, pp. 1682-1688.

SOLID FORMS OF A PLASMA KALLIKREIN INHIBITOR AND SALTS THEREOF

CROSS-REFERENCE TO RELATED APPLICATIONS

This application is the National Stage of International Patent Application No. PCT/GB2018/053466 filed Nov. 29, 2018, which claims priority from U.S. Patent Application No. 62/592,140 filed Nov. 29, 2017 and Great Britain Patent Application No. 1719881.3 filed Nov. 29, 2017, the disclosures of each of which are incorporated herein by reference in their entireties for any and all purposes.

The present invention relates to new solid forms of a plasma kallikrein inhibitor, a pharmaceutical composition containing them and their use in therapy. Also provided are processes for preparing the solid forms of the present invention.

BACKGROUND TO THE INVENTION

Inhibitors of plasma kallikrein have a number of therapeutic applications, particularly in the treatment of retinal vascular permeability associated with diabetic retinopathy, diabetic macular edema and hereditary angioedema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Plasma kallikrein also plays a role in blood coagulation. The intrinsic coagulation cascade may be activated by factor XII (FXII). Once FXII is activated (to FXIIa), FXIIa triggers fibrin formation through the activation of factor XI (FXI) thus resulting in blood coagulation. Plasma kallikrein is a key component in the intrinsic coagulation cascade because it activates FXII to FXIIa, thus resulting in the activation of the intrinsic coagulation pathway. Furthermore, FXIIa also activates further plasma prekallikrein resulting in plasma kallikrein. This results in positive feedback amplification of the plasma kallikrein system and the intrinsic coagulation pathway (Tanaka et al. (*Thrombosis Research* 2004, 113, 333-339); Bird et al. (*Thrombosis and Haemostasis*, 2012, 107, 1141-50).

Contact of FXII in the blood with negatively charged surfaces (such as the surfaces of external pipes or the membrane of the oxygenator that the blood passes during cardiopulmonary bypass surgery) induces a conformational change in zymogen FXII resulting in a small amount of active FXII (FXIIa). The formation of FXIIa triggers the formation of plasma kallikrein resulting in blood coagulation, as described above. Activation of FXII to FXIIa can also occur in the body by contact with negatively charged surfaces on various sources (e.g. bacteria during sepsis, RNA from degrading cells), thus resulting in disseminated intravascular coagulation (Tanaka et al. (*Thrombosis Research* 2004, 113, 333-339)).

Therefore, inhibition of plasma kallikrein would inhibit the blood coagulation cascade described above, and so would be useful in the treatment of disseminated intravascular coagulation and blood coagulation during cardiopulmonary bypass surgery where blood coagulation is not desired. For example, Katsuura et al. (*Thrombosis Research*, 1996, 82, 361-368) showed that administration of a plasma kallikrein inhibitor, PKSI-527, for LPS-induced disseminated intravascular coagulation significantly suppressed the decrease in platelet count and fibrinogen level as well as the increase in FDP level which usually occur in disseminated intravascular coagulation. Bird et al. (*Thrombosis and Haemostasis*, 2012, 107, 1141-50) showed that clotting time increased, and thrombosis was significantly reduced in plasma kallikrein-deficient mice. Revenko et al. (*Blood*, 2011, 118, 5302-5311) showed that the reduction of plasma prekallikrein levels in mice using antisense oligonucleotide treatment resulted in antithrombotic effects. Tanaka et al. (*Thrombosis Research* 2004, 113, 333-339) showed that contacting blood with DX-88 (a plasma kallikrein inhibitor) resulted in an increase in activated clotting time (ACT). Lehmann et al. (*Expert Opin. Biol. Ther.* 2008, 1187-99) showed that Ecallantide (a plasma kallikrein inhibitor) was found to delay contact activated induced coagulation. Lehmann et al. conclude that Ecallantide "had in vitro anticoagulant effects as it inhibited the intrinsic pathway of coagulation by inhibiting plasma kallikrein".

Plasma kallikrein also plays a role in the inhibition of platelet activation, and therefore the cessation of bleeding. Platelet activation is one of the earliest steps in hemostasis, which leads to platelet plug formation and the rapid cessation of bleeding following damage to blood vessels. At the site of vascular injury, the interaction between the exposed collagen and platelets is critical for the retention and activation of platelets, and the subsequent cessation of bleeding. Once activated, plasma kallikrein binds to collagen and thereby interferes with collagen-mediated activation of platelets mediated by GPVI receptors (Liu et al. (*Nat Med.*, 2011, 17, 206-210)). As discussed above, plasma kallikrein inhibitors reduce plasma prekallikrein activation by inhibiting plasma kallikrein-mediated activation of factor XII and thereby reducing the positive feedback amplification of the kallikrein system by the contact activation system.

Therefore, inhibition of plasma kallikrein reduces the binding of plasma kallikrein to collagen, thus reducing the interference of plasma kallikrein in the cessation of bleeding. Therefore plasma kallikrein inhibitors would be useful in the treatment of treating cerebral haemorrhage and bleeding from post operative surgery. For example, Liu et al. (*Nat Med.*, 2011, 17, 206-210) demonstrated that systemic administration of a small molecule PK inhibitor, ASP-440, reduced hematoma expansion in rats. Cerebral hematoma may occur following intracerebral haemorrhage and is caused by bleeding from blood vessels into the surrounding brain tissue as a result of vascular injury. Bleeding in the cerebral haemorrhage model reported by Liu et al. was induced by surgical intervention involving an incision in the brain parenchyma that damaged blood vessels. These data demonstrate that plasma kallikrein inhibition reduced bleeding and hematoma volume from post operative surgery. Björkqvist et al. (*Thrombosis and Haemostasis*, 2013, 110, 399-407) demonstrated that aprotinin (a protein that inhibits serine proteases including plasma kallikrein) may be used to decrease postoperative bleeding.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . " J. Peptide Res. 52, p 62-71 (1998)), T. Griesbacher et al. ("Involvement of tissue kallikrein but not plasma kallikrein in the development of symptoms mediated by endogenous kinins in acute pancreatitis in rats" British Journal of Pharmacology 137, p 692-700 (2002)), Evans ("Selective dipeptide inhibitors of kallikrein" WO03/076458), Szelke et al. ("Kininogenase inhibitors" WO92/04371), D. M. Evans et al. (Immunolpharmacology, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Sturzbecher et al. (Brazilian J. Med. Biol. Res 27, p 1929-34 (1994)), Kettner et al. (U.S. Pat. No. 5,187,157), N. Teno et al. (Chem. Pharm. Bull. 41, p 1079-1090 (1993)), W. B. Young et al. ("Small molecule inhibitors of plasma kallikrein" Bioorg. Med. Chem. Letts. 16, p 2034-2036 (2006)), Okada et al. ("Development of potent and selective plasmin and plasma kallikrein inhibitors and studies on the structure-activity relationship" Chem. Pharm. Bull. 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" Medicinal Chemistry 2, p 545-553 (2006)), Sinha et al. ("Inhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, the only selective plasma kallikrein inhibitor approved for medical use is Ecallantide. Ecallantide is formulated as a solution for injection. It is a large protein plasma kallikrein inhibitor that presents a risk of anaphylactic reactions. Other plasma kallikrein inhibitors known in the art are generally small molecules, some of which include highly polar and ionisable functional groups, such as guanidines or amidines. Recently, plasma kallikrein inhibitors that do not feature guanidine or amidine functionalities have been reported. For example Brandl et al. ("N-((6-aminopyridin-3-yl)methyl)-heteroaryl-carboxamides as inhibitors of plasma kallikrein" WO2012/017020), Evans et al. ("Benzylamine derivatives as inhibitors of plasma kallikrein" WO2013/005045), Allan et al. ("Benzylamine derivatives" WO2014/108679), Davie et al. ("Heterocyclic derivates" WO2014/188211), and Davie et al. ("N-((het)arylmethyl)-heteroaryl-carboxamides compounds as plasma kallikrein inhibitors" WO2016/083820).

In the manufacture of pharmaceutical formulations, it is important that the active compound be in a form in which it can be conveniently handled and processed in order to obtain a commercially viable manufacturing process. Accordingly, the chemical stability and the physical stability of the active compound are important factors. The active compound, and formulations containing it, must be capable of being effectively stored over appreciable periods of time, without exhibiting any significant change in the physico-chemical characteristics (e.g. chemical composition, density, hygroscopicity and solubility) of the active compound.

It is known that manufacturing a particular solid-state form of a pharmaceutical ingredient can affect many aspects of its solid state properties and offer advantages in aspects of solubility, dissolution rate, chemical stability, mechanical properties, technical feasibility, processability, pharmacokinetics and bioavailability. Some of these are described in "Handbook of Pharmaceutical Salts; Properties, Selection and Use", P. Heinrich Stahl, Camille G. Wermuth (Eds.) (Verlag Helvetica Chimica Acta, Zurich). Methods of manufacturing solid-state forms are also described in "Practical Process Research and Development", Neal G. Anderson (Academic Press, San Diego) and "Polymorphism: In the Pharmaceutical Industry", Rolf Hilfiker (Ed) (Wiley VCH). Polymorphism in pharmaceutical crystals is described in Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

The applicant has developed a novel series of compounds that are inhibitors of plasma kallikrein, which are disclosed in PCT/GB2017/051546 (published as WO2017/207983). These compounds demonstrate good selectivity for plasma kallikrein and are potentially useful in the treatment of diabetic retinopathy, macular edema and hereditary angioedema. One such compound is 1-({4-[(5-fluoro-2-oxopyridin-1-yl)methyl]phenyl}methyl)-N-[(3-fluoro-4- methoxypyridin-2-yl)methyl]-3-(methoxymethyl)pyrazole-4-carboxamide (Example 30 of PCT/GB2017/051546 (WO2017/207983)).

The name 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide denotes the structure depicted in Formula A.

Formula A

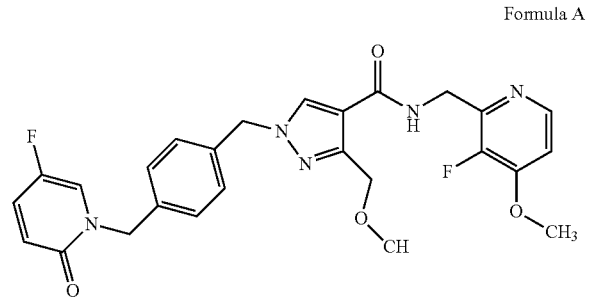 [SMILES: COCc1nn(Cc2ccc(Cn3cc(F)ccc3=O)cc2)cc1C(=O)NCc1nccc(OC)c1F]

DESCRIPTION OF THE INVENTION

Figure 1:
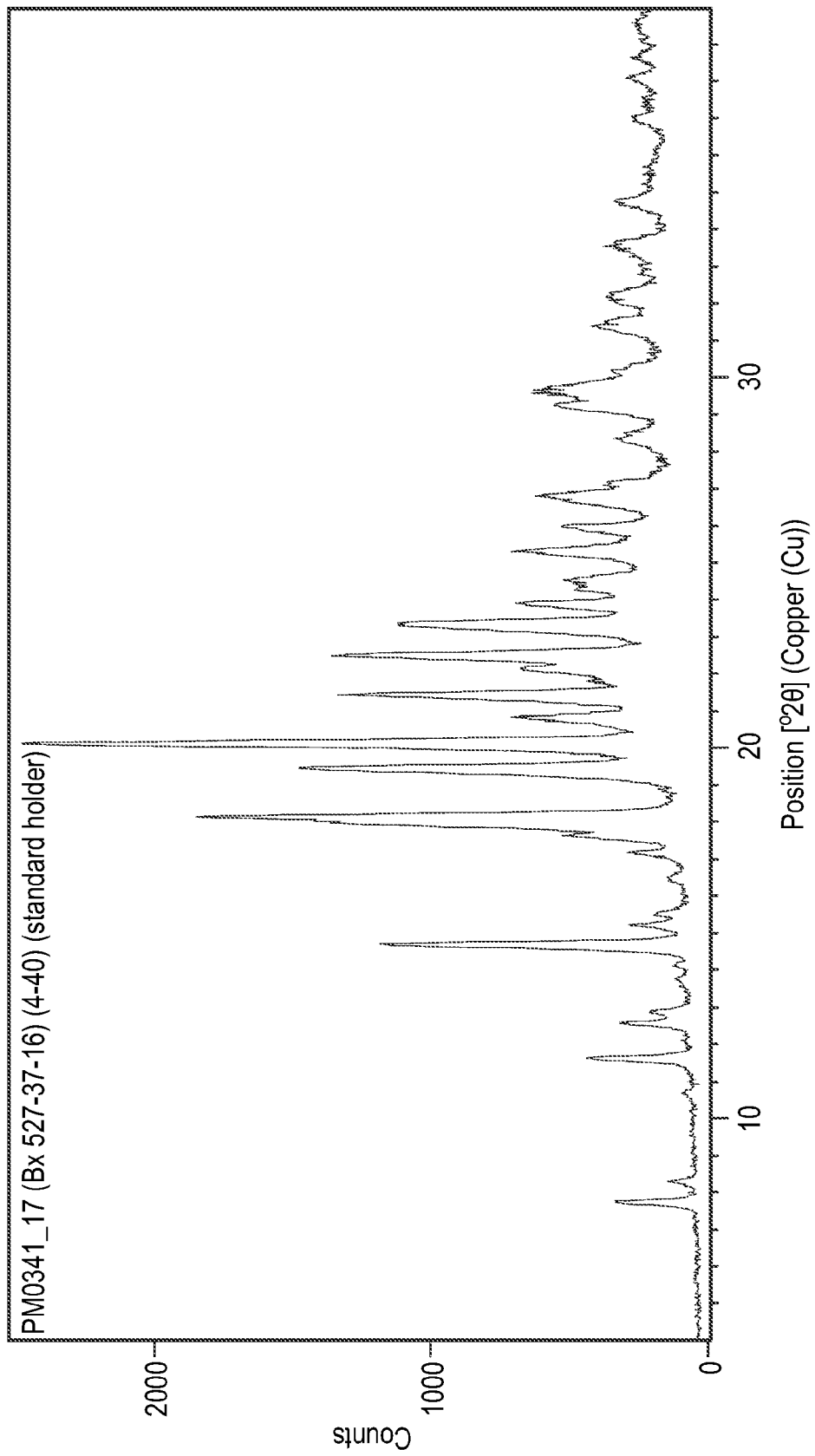
FIG. 1: X-ray powder diffraction pattern of Form 1 of the compound of Formula A (Example 1).

The applicant has now developed five novel solid forms of the compound of Formula A, which are herein referred to as 'Form 1', 'Form 2', 'Form 3', 'Form 4' and 'Form 14'. The novel solid forms have advantageous physico-chemical properties that render them suitable for development, in particular, their preparation by crystallisation is simple and scalable. An advantage of crystalline solid forms is that they are more easily processable. That is, their preparation by crystallisation is a common and easily scalable procedure to remove undesirable impurities.

Furthermore, the compound of Formula A has been found to demonstrate surprisingly good pharmacokinetic properties, in particular, in vitro permeability and metabolic stability in vitro.

Thus, in accordance with an aspect of the present invention, there are provided solid forms of the compound of Formula A. In the present application these solid forms are referred to as 'Form 1', 'Form 2', 'Form 3', 'Form 4' and 'Form 14'. Preferably, the solid form of the compound of Formula A is Form 1. Alternatively, preferably the solid form of the compound of Formula A is Form 14.

The solubility of the free base in water of the compound of Formula A was relatively low (0.29 mg/mL), and therefore salts of the compound of Formula A were investigated.

The applicant has also developed novel solid forms of salts of the compound of Formula A, specifically hydrochloride, sulfate, phosphate, mesylate, tosylate, edisylate and besylate salts of the compound of Formula A. The novel solid forms have advantageous physico-chemical properties that render them suitable for development, in particular, their preparation by crystallisation is simple and scalable.

The present invention provides specific solid forms of the hydrochloride salt of the compound of Formula A which are herein referred to as 'Form 5' and 'Form 6' and 'Form 15'. Preferably the hydrochloride salt of the compound of Formula A is Form 5. Alternatively, preferably the hydrochloride salt of the compound of Formula A is Form 15.

The present invention provides a specific solid form of the sulfate salt of the compound of Formula A which is herein referred to as 'Form 7'.

The term "sulfate" as used herein when referring to a salt of the compound of Formula A is intended to encompass both a mono-sulfate salt and a hemi-sulfate salt. In one embodiment, Form 7 of the compound of Formula A is a mono-sulfate salt. In an alternative embodiment, Form 7 of the compound of Formula A is a hemi-sulfate salt.

The present invention provides a specific solid form of the phosphate salt of the compound of Formula A which is herein referred to as 'Form 8'.

The term "phosphate" as used herein when referring to a salt of the compound of Formula A is intended to encompass both a mono-phosphate salt and a hemi-phosphate salt. In one embodiment, Form 8 of the compound of Formula A is a mono-phosphate salt. In an alternative embodiment, Form 8 of the compound of Formula A is a hemi-phosphate salt.

The present invention provides specific solid forms of the mesylate salt of the compound of Formula A which are herein referred to as 'Form 9', and 'Form 10'.

The present invention provides a specific solid form of the tosylate salt of the compound of Formula A which is herein referred to as 'Form 11'.

The present invention provides a specific solid form of the edisylate salt of the compound of Formula A which is herein referred to as 'Form 12'.

The term "edisylate" as used herein when referring to a salt of the compound of Formula A is intended to encompass both a mono-edisylate salt and a hemi-edisylate salt. In one embodiment, Form 12 of the compound of Formula A is a mono-edisylate salt. In an alternative embodiment, Form 12 of the compound of Formula A is a hemi-edisylate salt.

The present invention provides a specific solid form of the besylate salt of the compound of Formula A which is herein referred to as 'Form 13'.

The novel crystalline salts of the present invention have advantageous physico-chemical properties that render them suitable for development. For example, the sulfate and besylate salts of the compound of Formula A show a low tendency for polymorphism, as demonstrated by the single solid forms that were identified during the polymorph screens disclosed herein.

The term "solid forms" described herein includes crystalline forms. Optionally, the solid forms of the invention are crystalline forms.

In the present specification, X-ray powder diffraction peaks (expressed in degrees 2θ) are measured using Cu Kα radiation.

The present invention provides a solid form (Form 1) of the compound of Formula A, which exhibits at least the following characteristic X-ray powder diffraction peaks (Cu Kα radiation, expressed in degrees 2θ) at approximately:
(1) 11.6, 14.7, 18.1, 20.1, and 21.4; or
(2) 7.7, 11.6, 14.7, 18.1, 19.4, 20.1, and 21.4; or
(3) 7.7, 11.6, 14.7, 18.1, 19.4, 20.1, 21.4, 22.5, and 23.4.

The term "approximately" means in this context that there is an uncertainty in the measurements of the degrees 2θ of ±0.3 (expressed in degrees 2θ), preferably ±0.2 (expressed in degrees 2θ).

The present invention also provides a solid form (Form 1) of the compound of Formula A, having an X ray powder diffraction pattern comprising characteristic peaks (expressed in degrees 2θ) at approximately 7.7, 11.6, 12.6, 12.8, 14.7, 18.1, 19.4, 20.1, 21.4, 22.5, and 23.4.

The present invention also provides a solid form (Form 1) of the compound of Formula A having an X-ray powder diffraction pattern substantially the same as that shown in FIG. 1.

The X-ray powder diffraction pattern of a solid form may be described herein as "substantially" the same as that depicted in a Figure. It will be appreciated that the peaks in X-ray powder diffraction patterns may be slightly shifted in their positions and relative intensities due to various factors known to the skilled person. For example, shifts in peak positions or the relative intensities of the peaks of a pattern can occur because of the equipment used, method of sample preparation, preferred packing and orientations, the radiation source, and method and length of data collection. However, the skilled person will be able to compare the X-ray powder diffraction patterns shown in the figures herein with those of an unknown solid form to confirm the identity of the solid form.

The present invention provides a solid form (Form 2) of the compound of Formula A, which exhibits at least the following characteristic X-ray powder diffraction peaks (Cu Kα radiation, expressed in degrees 2θ) at approximately:
(1) 5.7, 9.9, 13.0, 15.0, and 17.2; or
(2) 5.7, 9.9, 13.0, 15.0, 16.0, 17.2, and 19.6; or
(3) 5.7, 9.9, 13.0, 15.0, 16.0, 17.2, 18.6, 19.6, and 22.2.

The present invention also provides a solid form (Form 2) of the compound of Formula A, having an X ray powder diffraction pattern comprising characteristic peaks (expressed in degrees 2θ) at approximately 5.7, 9.9, 13.0, 15.0, 16.0, 17.2, 17.7, 18.6, 19.6, and 22.2.

Figure 3:
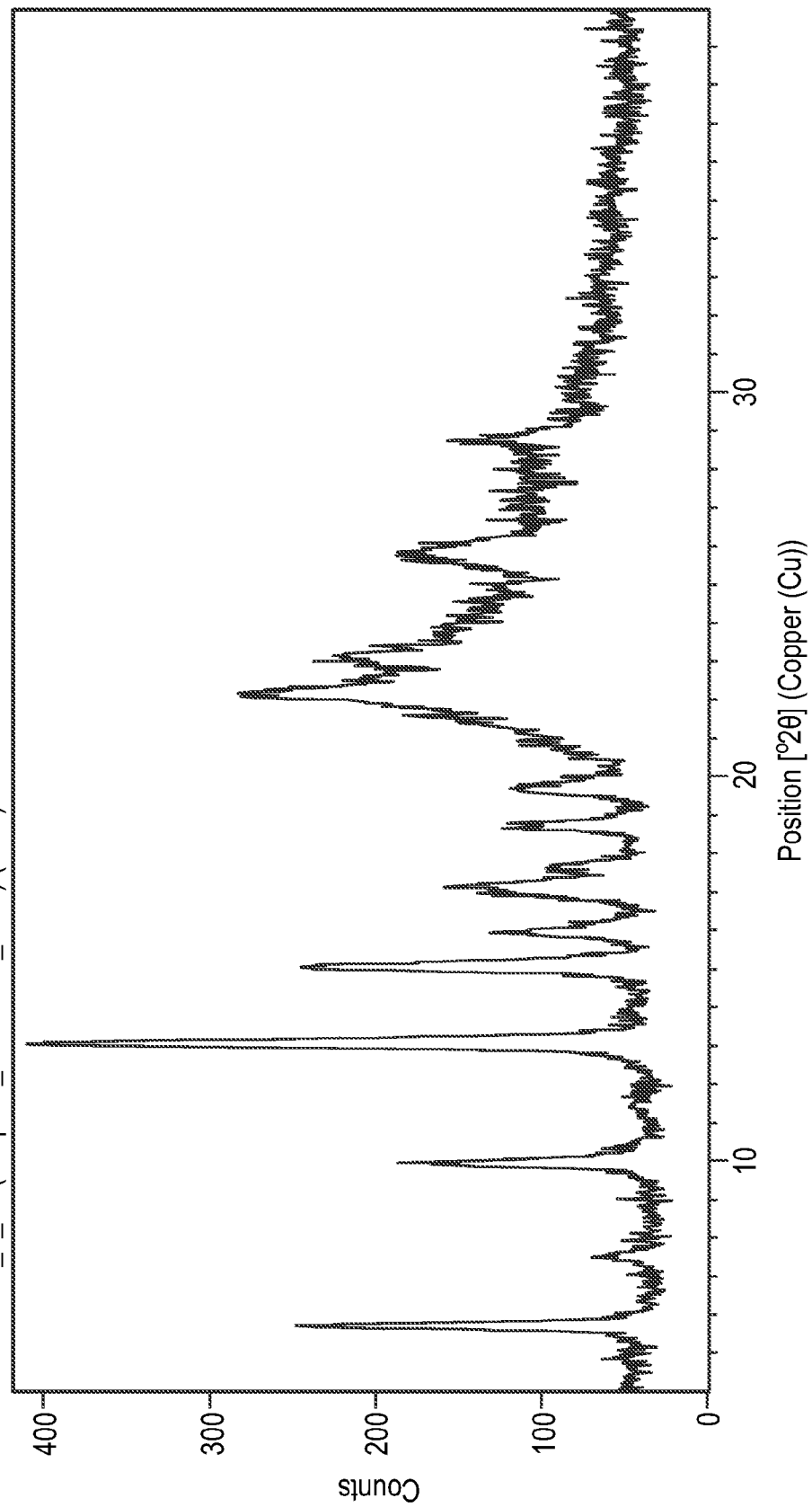
FIG. 3: X-ray powder diffraction pattern of Form 2 of the compound of Formula A (Example 2).

The present invention also provides a solid form (Form 2) of the compound of Formula A having an X-ray powder diffraction pattern substantially the same as that shown in FIG. 3.

The present invention provides a solid form (Form 3) of the compound of Formula A, which exhibits at least the following characteristic X-ray powder diffraction peaks (Cu Kα radiation, expressed in degrees 2θ) at approximately:
(1) 7.0, 10.3, 14.1, 16.3, and 18.2; or
(2) 7.0, 9.5, 10.3, 10.8, 14.1, 16.3, and 18.2; or
(3) 7.0, 9.5, 10.3, 10.8, 12.0, 14.1, 16.3, 18.2, and 24.1.

The present invention also provides a solid form (Form 3) of the compound of Formula A, having an X ray powder diffraction pattern comprising characteristic peaks (expressed in degrees 2θ) at approximately 7.0, 9.5, 10.3, 10.8, 11.4, 12.0, 14.1, 16.3, 18.2, 24.1, and 25.3.

Figure 4:
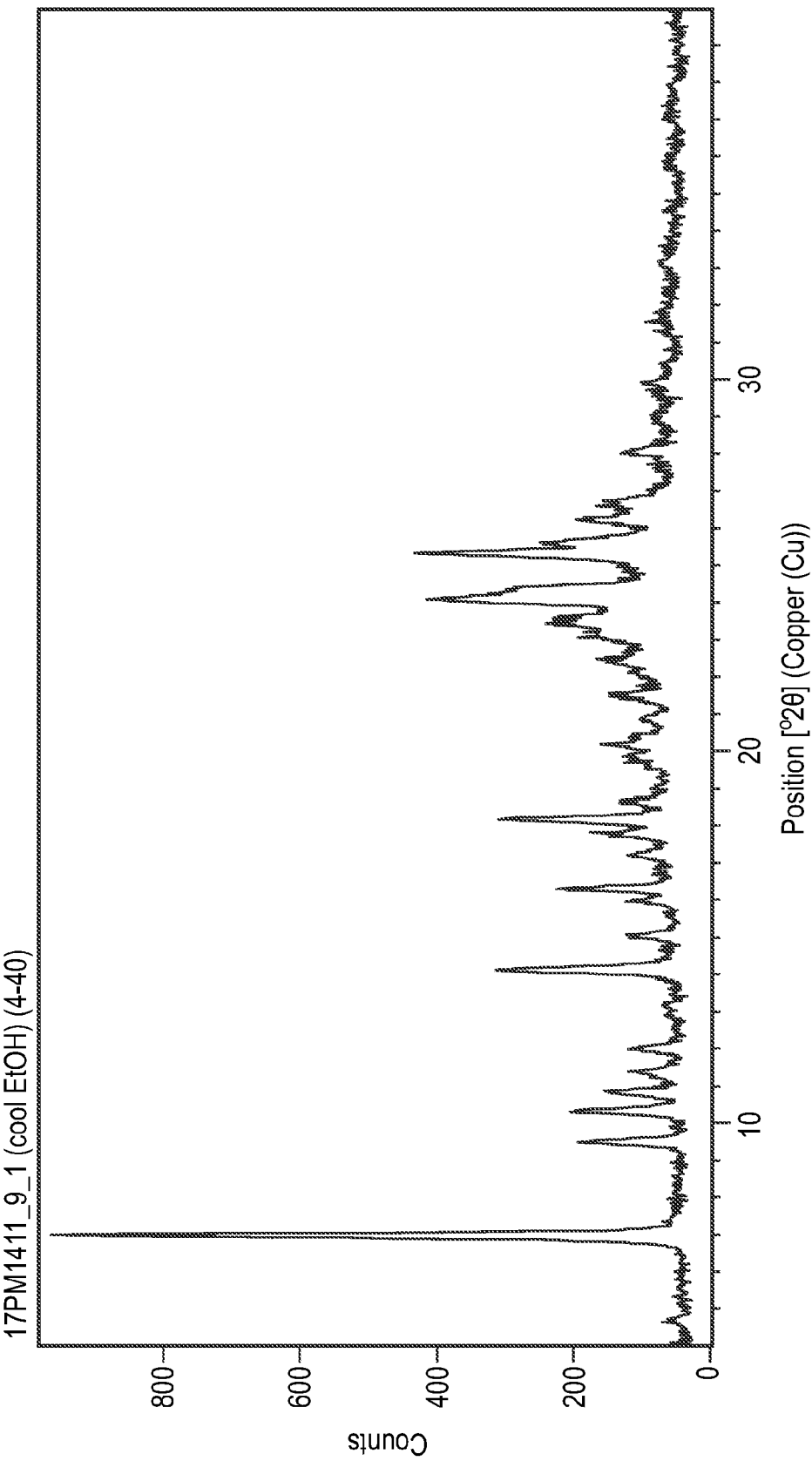
FIG. 4: X-ray powder diffraction pattern of Form 3 of the compound of Formula A (Example 3).

The present invention also provides a solid form (Form 3) of the compound of Formula A having an X-ray powder diffraction pattern substantially the same as that shown in FIG. 4.

The present invention provides a solid form (Form 4) of the compound of Formula A, which exhibits at least the following characteristic X-ray powder diffraction peaks (Cu Kα radiation, expressed in degrees 2θ) at approximately:
(1) 4.8, 9.5, 11.0, 14.3, and 15.3; or
(2) 4.8, 7.8, 9.5, 11.0, 11.7, 14.3, and 15.3; or
(3) 4.8, 7.8, 9.5, 11.0, 11.7, 14.3, 15.3, 18.2, and 20.2.

The present invention also provides a solid form (Form 4) of the compound of Formula A, having an X ray powder diffraction pattern comprising characteristic peaks (expressed in degrees 2θ) at approximately 4.8, 7.8, 9.5, 11.0, 11.7, 14.3, 15.3, 15.9, 18.2, 20.2, and 22.2.

Figure 5:
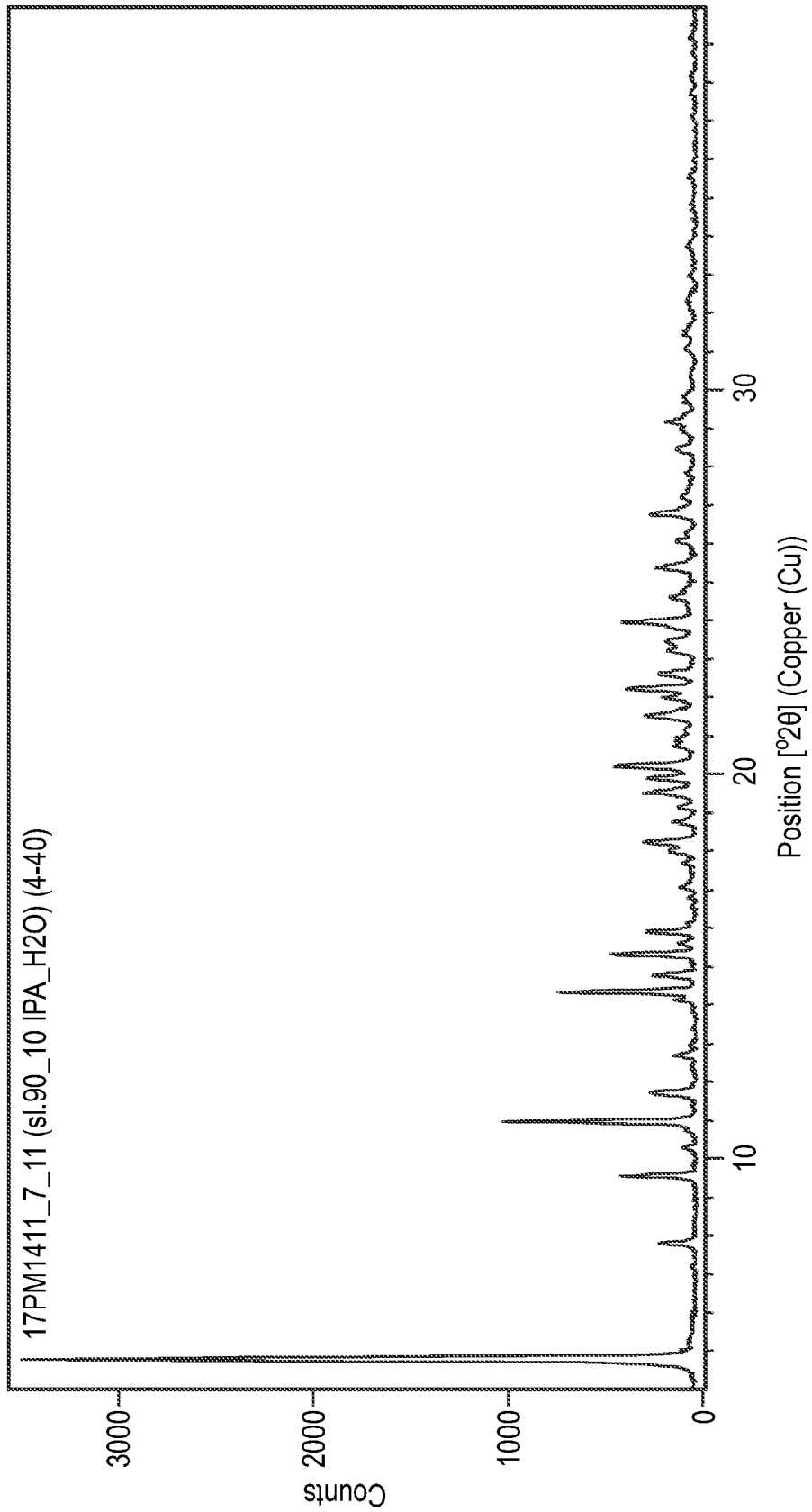
FIG. 5: X-ray powder diffraction pattern of Form 4 of the compound of Formula A (Example 4).

The present invention also provides a solid form (Form 4) of the compound of Formula A having an X-ray powder diffraction pattern substantially the same as that shown in FIG. 5.

The present invention also provides a solid form (Form 5) of the compound of Formula A, having an X-ray powder diffraction pattern comprising characteristic peaks (expressed in degrees 2θ) at approximately 10.4, 15.6, 16.7 and 20.8.

Figure 6:
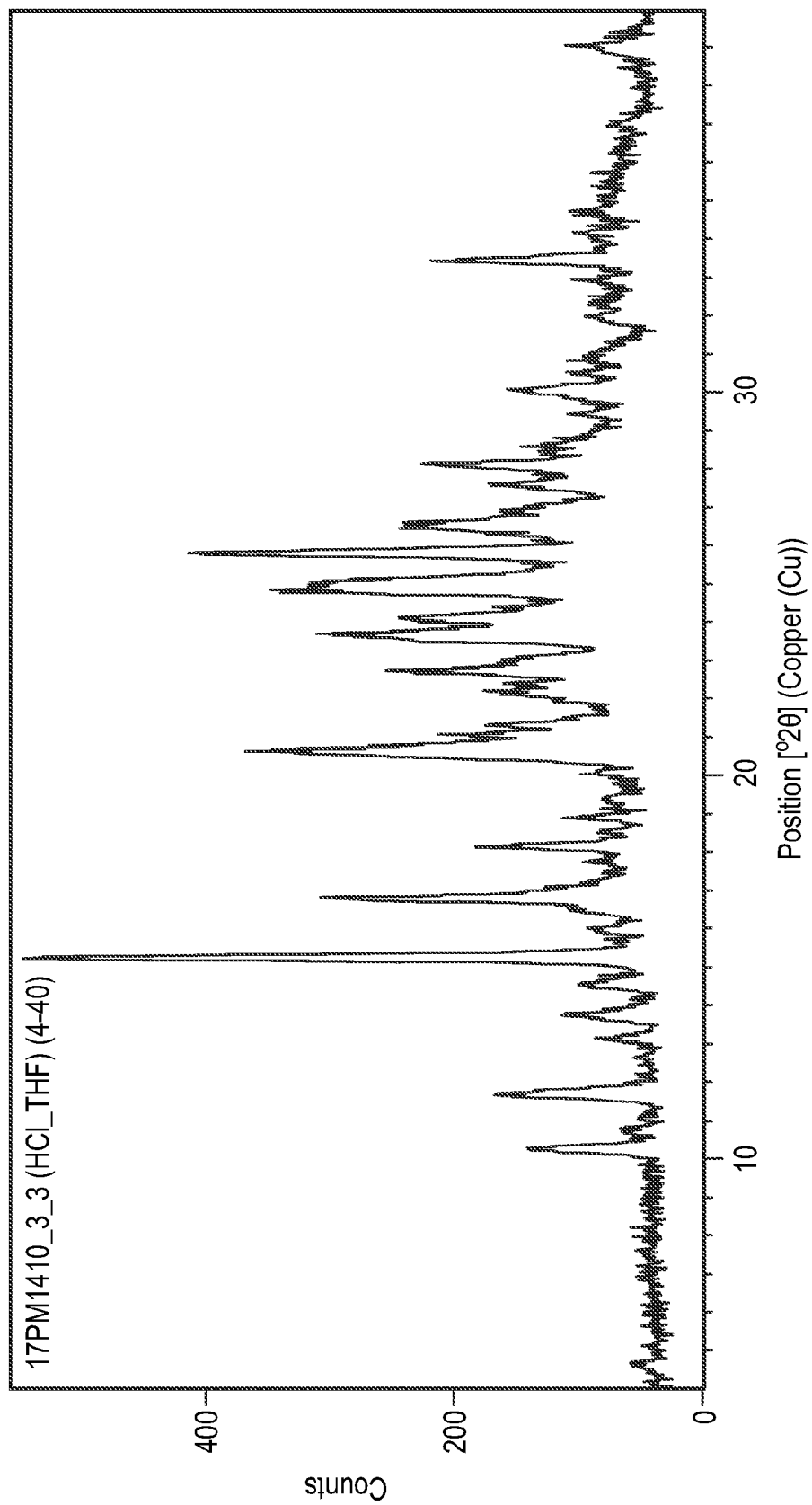
FIG. 6: X-ray powder diffraction pattern of Form 5 of the hydrochloride salt of the compound of Formula A (Example 5).

The present invention also provides a solid form (Form 5) of the hydrochloride salt of the compound of Formula A having an X-ray powder diffraction pattern substantially the same as that shown in FIG. 6.

Figure 7:
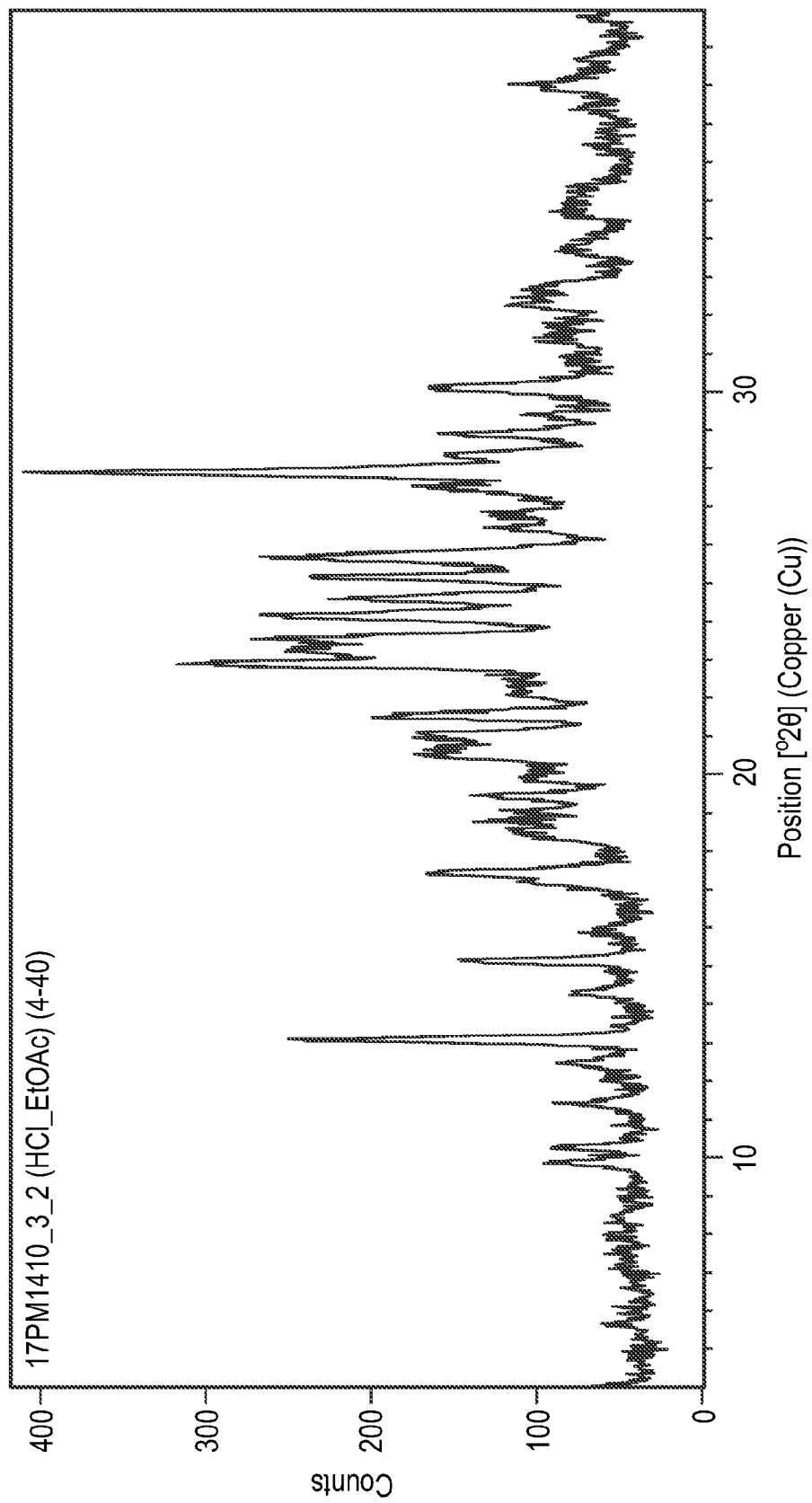
FIG. 7: X-ray powder diffraction pattern of Form 6 of the hydrochloride salt of the compound of Formula A (Example 6).

The present invention also provides a solid form (Form 6) of the hydrochloride salt of the compound of Formula A having an X-ray powder diffraction pattern substantially the same as that shown in FIG. 7.

Figure 8:
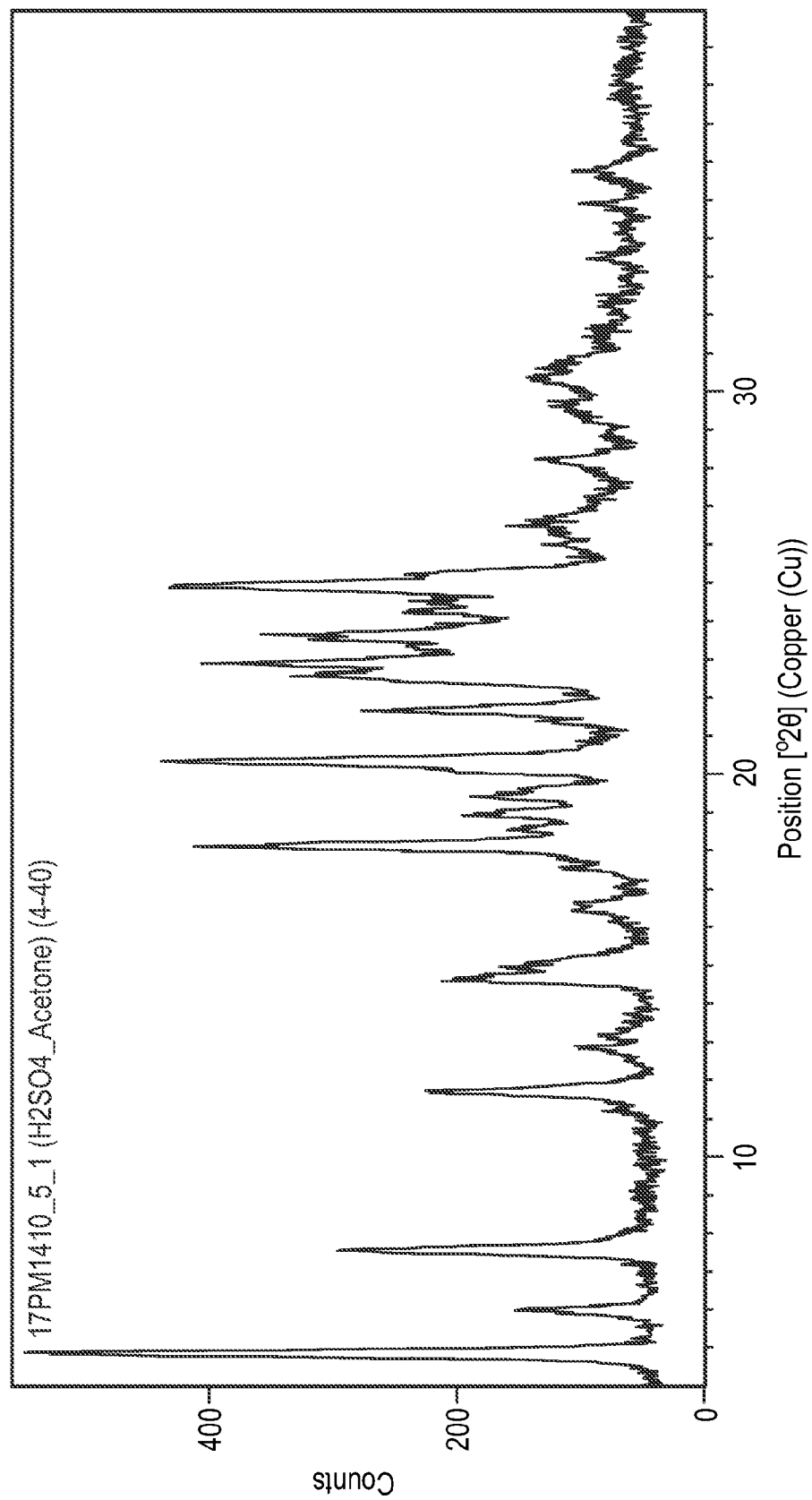
FIG. 8: X-ray powder diffraction pattern of Form 7 of the sulfate salt of the compound of Formula A (Example 7).

The present invention also provides a solid form (Form 7) of the sulfate salt of the compound of Formula A having an X-ray powder diffraction pattern substantially the same as that shown in FIG. 8.

Figure 9:
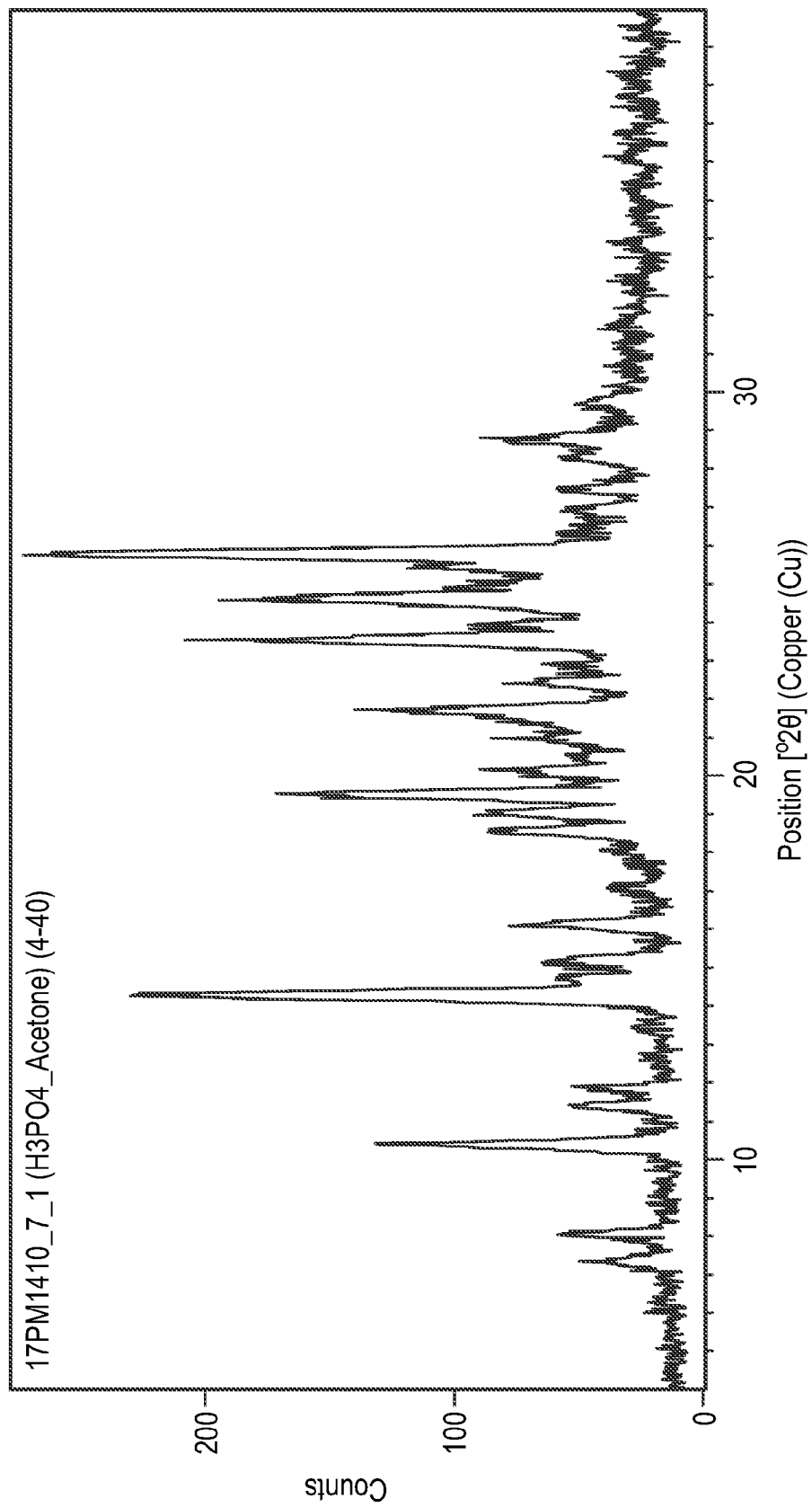
FIG. 9: X-ray powder diffraction pattern of Form 8 of the phosphate salt of the compound of Formula A (Example 8).

The present invention also provides a solid form (Form 8) of the phosphate salt of the compound of Formula A having an X-ray powder diffraction pattern substantially the same as that shown in FIG. 9.

Figure 10:
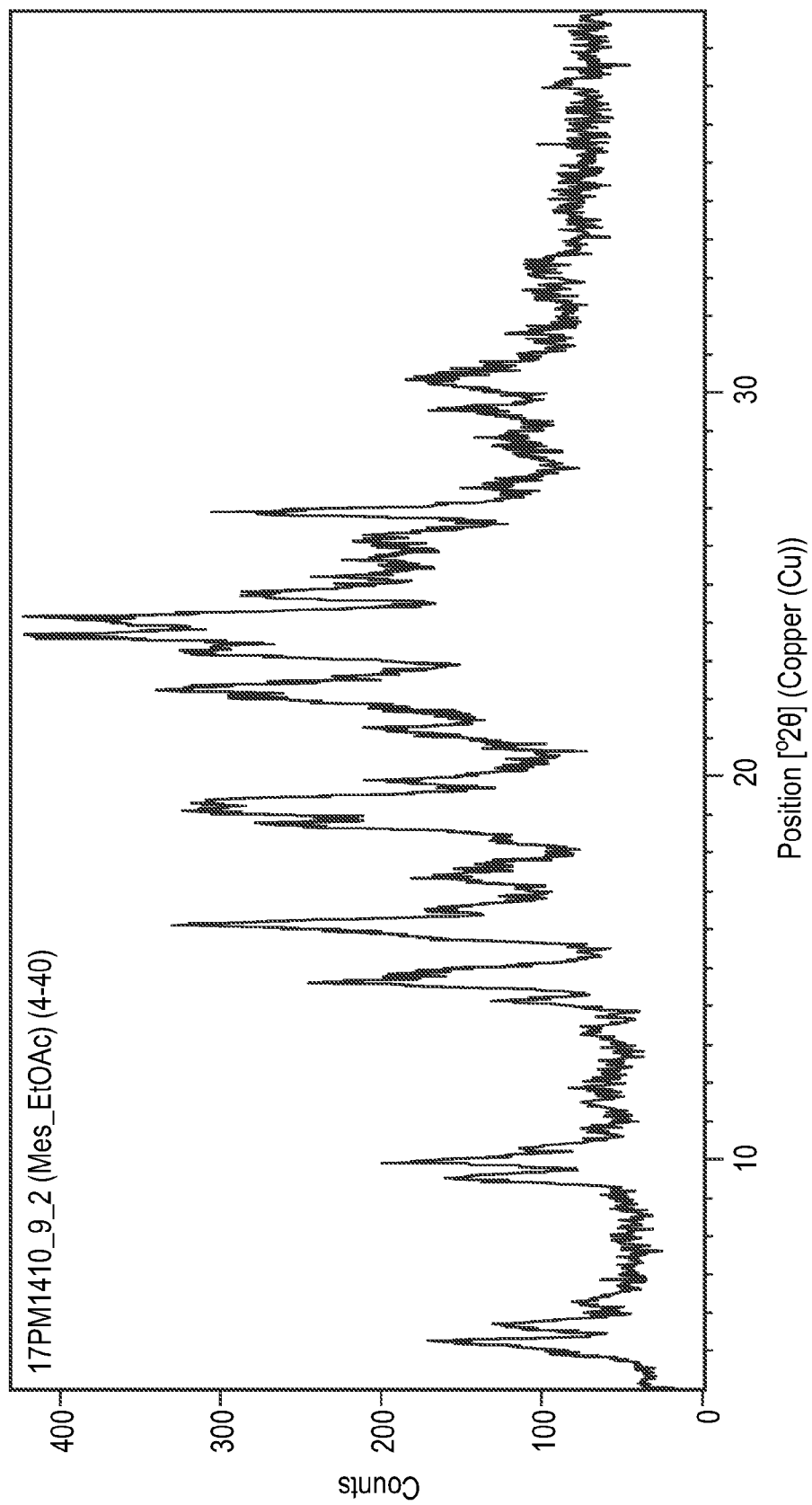
FIG. 10: X-ray powder diffraction pattern of Form 9 of the mesylate salt of the compound of Formula A (Example 9).

The present invention also provides a solid form (Form 9) of the mesylate salt of the compound of Formula A having an X-ray powder diffraction pattern substantially the same as that shown in FIG. 10.

Figure 11:
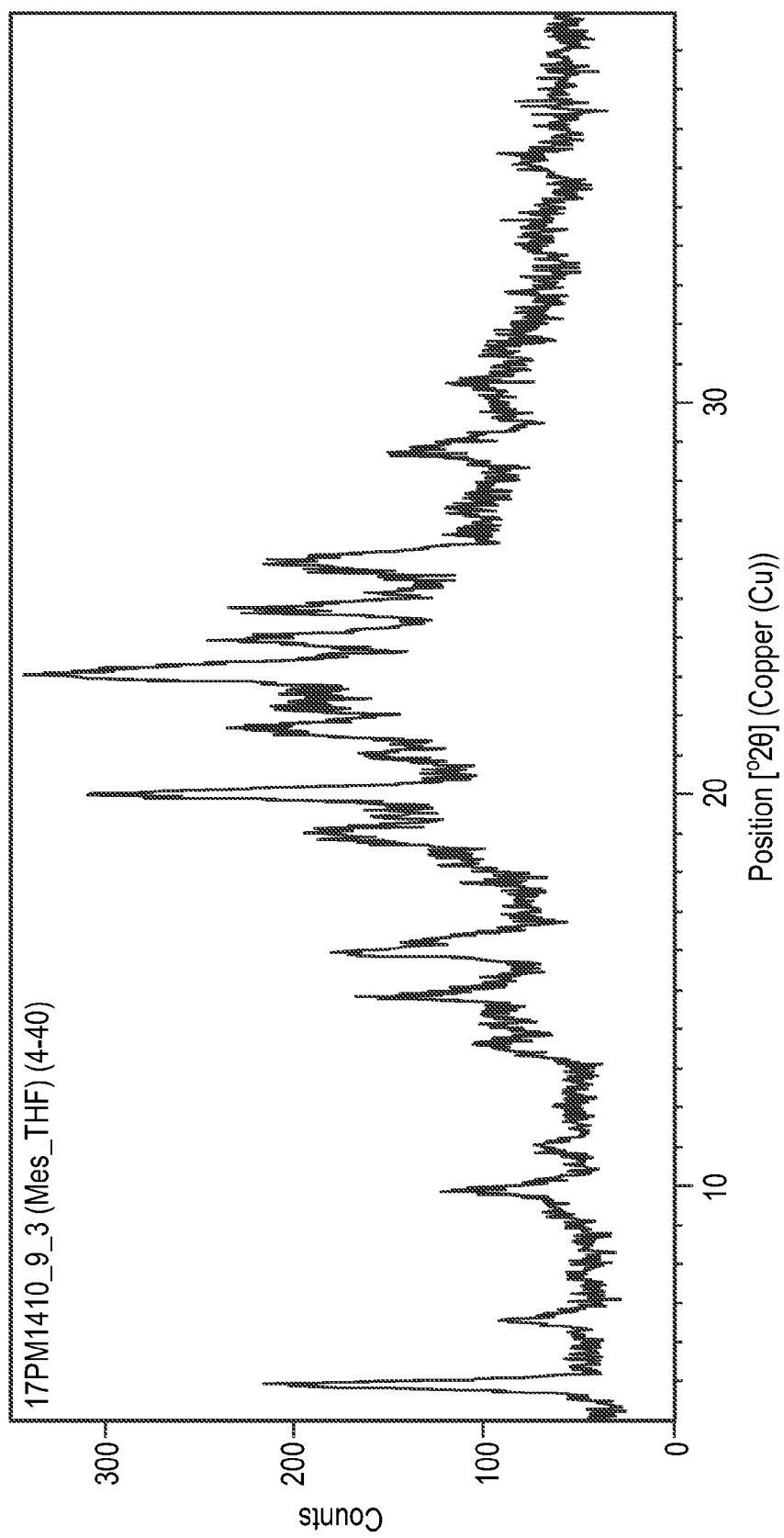
FIG. 11: X-ray powder diffraction pattern of Form 10 of the mesylate salt of the compound of Formula A (Example 10).

The present invention also provides a solid form (Form 10) of the mesylate salt of the compound of Formula A having an X-ray powder diffraction pattern substantially the same as that shown in FIG. 11.

Figure 12:
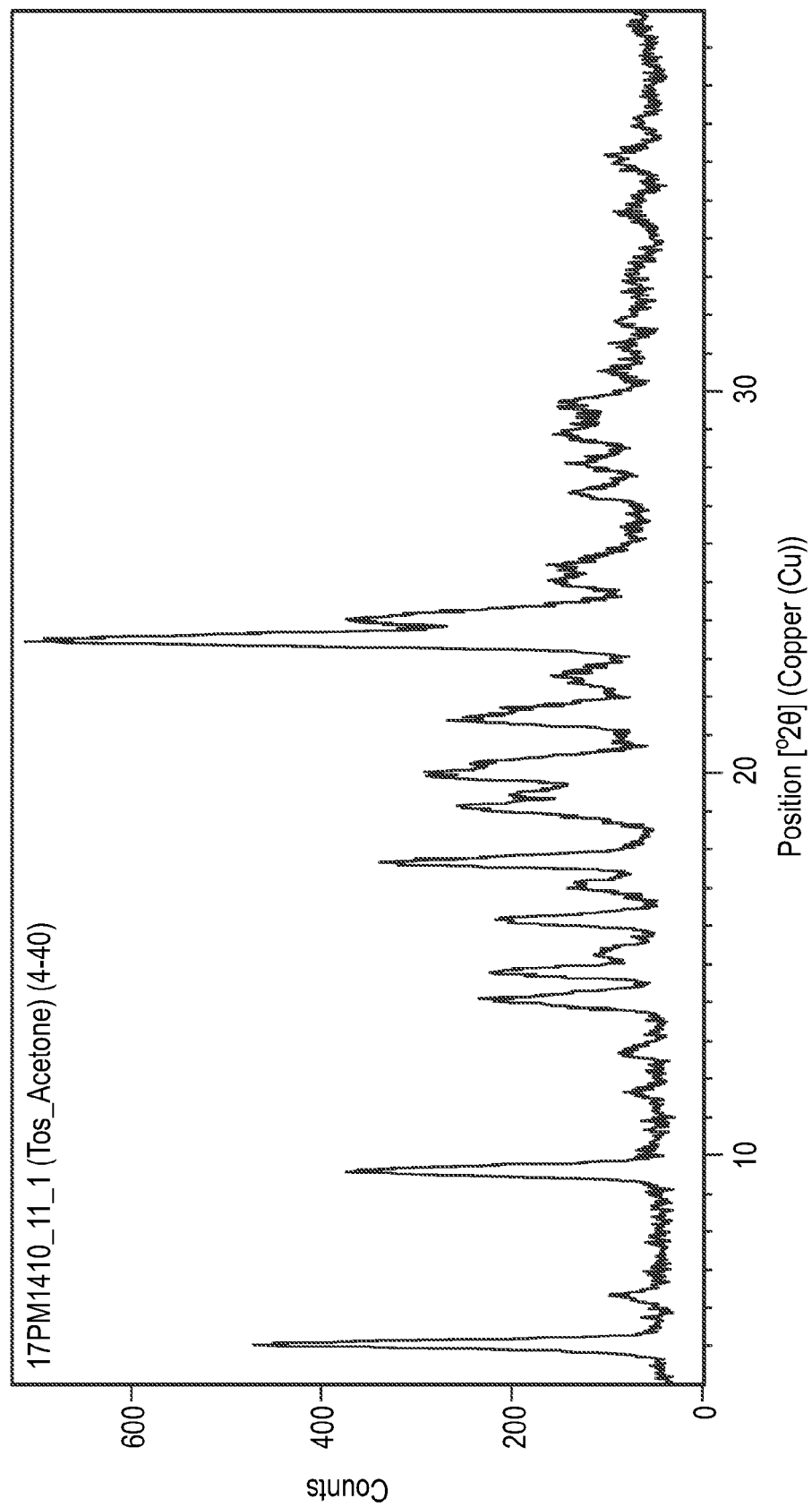
FIG. 12: X-ray powder diffraction pattern of Form 11 of the tosylate salt of the compound of Formula A (Example 11).

The present invention also provides a solid form (Form 11) of the tosylate salt of the compound of Formula A having an X-ray powder diffraction pattern substantially the same as that shown in FIG. 12.

Figure 13:
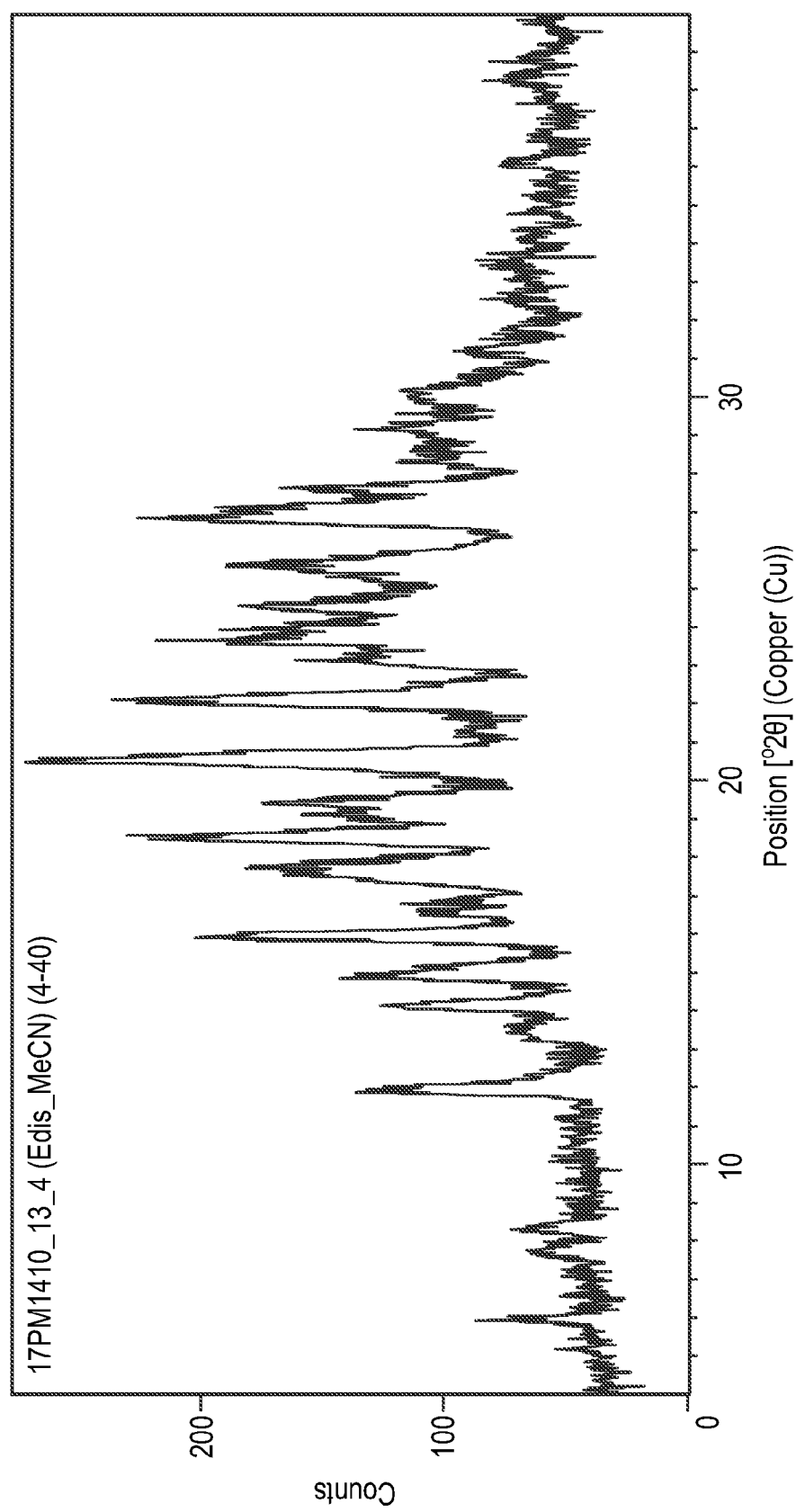
FIG. 13: X-ray powder diffraction pattern of Form 12 of the edisylate salt of the compound of Formula A (Example 12).

The present invention also provides a solid form (Form 12) of the edisylate salt of the compound of Formula A having an X-ray powder diffraction pattern substantially the same as that shown in FIG. 13.

Figure 14:
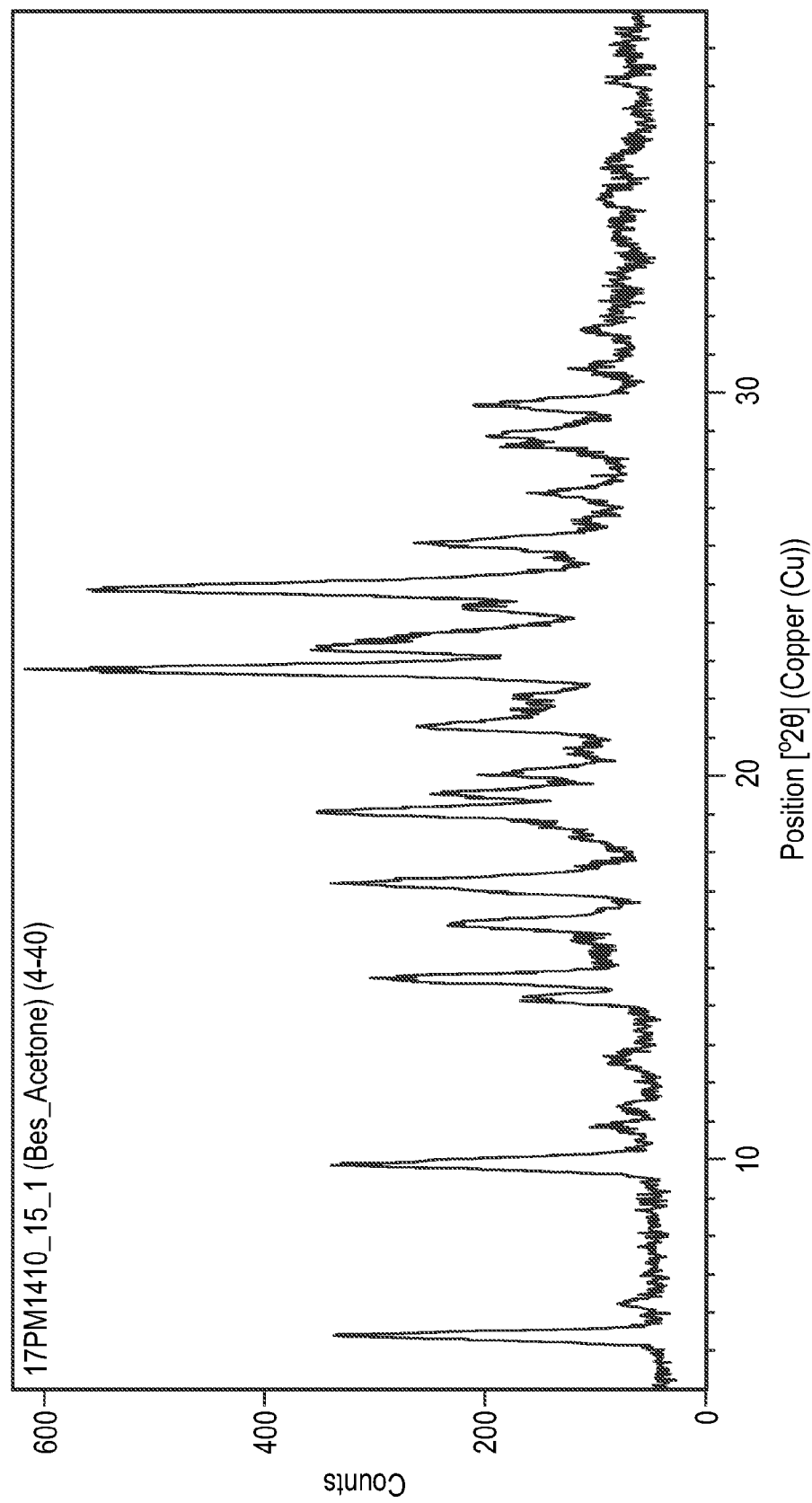
FIG. 14: X-ray powder diffraction pattern of Form 13 of the besylate salt of the compound of Formula A (Example 13).

The present invention also provides a solid form (Form 13) of the besylate salt of the compound of Formula A having an X-ray powder diffraction pattern substantially the same as that shown in FIG. 14.

The present invention provides a solid form (Form 14) of the compound of Formula A which exhibits at least the following characteristic X-ray powder diffraction peaks (Cu Kα radiation, expressed in degrees 2θ) at approximately:
(1) 9.6, 13.2, 15.4, 18.0 and 20.7; or
(2) 9.6, 13.2, 15.4, 18.0, 19.5, 20.7 and 23.2; or
(3) 9.6, 13.2, 15.4, 18.0, 19.5, 20.7, 23.2, 23.3, 24.2 and 24.4.

The present invention also provides a solid form (Form 14) of the compound of Formula A, having an X ray powder diffraction pattern comprising characteristic peaks (expressed in degrees 2θ) at approximately 9.6, 13.2, 15.4, 18.0, 19.5, 20.7, 23.2, 23.3, 24.2, 24.4, 25.7 and 26.2.

Figure 15:
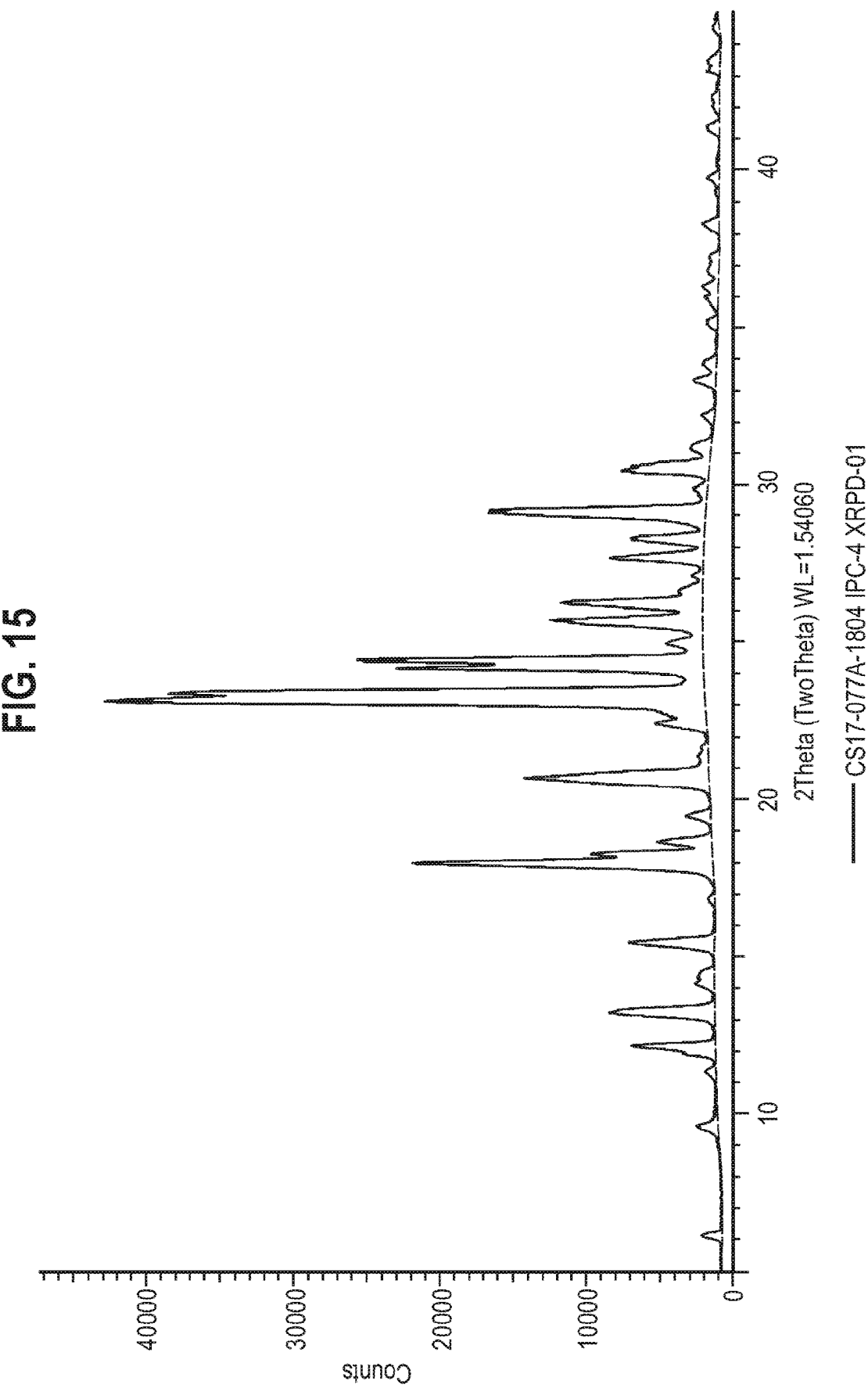
FIG. 15: X-ray powder diffraction pattern of Form 14 of the compound of Formula A (Example 14).

The present invention also provides a solid form (Form 14) of the compound of Formula A having an X-ray powder diffraction pattern substantially the same as that shown in FIG. 15.

The present invention provides a solid form (Form 15) of the hydrochloride salt of the compound of Formula A, which exhibits at least the following characteristic X-ray powder diffraction peaks (Cu Kα radiation, expressed in degrees 2θ) at approximately:
(1) 10.0, 10.7, 12.4, 13.9 and 16.6; or
(2) 9.2, 10.0, 10.7, 12.4, 13.9, 16.6 and 20; or
(3) 9.2, 10.0, 10.7, 12.4, 13.9 15.8, 16.6 20.0 and 24.8.

The present invention also provides a solid form (Form 15) of the hydrochloride salt of the compound of Formula A, having an X ray powder diffraction pattern comprising characteristic peaks (expressed in degrees 2θ) at approximately 9.2, 10.0, 10.7, 12.4, 13.9, 15.8, 16.6, 17.4, 18.4 and 24.8.

Figure 18:
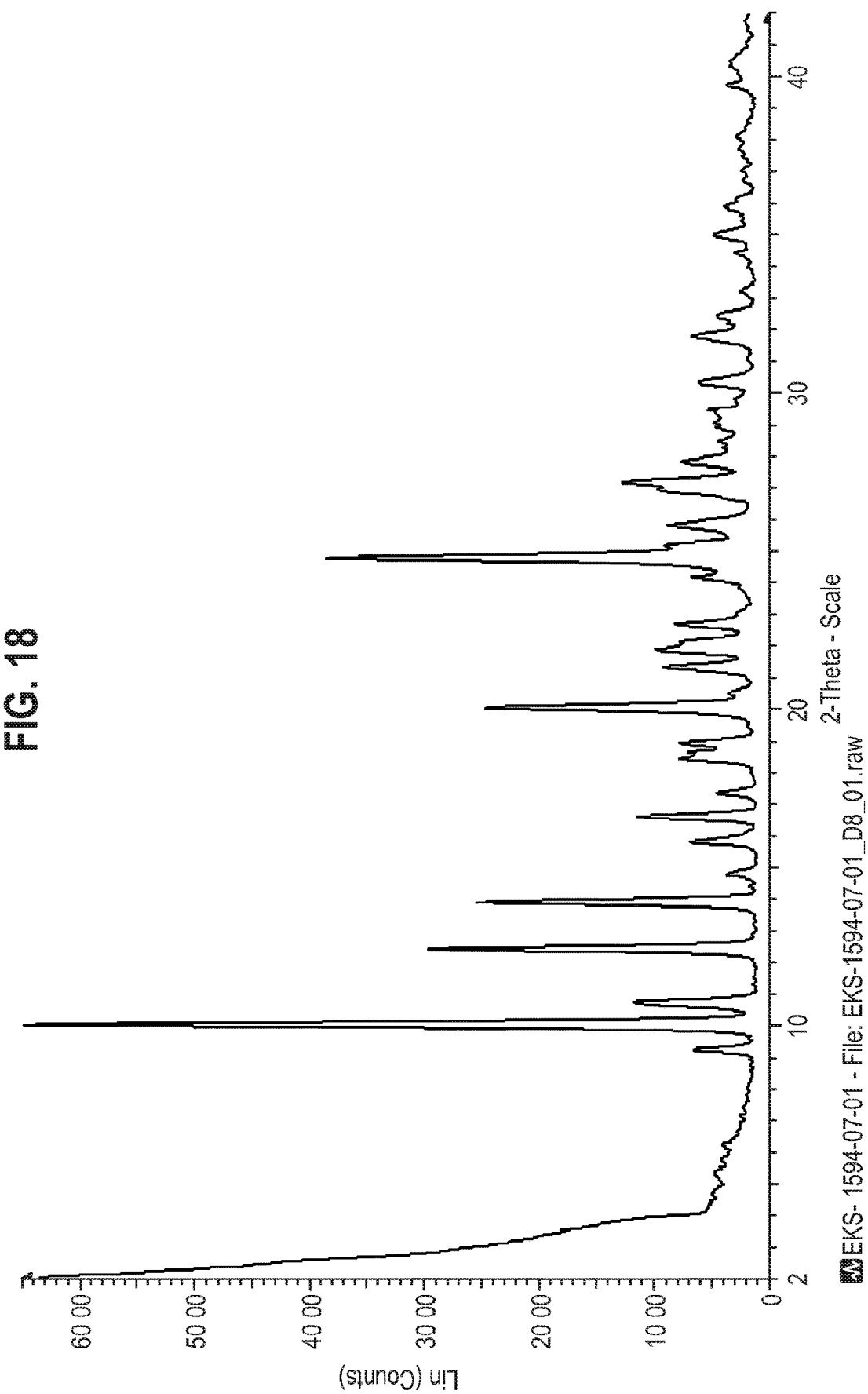
FIG. 18: X-ray powder diffraction pattern of Form 15 of the hydrochloride salt of the compound of Formula A (Example 15).

The present invention also provides a solid form (Form 15) of the hydrochloride salt of the compound of Formula A having an X-ray powder diffraction pattern substantially the same as that shown in FIG. 18.

The skilled person is familiar with techniques for measuring XRPD patterns. In particular, the X-ray powder diffraction pattern of the sample of compound may be recorded using a Philips X-Pert MPD diffractometer with the following experimental conditions:

| Scan parameters: | |
|---|---|
| Scan Axis: | Gonio |
| Start Position [°2θ]: | 4.0084 |
| End Position [°2θ]: | 39.9804 |

| Scan parameters: | |
|---|---|
| Step Size [°2θ]: | 0.0170 |
| Scan Step Time [s]: | 10.1600 |
| Scan Type: | Continuous |
| PSD Mode: | Scanning |
| PSD Length [°2θ]: | 2.12 |
| Offset [°2θ]: | 0.0000 |
| Divergence Slit Type: | Automatic |
| Irradiated Length [mm] | 10.00 |
| Specimen Length [mm]: | 10.00 |
| Measurement Temperature [° C.]: | 25.00 |
| Anode Material: | Cu |
| K-Alpha1 [Å]: | 1.54060 |
| K-Alpha2 [Å]: | 1.54443 |
| K-A2/K-A1 Ratio: | 0.50000 |
| Generator Settings: | 40 mA, 40 kV |
| Diffractometer Type: | 0000000011038600 |
| Diffractometer Number: | 0 |
| Goniometer Radius [mm]: | 240.00 |
| Dist. Focus-Diverg. Slit [mm]: | 100.00 |
| Incident Beam Monochromator: | No |
| Spinning: | Yes |

Sample: Approximately 5 mg of sample under analysis gently compressed on the XRPD zero back ground single obliquely cut silica sample holder.

The present invention provides a solid form (Form 1) of the compound of Formula A, which exhibits an endothermic peak in its STA thermograph at 148±3° C., preferably 148±2° C., more preferably 148±1° C.

Figure 2:
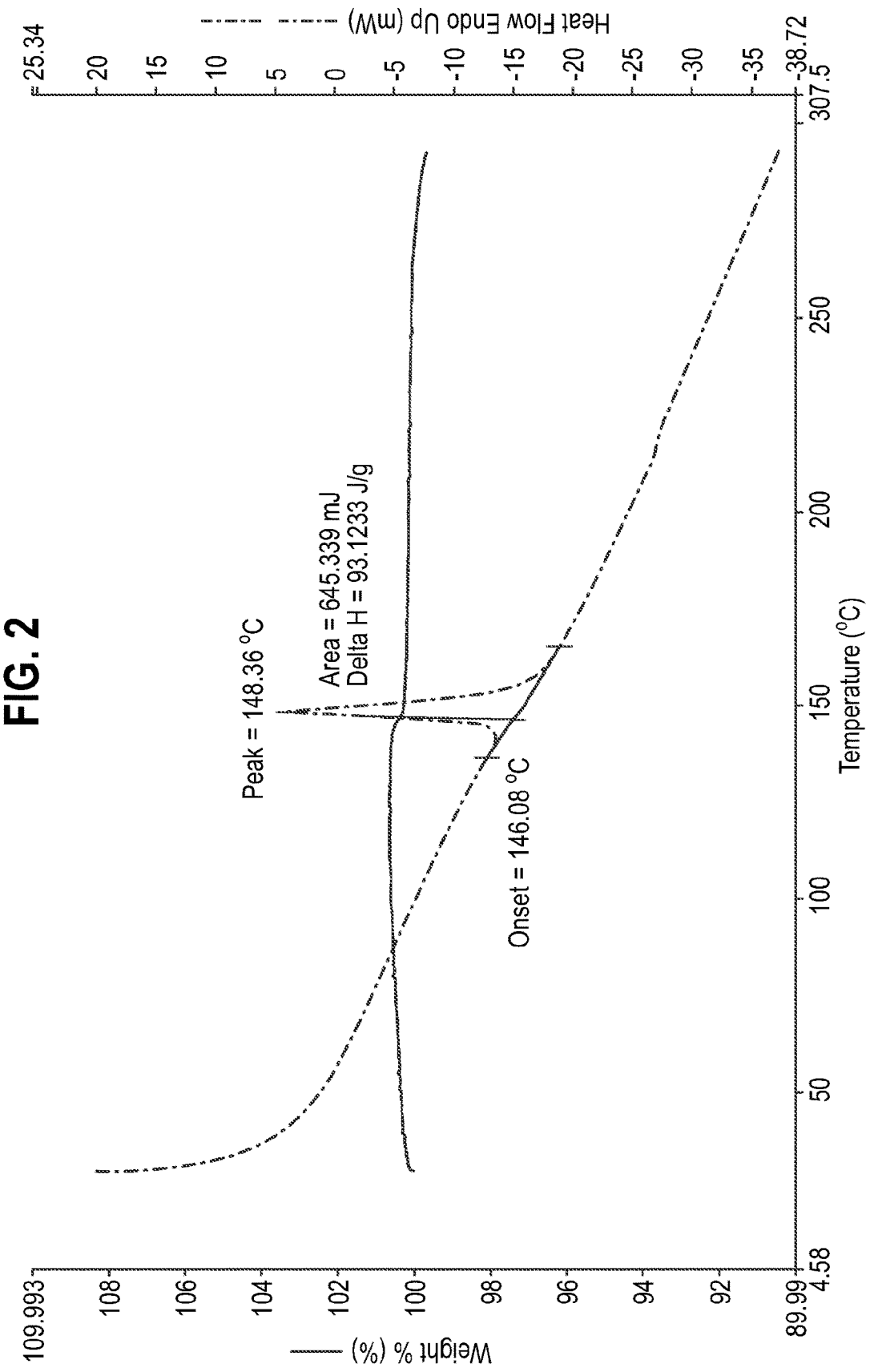
FIG. 2: STA of Form 1 of the compound of Formula A (Example 1).

The present invention provides a solid form (Form 1) of the compound of Formula A, having an STA thermograph substantially the same as that shown in FIG. 2.

The present invention provides a solid form (Form 14) of the compound of Formula A, which exhibits an endothermic peak in its DSC thermograph at 158±3° C., preferably 158±2° C., more preferably 158±1° C.

Figure 16:
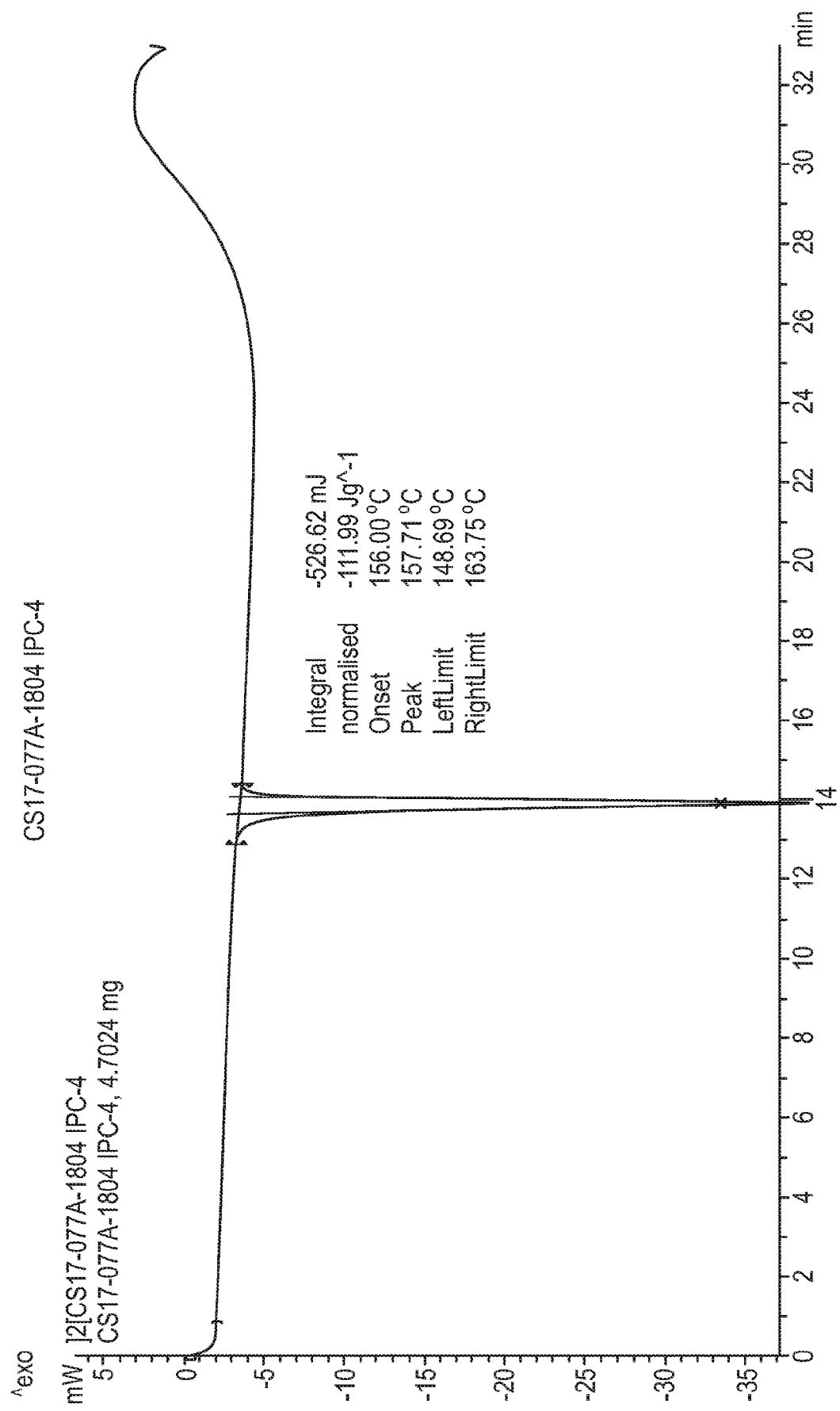
FIG. 16: DSC of Form 14 of the compound of Formula A (Example 14).

The present invention provides a solid form (Form 14) of the compound of Formula A, having an DSC thermograph substantially the same as that shown in FIG. 16.

The invention provides a solid form (Form 15) of the hydrochloride salt of the compound of Formula A, which exhibits an endothermic peak in its DSC thermograph at 166±3° C., preferably 166±2° C., more preferably 166±1° C.

Figure 19:
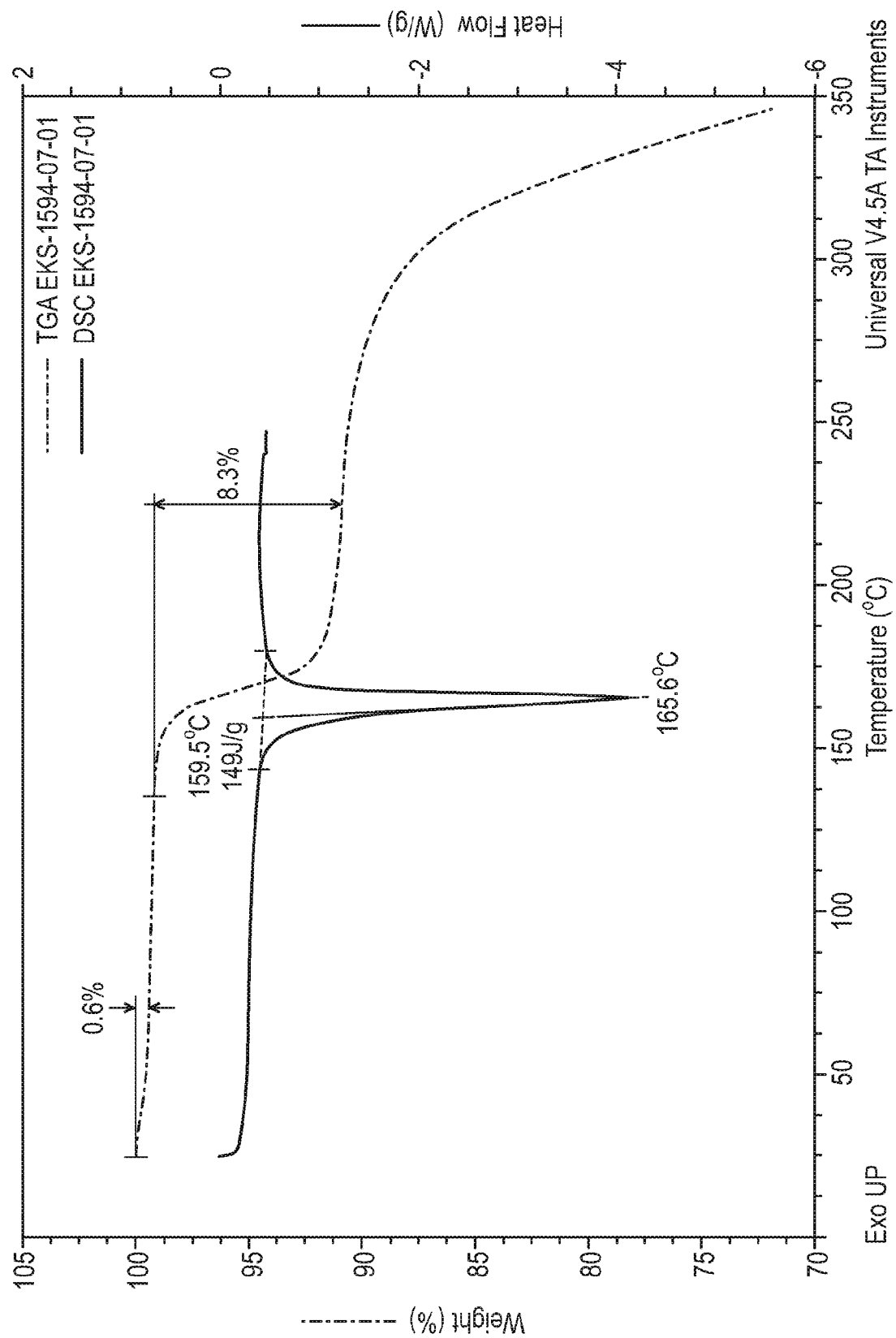
FIG. 19: TGA/DSC of Form 15 of the hydrochloride salt of the compound of Formula A (Example 15).

The present invention provides a solid form (Form 15) of the hydrochloride salt of the compound of Formula A, having a TGA/DSC thermograph substantially the same as that shown in FIG. 19.

The skilled person is familiar with techniques for measuring STA thermographs. In particular, the STA thermograph of the sample of compound may be recorded by
(a) weighing approximately 5 mg of sample into a ceramic crucible;
(b) loading the sample into the chamber of Perkin-Elmer STA 600 TGA/DTA analyzer at ambient temperature;
(c) heating the sample from 25° C. to 300° C. at a rate of 10° C./min, and monitoring the change in weight of the sample as well as DTA signal while using a 20 cm³/min nitrogen purge.

The skilled person will be familiar with techniques for measuring Thermogravimetric Analysis (TGA) thermographs and Differential Scanning Calorimetry thermographs separately rather than together using an STA technique.

In particular, the TGA thermograph of the sample of compound may be recorded by
(a) weighing approximately 5 to 10 mg of sample into a pre-tared aluminium DSC pan
(b) loading the sample into the chamber of a TA Instruments Q500TGA equipped with a 16 position auto-sampler at ambient temperature;

(c) heating the sample from ambient temperature to 350° C. at a rate of 10° C./min while maintaining a nitrogen purge of 60 ml/min over the sample.

The DSC thermograph of the sample of compound may be recorded by
(a) weighing approximately 0.5-3 mg of sample into a pin-holed aluminium DSC pan
(b) loading the sample into the chamber of a TA Instruments Q2000 or TA Instruments Discovery DSC equipped with a 50 position auto-sampler at ambient temperature;
(c) heating the sample from 25° C. to 250° C. at a rate of 10° C./min while maintaining a nitrogen purge of 50 ml/min over the sample.

The present invention provides a solid form (Form 1) of the compound of Formula A having an X-ray powder diffraction pattern as described above, and an STA thermograph as described above.

The present invention provides a solid form (Form 14) of the compound of Formula A having an X-ray powder diffraction pattern as described above, and an STA thermograph as described above.

The present invention provides a solid form (Form 15) of the hydrochloride salt of the compound of formula A having an X-ray powder diffraction pattern as described above, and a DSC thermograph as described above.

The solid form of the present invention can exist in both unsolvated and solvated forms. The term 'solvate' is used herein to describe a molecular complex comprising the compound of the invention and an amount of one or more pharmaceutically acceptable solvents, for example, ethanol. The term 'hydrate' is employed when the solvent is water.

The present invention encompasses solvates (e.g. hydrates) of the solid forms of the compound of Formula A and salts thereof described herein.

In an aspect of the invention, Form 1 of the compound of Formula A is not a solvate or a hydrate.

In an aspect of the invention, Form 14 of the compound of Formula A is not a solvate or a hydrate.

In an aspect of the invention, Form 5 of the hydrochloride salt of the compound of Formula A is not a solvate or hydrate.

In an aspect of the invention, Form 15 of the hydrochloride salt of the compound of Formula A is not a solvate or hydrate.

A reference to a particular compound also includes all isotopic variants.

The present invention also encompasses a process for the preparation of Form 1 of the present invention, said process comprising the crystallisation of said solid form from a solution of the compound of Formula A in a solvent or a mixture of solvents. The solvent or mixture of solvents may comprise isopropanol (IPA). Preferably the solvent is isopropanol. After adding the compound of Formula A to a solvent or a mixture of solvents (e.g. isopropanol), the combined mixture (compound plus solvent(s)) may be heated to a temperature of approximately 60-85° C. Alternatively, the combined mixture may be heated to a temperature of approximately 70-85° C. Alternatively, the combined mixture may be heated to a temperature of approximately 80-85° C. Alternatively, the combined mixture may be heated to a temperature of approximately 80, 81, 82, 83, 84 or 85° C. Alternatively, the combined mixture may be heated to a temperature of approximately 82° C. Alternatively, the combined mixture may be heated to reflux. Following heating, the combined mixture may be cooled. Alternatively, the combined mixture may be cooled to a temperature of approximately 0-40° C. Alternatively, the combined mixture may be cooled to a temperature of approximately 10-30° C. Alternatively, the combined mixture may be cooled to room temperature. Alternatively, the combined mixture may be cooled to approximately 0° C.

The present invention also encompasses a process for the preparation of Form 5 of the present invention, said process comprising the crystallisation of said solid form from a solution of the hydrochloride salt of the compound of Formula A in a solvent or a mixture of solvents. Optionally, said solution of the hydrochloride salt of the compound of Formula A may be formed by adding hydrochloric acid to a solution or suspension of the compound of Formula A in a solvent or a mixture of solvents. Preferably, the solvent is THF, acetone or acetonitrile. More preferably, the solvent is THF. The crystallisation may be performed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours. The solvent or mixture of solvents may be removed by decanting off the solvent or mixture of solvents, and/or by evaporation of the solvent or mixture of solvents under a stream of inert gas, preferably under a stream of nitrogen.

The present invention also encompasses a process for the preparation of Form 6 of the present invention, said process comprising the crystallisation of said solid form from a solution of the hydrochloride salt of the compound of Formula A in a solvent or a mixture of solvents. Optionally, said solution of the hydrochloride salt of the compound of Formula A may be formed by adding hydrochloric acid to a solution or suspension of the compound of Formula A in a solvent or a mixture of solvents.

Preferably, the solvent is ethyl acetate. The crystallisation may be performed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours. The solvent or mixture of solvents may be removed by decanting off the solvent or mixture of solvents, and/or by evaporation of the solvent or mixture of solvents under a stream of inert gas, preferably under a stream of nitrogen.

The present invention also encompasses a process for the preparation of Form 7 of the present invention, said process comprising the crystallisation of said solid form from a solution of the sulfate salt of the compound of Formula A in a solvent or a mixture of solvents. Optionally, said solution of the sulfate salt of the compound of Formula A may be formed by adding sulfuric acid to a solution or suspension of the compound of Formula A in a solvent or a mixture of solvents. Preferably, the solvent is ethyl acetate, THF, acetone or acetonitrile. More preferably, the solvent is acetone. The crystallisation may be performed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours. The solvent or mixture of solvents may be removed by decanting off the solvent or mixture of solvents, and/or by evaporation of the solvent or mixture of solvents under a stream of inert gas, preferably under a stream of nitrogen.

The present invention also encompasses a process for the preparation of Form 8 of the present invention, said process comprising the crystallisation of said solid form from a solution of the phosphate salt of the compound of Formula A in a solvent or a mixture of solvents. Optionally, said solution of the phosphate salt of the compound of Formula A may be formed by adding orthophosphoric acid to a solution or suspension of the compound of Formula A in a solvent or a mixture of solvents. Preferably, the solvent is acetone or acetonitrile. More preferably, the solvent is acetone. The crystallisation may be performed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours. The solvent or mixture of solvents may be removed by decanting off the solvent or mixture of solvents, and/or by evaporation of the solvent or mixture of solvents under a stream of inert gas, preferably under a stream of nitrogen.

The present invention also encompasses a process for the preparation of Form 9 of the present invention, said process comprising the crystallisation of said solid form from a solution of the mesylate salt of the compound of Formula A in a solvent or a mixture of solvents. Optionally, said solution of the mesylate salt of the compound of Formula A may be formed by adding methanesulfonic acid to a solution or suspension of the compound of Formula A in a solvent or a mixture of solvents. Preferably, the solvent is ethyl acetate or acetone. More preferably, the solvent is ethyl acetate. The crystallisation may be performed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours. The solvent or mixture of solvents may be removed by decanting off the solvent or mixture of solvents, and/or by evaporation of the solvent or mixture of solvents under a stream of inert gas, preferably under a stream of nitrogen.

The present invention also encompasses a process for the preparation of Form 10 of the present invention, said process comprising the crystallisation of said solid form from a solution of the mesylate salt of the compound of Formula A in a solvent or a mixture of solvents. Optionally, said solution of the mesylate salt of the compound of Formula A may be formed by adding methanesulfonic acid to a solution or suspension of the compound of Formula A in a solvent or a mixture of solvents. Preferably, the solvent is THF. The crystallisation may be performed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours. The solvent or mixture of solvents may be removed by decanting off the solvent or mixture of solvents, and/or by evaporation of the solvent or mixture of solvents under a stream of inert gas, preferably under a stream of nitrogen.

The present invention also encompasses a process for the preparation of Form 11 of the present invention, said process comprising the crystallisation of said solid form from a solution of the tosylate salt of the compound of Formula A in a solvent or a mixture of solvents. Optionally, said solution of the tosylate salt of the compound of Formula A may be formed by adding p-toluenesulfonic acid to a solution or suspension of the compound of Formula A in a solvent or a mixture of solvents. Preferably, the solvent is ethyl acetate, THF, acetone or acetonitrile. More preferably, the solvent is acetone. The crystallisation may be performed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours. The solvent or mixture of solvents may be removed by decanting off the solvent or mixture of solvents, and/or by evaporation of the solvent or mixture of solvents under a stream of inert gas, preferably under a stream of nitrogen.

The present invention also encompasses a process for the preparation of Form 12 of the present invention, said process comprising the crystallisation of said solid form from a solution of the edisylate salt of the compound of Formula A in a solvent or a mixture of solvents. Optionally, said solution of the edisylate salt of the compound of Formula A may be formed by adding 1,2-ethanedisulfonic acid to a solution or suspension of the compound of Formula A in a solvent or a mixture of solvents. Preferably, the solvent is ethyl acetate, THF, acetone or acetonitrile. More preferably, the solvent is acetonitrile. The crystallisation may be performed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours. The solvent or mixture of solvents may be removed by decanting off the solvent or mixture of solvents, and/or by evaporation of the solvent or mixture of solvents under a stream of inert gas, preferably under a stream of nitrogen.

The present invention also encompasses a process for the preparation of Form 13 of the present invention, said process comprising the crystallisation of said solid form from a solution of the besylate salt of the compound of Formula A in a solvent or a mixture of solvents. Optionally, said solution of the besylate salt of the compound of Formula A may be formed by adding benzenesulfonic acid to a solution or suspension of the compound of Formula A in a solvent or a mixture of solvents. Preferably, the solvent is ethyl acetate, THF, acetone or acetonitrile. More preferably, the solvent is acetone. The crystallisation may be performed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours. The solvent or mixture of solvents may be removed by decanting off the solvent or mixture of solvents, and/or by evaporation of the solvent or mixture of solvents under a stream of inert gas, preferably under a stream of nitrogen.

The present invention also encompasses a process for the preparation of Form 14 of the present invention, said process comprising the crystallisation of said solid form from a solution of the compound of Formula A in a solvent or a mixture of solvents. The solvent or mixture of solvents may comprise acetonitrile. Preferably, the solvent is acetonitrile. After adding the compound of Formula A to a solvent or a mixture of solvents (e.g. acetonitrile), the combined mixture (compound plus solvent(s)) may be heated to a temperature of approximately 60-85° C. Alternatively, the combined mixture may be heated to a temperature of approximately 70-85° C. Alternatively, the combined mixture may be heated to a temperature of approximately 75-80° C. Alternatively, the combined mixture may be heated to a temperature of approximately 75, 76, 77, 78, 79 or 80° C. Alternatively, the combined mixture may be heated to a temperature of approximately 79° C. Alternatively, the combined mixture may be heated to reflux. Following heating, the combined mixture may be held at a temperature of approximately 45-60° C. for a period of 20 to 40 mins, in particular approximately 30 minutes, while stirring. Alternatively, the combined mixture may be held at a temperature of approximately 50-55° C. for a period of 20 to 40 minutes, in particular approximately 30 minutes, while stirring. After this, the combined mixture may be cooled. Alternatively, the combined mixture may be cooled to a temperature of approximately 0-40° C. Alternatively, the combined mixture may be cooled to a temperature of approximately 10-30° C. Alternatively, the combined mixture may be cooled to room temperature. Alternatively, the combined mixture may be cooled to approximately 0° C. Seeds of a solid form of the invention, for example Form 1 or Form 14, in particular Form 14, may be added to the combined mixture during or after cooling. The solvent or mixture of solvents may be removed by filtering off the solvent or mixture of solvents or by decanting off the solvent or mixture of solvents, and/or by evaporation of the solvent or mixture of solvents under a stream of inert gas, preferably under a stream of nitrogen.

The present invention also encompasses a process for the preparation of Form 15 of the present invention, said process comprises the crystallisation of said solid form from a solution of the hydrochloride salt of the Compound of Formula A in a solvent or a mixture of solvents. Optionally, said solution of the hydrochloride salt of the compound of Formula A may be formed by adding hydrochloric acid to a solution or suspension of the compound of Formula A in a solvent or mixture of solvents. Preferably, the solvent is ethanol, methanol, isopropanol, acetone, methyl ethyl ketone, THF, or acetonitrile. Preferably, the solvent is ethanol, methanol, isopropanol or acetonitrile. More preferably, the solvent is acetonitrile. The crystallisation may be performed by temperature cycling of the combined mixture. The temperature cycling may comprise cycling the temperature of the combined mixture between about 30-50° C. and ambient temperature, optionally between 40° C. and ambient temperature. Preferably, the temperature cycling is carried out for between about 18 to about 24 hours. Alternatively the crystallisation may be performed by slow cooling of the combined mixture beginning at approximately 65° C. and cooling at 10° C. over between 1 to 48 hours, alternatively between over between 6 and 24 hours, alternatively over between 10 and 20 hours, alternatively over about 16 hrs. The mixture may be cooled to a temperature of approximately 0-40° C. Alternatively, the combined mixture may be cooled to a temperature of approximately 10-30° C. Alternatively, the combined mixture may be cooled to room temperature. Alternatively, the combined mixture may be cooled to approximately 0° C. Alternatively, the combined mixture may be cooled to approximately 10° C. The solvent or mixture of solvents may be removed by filtering off the solvent or mixture of solvents, or by decanting off the solvent or mixture of solvents, and/or by evaporation of the solvent or mixture of solvents under a stream of inert gas, or under vacuum, preferably under a stream of nitrogen.

The processes of the present invention may also comprise an additional step wherein the solution of the compound of Formula A or solution of a salt of a compound of Formula A in a solvent or a mixture of solvents is filtered prior to crystallisation.

The processes of the present invention may also comprise the addition of crystalline seeds of the solid form of the invention.

In an aspect, the present invention provides the solid form of the invention when manufactured by a process according to the invention.

As previously mentioned, the solid form of the present invention has a number of therapeutic applications, particularly in the treatment of diseases or conditions mediated by plasma kallikrein.

Accordingly, the present invention provides a solid form of the compound of Formula A and salts thereof, as hereinbefore defined, for use in therapy. In a preferred embodiment, the solid form is Form 1. In an alternative preferred embodiment, the solid form is Form 14. In an alternative preferred embodiment, the solid form is Form 5 of the hydrochloride salt of the compound of Formula A. In a further alternative preferred embodiment, the solid form is Form 15 of the hydrochloride salt of the compound of Formula A.

The present invention also provides for the use of a solid form of the compound of Formula A and salts thereof, as hereinbefore defined, in the manufacture of a medicament for the treatment of a disease or condition mediated by plasma kallikrein. In a preferred embodiment, the solid form is Form 1. In an alternative preferred embodiment, the solid form is Form 14. In an alternative preferred embodiment, the solid form is Form 5 of the hydrochloride salt of the compound of Formula A. In a further alternative preferred embodiment, the solid form is Form 15 of the hydrochloride salt of the compound of Formula A.

The present invention also provides a solid form of the compound of Formula A and salts thereof, as hereinbefore defined, for use in a method of treatment of a disease or condition mediated by plasma kallikrein. In a preferred embodiment, the solid form is Form 1. In an alternative preferred embodiment, the solid form is Form 14. In an alternative preferred embodiment, the solid form is Form 5 of the hydrochloride salt of the compound of Formula A. In a further alternative preferred embodiment, the solid form is Form 15 of the hydrochloride salt of the compound of Formula A.

The present invention also provides a method of treatment of a disease or condition mediated by plasma kallikrein, said method comprising administering to a mammal in need of such treatment a therapeutically effective amount of a solid form of the compound of Formula A and salts thereof, as hereinbefore defined. In a preferred embodiment, the solid form is Form 1. In an alternative preferred embodiment, the solid form is Form 14. In an alternative preferred embodiment, the solid form is Form 5 of the hydrochloride salt of the compound of Formula A. In a further alternative preferred embodiment, the solid form is Form 15 of the hydrochloride salt of the compound of Formula A.

In an aspect, the disease or condition mediated by plasma kallikrein is selected from impaired visual acuity, diabetic retinopathy, retinal vascular permeability associated with diabetic retinopathy, diabetic macular edema, hereditary angioedema, retinal vein occlusion, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery, and bleeding from post-operative surgery. In a preferred embodiment, the disease or condition mediated by plasma kallikrein is diabetic macular edema. In another preferred embodiment, the disease or condition mediated by plasma kallikrein is hereditary angioedema.

Alternatively, the disease or condition mediated by plasma kallikrein may be selected from retinal vascular permeability associated with diabetic retinopathy, diabetic macular edema and hereditary angioedema. Alternatively, the disease or condition mediated by plasma kallikrein may be retinal vascular permeability associated with diabetic retinopathy or diabetic macular edema. The solid forms of the compound of Formula A and salts thereof may be administered in a form suitable for injection into the ocular region of a patient, in particular, in a form suitable for intra-vitreal injection.

In the context of the present invention, references herein to "treatment" include references to curative, palliative and prophylactic treatment, unless there are specific indications to the contrary. The terms "therapy", "therapeutic" and "therapeutically" should be construed in the same way.

The solid form of the present invention may be administered alone or in combination with one or more other drugs. Generally, it will be administered as a formulation in association with one or more pharmaceutically acceptable excipients. The term "excipient" is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

In another aspect, the compounds of the present invention may be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema". Ophthalmology. 27 Apr. 2010).

Pharmaceutical compositions suitable for the delivery of the solid form of the present invention and methods for their preparation will be readily apparent to those skilled in the art. Such compositions and methods for their preparation may be found, for example, in Remington's Pharmaceutical Sciences, 19th Edition (Mack Publishing Company, 1995).

For administration to human patients, the total daily dose of the solid form of the invention is typically in the range 0.1 mg and 10,000 mg, or between 1 mg and 5000 mg, or between 10 mg and 1000 mg depending, of course, on the mode of administration. If administered by intra-vitreal injection a lower dose of between 0.0001 mg (0.1 μg) and 0.2 mg (200 μg) per eye is envisaged, or between 0.0005 mg (0.5 μg) and 0.05 mg (50 μg) per eye.

The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Accordingly, the present invention provides a pharmaceutical composition comprising a solid form of the compound of Formula A, as hereinbefore defined, and a pharmaceutically acceptable carrier, diluent and/or excipient. In a preferred embodiment, the solid form is Form 1. In an alternative preferred embodiment, the solid form is Form 14. In an alternative preferred embodiment, the solid form is Form 5 of the hydrochloride salt of the compound of Formula A. In a further alternative preferred embodiment, the solid form is Form 15 of the hydrochloride salt of the compound of Formula A.

It will be appreciated that the reference to solid forms of the compound of Formula A as hereinbefore defined includes both the free base and the salts thereof which have hereinbefore been described.

The pharmaceutical compositions may be administered topically (e.g. to the eye, to the skin or to the lung and/or airways) in the form, e.g., of eye-drops, creams, solutions, suspensions, heptafluoroalkane (HFA) aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally. In a further embodiment, the pharmaceutical composition is in the form of a suspension, tablet, capsule, powder, granule or suppository.

In an embodiment of the invention, the active ingredient is administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Liquid (including multiple phases and dispersed systems) formulations include emulsions, suspensions, solutions, syrups and elixirs. Such formulations may be presented as fillers in soft or hard capsules. Liquid formulations may also be prepared by the reconstitution of a solid, for example, from a sachet.

The solid form of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

The invention will now be illustrated by the following non-limiting examples. In the examples the following figures are presented:

GENERAL EXPERIMENTAL DETAILS

In the following examples, the following abbreviations and definitions are used:

| | |
|---|---|
| Aq | Aqueous solution |
| DCM | Dichloromethane |
| DMF | N,N-Dimethylformamide |
| DMSO | Dimethyl sulfoxide |
| DSC | Differential Scanning Calorimetry |
| EtOAc | Ethyl Acetate |

-continued

| | |
|---|---|
| HATU | 2-(3H-[1,2,3]triazolo[4,5-b]pyridin-3-yl)-1,1,3,3-tetramethylisouronium hexafluorophosphate(V) |
| Hrs | Hours |
| HOBt | Hydroxybenzotriazole |
| IPA | 2-Propanol/Propan-2-ol/Iso-propanol |
| LCMS | Liquid chromatography mass spectrometry |
| Me | Methyl |
| MeCN | Acetonitrile |
| MeOH | Methanol |
| Min | Minutes |
| MS | Mass spectrum |
| NMR | Nuclear magnetic resonance spectrum-NMR spectra were recorded at a frequency of 400 MHz unless otherwise indicated |
| Pet. Ether | Petroleum ether fraction boiling at 60-80° C. |
| Ph | Phenyl |
| STA | Simultaneous Thermal Analysis |
| SWFI | Sterile water for injection |
| rt | room temperature |
| THF | Tetrahydrofuran |
| TFA | Trifluoroacetic acid |
| XRPD | X-ray powder diffraction |

All reactions were carried out under an atmosphere of nitrogen unless specified otherwise.

$^1$H NMR spectra were recorded on a Bruker (400 MHz) or on a JEOL (400 MHz) spectrometer with reference to deuterium solvent and at rt.

Molecular ions were obtained using LCMS which was carried out using a Chromolith Speedrod RP-18e column, 50×4.6 mm, with a linear gradient 10% to 90% 0.1% $HCO_2H$/MeCN into 0.1% $HCO_2H/H_2O$ over 13 min, flow rate 1.5 mL/min, or using Agilent, X-Select, acidic, 5-95% MeCN/water over 4 min. Data was collected using a Thermofinnigan Surveyor MSQ mass spectrometer with electospray ionisation in conjunction with a Thermofinnigan Surveyor LC system.

Alternatively, molecular ions were obtained using LCMS which was carried out using an Agilent Poroshell 120 EC-C18 (2.7 m, 3.0×50 mm) column with 0.1% v/v Formic acid in water [eluent A]; MeCN [eluent B]; Flow rate 0.8 mL/min and 1.5 minutes equilibration time between samples, gradient shown below. Mass detection was afforded with API 2000 mass spectrometer (electrospray).

| Gradient: | | |
|---|---|---|
| Time (min) | Eluent A (%) | Eluent B (%) |
| 0.00 | 95 | 5 |
| 0.20 | 95 | 5 |
| 2.00 | 5 | 95 |
| 3.00 | 5 | 95 |
| 3.25 | 95 | 5 |
| 3.50 | 95 | 5 |

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Reverse phase preparative HPLC purifications were carried out using a Waters 2525 binary gradient pumping system at flow rates of typically 20 mL/min using a Waters 2996 photodiode array detector.

All solvents and commercial reagents were used as received.

Chemical names were generated using automated software such as the Autonom software provided as part of the ISIS Draw package from MDL Information Systems or the Chemaxon software provided as a component of MarvinSketch or as a component of the IDBS E-WorkBook.

Where stated, X-Ray Powder Diffraction patterns were collected on a Philips X-Pert MPD diffractometer and analysed using the following experimental conditions (Method A):

| Scan parameters: | |
|---|---|
| Scan Axis: | Gonio |
| Start Position [°2θ]: | 4.0084 |
| End Position [°2θ]: | 39.9804 |
| Step Size [°2θ]: | 0.0170 |
| Scan Step Time [s]: | 10.1600 |
| Scan Type: | Continuous |
| PSD Mode: | Scanning |
| PSD Length [°2θ]: | 2.12 |
| Offset [°2θ]: | 0.0000 |
| Divergence Slit Type: | Automatic |
| Irradiated Length [mm] | 10.00 |
| Specimen Length [mm]: | 10.00 |
| Measurement Temperature [° C.]: | 25.00 |
| Anode Material: | Cu |
| K-Alpha1 [Å]: | 1.54060 |
| K-Alpha2 [Å]: | 1.54443 |
| K-A2/K-A1 Ratio: | 0.50000 |
| Generator Settings: | 40 mA, 40 kV |
| Diffractometer Type: | 0000000011038600 |
| Diffractometer Number: | 0 |
| Goniometer Radius [mm]: | 240.00 |
| Dist. Focus-Diverg. Slit [mm]: | 100.00 |
| Incident Beam Monochromator: | No |
| Spinning: | Yes |

Approximately 5 mg of sample under analysis was gently compressed on the XRPD zero back ground single obliquely cut silica sample holder. The sample was then loaded into the diffractometer for analysis.

Simultaneous Thermal Analysis (STA) data were collected using the following method: Approximately 5 mg of sample was accurately weighed into a ceramic crucible and it was placed into the chamber of Perkin-Elmer STA 600 TGA/DTA analyzer at ambient temperature. The sample was then heated at a rate of 10° C./min, typically from 25° C. to 300° C., during which time the change in weight was monitored as well as DTA signal. The purge gas used was nitrogen at a flow rate of 20 $cm^3$/min.

Where specified, X-Ray Powder Diffraction patterns were collected using the following method (Method B):

According to Method B, X-ray powder diffraction studies were performed using a Bruker AXS D2 PHASER (D2-205355) in Bragg-Brentano configuration, equipment #2353. A Cu anode at 30 kV, 10 mA, sample stage standard rotating (5/min) with beam stop and monochromatisation by a Kβ-filter (0.59% Ni) were used. The slits that were used are fixed divergence slits 1.0 mm (=0.61°), primary axial Soller slit 2.5° and secondary axial Soller slit 2.5°. The detector is a linear detector LYNXEYE with receiving slit 5° detector opening. The standard sample holder (0.1 mm cavity in (510) silicon wafer) has a minimal contribution to the background signal. The measurement conditions were: scan range 5-45° 2θ, sample rotation 5 rpm, 0.5 s/step, 0.010°/step, 3.0 mm detector slit; and all measuring conditions were logged in the instrument control file. The software used for data collection was Diffrac.Commander v4.0. Data analysis was performed using Diffrac.Eva V4.1 evaluation software. No background correction or smoothing was applied to the patterns.

Where specified, X-Ray Powder Diffraction patterns were collected using the following method (Method C):

According to Method C, XRPD diffractograms were collected on a Bruker D8 diffractometer using Cu Kα radiation (40 kV, 40 mA) and a θ-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively. Samples were run under ambient conditions as flat plate specimens using powder as received. The sample was prepared on a polished, zero-background (510) silicon wafer by gently pressing onto the flat surface or packed into a cut cavity. The sample was rotated in its own plane. The details of the standard data collection method are:

Angular range: 2 to 42° 2θ
Step size: 0.05° 2θ
Collection time: 0.5 s/step (total collection time: 6.40 min)

Where specified, X-Ray Powder Diffraction patterns were collected using the following method (Method D):

According to Method D, XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel3D detector, placed on the diffracted beam, was fitted with a receiving slit and 0.04 rad Soller slits. The software used for data collection was X'Pert Data Collector using X'Pert Operator Interface. The data were analysed and presented using Diffrac Plus EVA or HighScore Plus.

Samples were prepared and analysed in a metal 96 well-plate in transmission mode. X-ray transparent film was used between the metal sheets and powders (approximately 1-2 mg) were used as received. The scan mode used the gonio scan axis.

The details of the standard screening data collection method are:

Angular range: 2.5 to 32.0° 2θ
Step size: 0.0130° 2θ
Collection time: 12.75 s/step (total collection time of 2.07 min)

Thermogravimetric Analysis (TGA) data were collected using the following method: Approximately 5-10 mg of sample was accurately weighed into a pre-tared aluminium DSC pan and it was placed into the chamber of a TA Instruments Q500 TGA equipped with a 16 position auto-sampler at ambient temperature. The sample was then heated from ambient temperature to 350° C. at a rate of 10° C./min, during which time the change in weight was monitored. Nitrogen was used as a purge gas at a flow rate of 60 ml/min. The instrument control software was Advantage for Q Series and Thermal Advantage and the data were analysed using Universal Analysis.

Differential Scanning Calorimetry (DSC) data were collected using the following method: Approximately 0.5-3 mg of sample was accurately weighted into a pin-holed aluminium DSC pan and it was placed into the chamber of a TA Instruments Discovery DSC equipped with a 50 position auto-sampler at ambient temperature. The sample was then heated from 25° C. to 250° C. at a rate of 10° C./min. The purge gas used was nitrogen at a flow rate of 50 ml/min over the sample.

The instrument control software was TRIOS and the data were analysed using Universal Analysis.

Where specified Differential Scanning Calorimetry (DSC) data were collected using a Mettler Toledo DSC1 STARe System (Method D). Typically 5-10 mg of sample was loaded onto a pre-weighed Al crucible and kept at 20° C. for 5 minutes, after which it was heated at 10° C./min from 20° C. to 350° C. and kept at 350° C. for 1 minute. A nitrogen purge of 40 ml/min was maintained over the sample. The software used for data collection and evaluation was STARe Software v15.0.

SYNTHETIC EXAMPLES

Example 1—Form 1 of 1-({4-[(5-fluoro-2-oxopyridin-1-yl)methyl]phenyl}methyl)-N-[(3-fluoro-4-methoxypyridin-2-yl)methyl]-3-(methoxymethyl) pyrazole-4-carboxamide 5-Fluoro-1-(4-hydroxymethyl-benzyl)-1H-pyridin-2-one

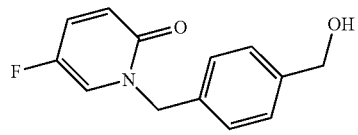 [SMILES: O=c1ccc(F)cn1Cc1ccc(CO)cc1]

To 4-(chloromethyl)benzylalcohol (4.50 g, 28.7 mmol) in acetone (150 mL) was added 5-fluoro-2-hydroxypyridine (3.57 g, 31.6 mmol) and K$_2$CO$_3$ (11.9 g, 24.2 mmol) and the reaction mixture was stirred at 50° C. for 36 hrs. The reaction mixture was cooled and solvent was removed in vacuo. The residue was taken up in CHCl$_3$ (150 mL) and washed with water (30 mL), dried (Na$_2$SO$_4$), filtered and evaporated. The aqueous layer was extracted with 20% IPA-chloroform (3×50 mL). All organic layers were combined. The residue was adsorbed onto silica and purified by automated flash chromatography eluting with MeOH-DCM, to give a white solid identified as the title compound (5.65 g, 24.2 mmol, 84%).

[M+H]$^+$=234.2

1-(4-Bromomethyl-benzyl)-5-fluoro-1H-pyridin-2-one

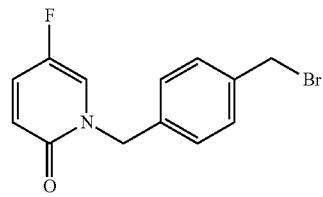 [SMILES: O=c1ccc(F)cn1Cc1ccc(CBr)cc1]

To 5-fluoro-1-(4-hydroxymethyl-benzyl)-1H-pyridin-2-one (1.65 g, 7.1 mmol) in DCM (100 mL) was added phosphorous tribromide (665 mL, 7.1 mmol) and the reaction stirred at rt for 2 hrs. The reaction mixture was diluted with CHCl$_3$ (100 mL) and washed with saturated NaHCO$_3$ (aq) (50 mL), water (10 mL) and brine (10 mL). The organic layer was dried (Na$_2$SO$_4$), filtered and evaporated to give a colourless gum identified as the title compound which was used without further purification (1.85 g, 6.3 mmol, 88%).

[M+Na]$^+$=318.2

1-[4-(5-Fluoro-2-oxo-2H-pyridin-1-ylmethyl)-benzyl]-3-methoxymethyl-1H-pyrazole-4-carboxylic acid methyl ester

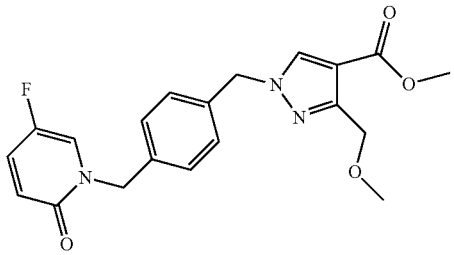 [SMILES: COCc1nn(Cc2ccc(Cn3cc(F)ccc3=O)cc2)cc1C(=O)OC]

To 3-methoxymethyl-1H-pyrazole-4-carboxylic acid methyl ester (259 mg, 1.5 mmol) in DMF (2 mL) was added 1-(4-bromomethyl-benzyl)-5-fluoro-1H-pyridin-2-one (450 mg, 1.5 mmol) and K$_2$CO$_3$ (420 mg, 3.04 mmol). The reaction mixture was stirred at rt for 18 hrs. The reaction mixture was concentrated and then partitioned between EtOAc (60 mL) and water (20 mL) and washed sequentially with water (3×10 mL) and brine (10 mL). The organic layer was dried (Na$_2$SO$_4$), filtered and evaporated. The crude residue was purified by automated flash chromatography eluting with EtOAc/acetonitrile-methanol to give two regioisomers. The regioisomers were identified by $^1$H NOESY and the title compound isolated as an off-white solid (327 mg, 0.85 mmol, 55%).

[M+H]$^+$=385.8

$^1$H NMR (CDCl$_3$) 3.49 (3H, s), 3.81 (3H, s), 4.74 (2H, s), 5.10 (2H, s), 5.30 (2H, s), 6.61 (1H, dd, J=10.4, 5.4 Hz), 7.16 (1H, t, J=3.5 Hz), 7.25-7.26 (2H, m), 7.29-7.33 (3H, m), 7.81 (1H, s)

1-[4-(5-Fluoro-2-oxo-2H-pyridin-1-ylmethyl)-benzyl]-3-methoxymethyl-1H-pyrazole-4-carboxylic acid

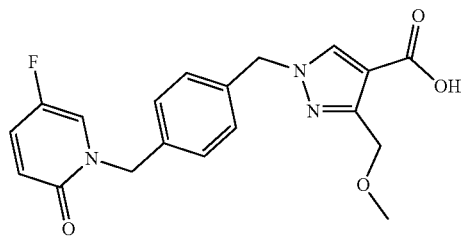 [SMILES: COCc1nn(Cc2ccc(Cn3cc(F)ccc3=O)cc2)cc1C(=O)O]

To 1-[4-(5-fluoro-2-oxo-2H-pyridin-1-ylmethyl)-benzyl]-3-methoxymethyl-1H-pyrazole-4-carboxylic acid methyl ester (327 mg, 0.85 mmol) in ethanol (50 mL) was added NaOH (339 mg, 8.5 mmol) and heated at vigorous reflux for 24 hrs. The reaction mixture was cooled and concentrated. The crude residue was diluted with water (5 mL) and washed with DCM (7 mL). The aqueous phase was taken and adjusted to pH 2 with 2M HCl and then extracted with 90% CH$_3$Cl/10% IPA (6×15 mL). The organic layer was dried (Na$_2$SO$_4$), filtered and concentrated to give a pale yellow solid that was used without further purification.

3-Fluoro-4-methoxy-pyridine-2-carbonitrile

To a large microwave vial, cyanocopper (1.304 g, 14.6 mmol) was added to a solution of 2-bromo-3-fluoro-4-methoxypyridine (1 g, 4.9 mmol) in DMF (5 mL). The reaction vial was sealed and heated to 100° C. for 16 hrs. The reaction mixture was diluted with water (20 mL) and EtOAc (20 mL). The thick suspension was sonicated and required additional water (40 mL) and EtOAc (2×50 mL) with sonication to break-up the solid precipitated. The combined layers were filtered through a plug of Celite and the organic layer isolated, washed with brine (50 mL), dried over MgSO$_4$, filtered and the solvent removed under reduced pressure to give a pale green solid identified as 3-fluoro-4-methoxy-pyridine-2-carbonitrile (100 mg, 0.58 mmol, 12% yield)

(3-Fluoro-4-methoxy-pyridin-2-ylmethyl)-carbamic acid tert-butyl ester

3-Fluoro-4-methoxy-pyridine-2-carbonitrile (100 mg, 0.58 mmol) was dissolved in anhydrous MeOH (10 mL, 247 mmol) and nickel chloride hexahydrate (14 mg, 0.058 mmol) was added followed by di-tert-butyl dicarbonate (255 mg, 1.16 mmol). The resulting pale green solution was cooled in an ice-salt bath to −5° C. and then sodium borohydride (153 mg, 4.1 mmol) was added portionwise maintaining the reaction temperature 0° C. The deep brown solution was left to stir at 0° C. and slowly allowed to warm to rt and then left to stir at rt for 3 hrs. The reaction mixture was evaporated to dryness at 40° C. to afford a black residue which was diluted with DCM (10 mL) and washed with sodium hydrogen carbonate (aq) (10 mL). An emulsion formed so the organics were separated via a phase separating cartridge and concentrated. The crude liquid was purified by chromatography eluting with EtOAc/iso-hexane to afford (3-fluoro-4-methoxy-pyridin-2-ylmethyl)-carbamic acid tert-butyl ester as a clear yellow oil (108 mg, 62% yield)
[MH]$^+$=257

(3-Fluoro-4-methoxy-pyridin-2-yl)-methylamine dihydrochloride salt (3-Fluoro-4-methoxy-pyridin-2-ylmethyl)-carbamic acid tert-butyl ester (108 mg, 0.36 mmol) was taken up in iso-propyl alcohol (1 mL) and then HCl (6N in iso-propyl alcohol) (1 mL, 0.58 mmol) was added at rt and left to stir at 40° C. for 2 hrs. The reaction mixture was concentrated under reduced pressure and then triturated with diethyl ether and sonicated to give a cream coloured solid (75 mg, 55% yield) identified as (3-fluoro-4-methoxy-pyridin-2-yl)-methylamine dihydrochloride salt. [MH]$^+$=157

Form 1 of 1-({4-[(5-fluoro-2-oxopyridin-1-yl)methyl]phenyl}methyl)-N-[(3-fluoro-4-methoxy-pyridin-2-yl)methyl]-3-(methoxymethyl)pyrazole-4-carboxamide

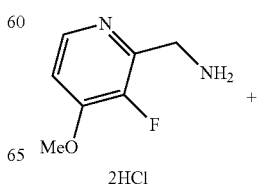

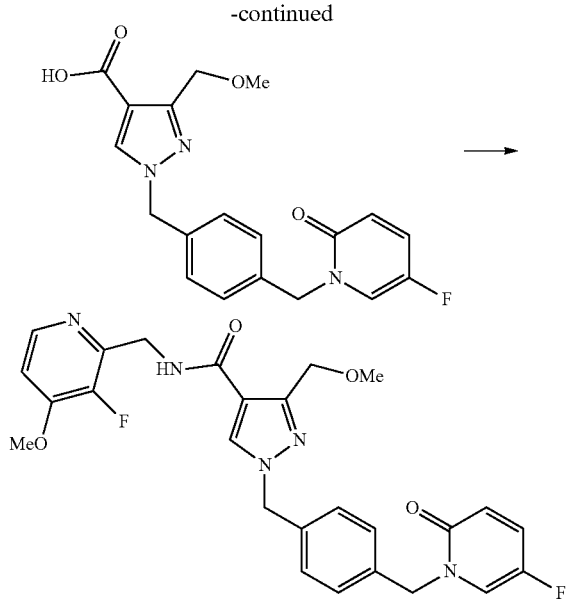

1,1'-Carbonyldiimidazole (8.45 g, 52.1 mmol) was added to a solution of 1-(4-((5-fluoro-2-oxopyridin-1(2H)-yl)methyl)benzyl)-3-(methoxymethyl)-1H-pyrazole-4-carboxylic acid (19.4 g, 52.1 mmol) in DMF (112 mL) and the reaction mixture was heated to 50° C. for 2 hrs. After that time, (3-fluoro-4-methoxypyridin-2-yl)methanamine dihydrochloride (12.0 g, 52.1 mmol) was added to the reaction mixture and heating at 50° C. was continued overnight. The reaction mixture was cooled to rt then added dropwise to water (1 L) with vigorous stirring. After addition was completed stirring was continued for 1 hour. The product was collected by filtration and was washed with water (250 mL). The wet material was dissolved in DCM and water was separated. The organic layer was dried over $Na_2SO_4$ and filtered through Celite. The solvent was removed in vacuo to yield 21.9 g.

The residue was recrystallized from IPA (170 mL) at reflux, cooling to rt before filtering, then twice taken up into DCM, washed with sodium bicarbonate (aq), dried over $Na_2SO_4$, filtered and concentrated under reduced pressure. The residue was recrystallized from IPA (160 mL) at reflux, cooling to rt before filtering. Trituration with cold tert-butyl methyl ether and drying gave Form 1 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide (17 g).

$^1$H NMR (400 Mhz, d6-DMSO) δ 3.17 (3H, s), 3.83 (3H, s), 4.42 (2H s), 4.44 (2H, d, J=3.2 Hz), 4.92 (2H, s), 5.19 (2H, s), 6.35 (1H, dd, J=10.0, 5.5 Hz), 7.09 (1H, t, J=6.0 Hz), 7.14 (2H, d, J=8.2 Hz), 7.20 (2H, d, J=8.21H z), 7.46-7.51 (1H, m), 7.92 (1H, t, J=0.91H z), 8.14 (1H, d, J=5.51H z), 8.17 (1H, s), 8.34 (1H, t, J=5.3 Hz) ppm.

An XRPD diffractogram (Method A) of Form 1 is shown in FIG. 1.

Peak position table:

| No. | Pos. [°2θ] | Height [cts] | Rel. Int. [%] |
|---|---|---|---|
| 1 | 7.7 | 290.2 | 12.1 |
| 2 | 8.3 | 91.1 | 3.8 |
| 3 | 10.7 | 34.0 | 1.4 |
| 4 | 11.6 | 385.3 | 16.1 |
| 5 | 12.6 | 247.8 | 10.3 |
| 6 | 12.8 | 139.4 | 5.8 |
| 7 | 13.7 | 39.4 | 1.6 |
| 8 | 14.1 | 48.2 | 2.0 |
| 9 | 14.7 | 1090.1 | 45.4 |
| 10 | 15.2 | 200.8 | 8.4 |
| 11 | 15.5 | 112.2 | 4.7 |
| 12 | 16.4 | 54.7 | 2.3 |
| 13 | 17.1 | 193.3 | 8.1 |
| 14 | 17.6 | 409.3 | 17.1 |
| 15 | 17.9 | 1246.2 | 52.0 |
| 16 | 18.1 | 1785.6 | 74.4 |
| 17 | 19.4 | 1386.7 | 57.8 |
| 18 | 20.1 | 2398.9 | 100.0 |
| 19 | 20.8 | 583.3 | 24.3 |
| 20 | 21.4 | 1207.4 | 50.3 |
| 21 | 22.1 | 567.3 | 23.7 |
| 22 | 22.5 | 1106.6 | 46.1 |
| 23 | 23.4 | 925.6 | 38.6 |
| 24 | 23.9 | 567.5 | 23.7 |
| 25 | 24.2 | 362.1 | 15.1 |
| 26 | 24.5 | 375.2 | 15.6 |
| 27 | 25.3 | 563.5 | 23.5 |
| 28 | 26.0 | 404.1 | 16.9 |
| 29 | 26.8 | 448.1 | 18.7 |
| 30 | 27.2 | 229.3 | 9.6 |
| 31 | 28.3 | 183.9 | 7.7 |
| 32 | 29.2 | 413.8 | 17.3 |
| 33 | 29.6 | 441.4 | 18.4 |
| 34 | 30.2 | 159.3 | 6.6 |
| 35 | 31.3 | 250.7 | 10.5 |
| 36 | 32.2 | 198.3 | 8.3 |
| 37 | 33.6 | 175.8 | 7.3 |
| 38 | 34.7 | 169.1 | 7.1 |
| 39 | 37.0 | 83.7 | 3.5 |
| 40 | 38.1 | 77.8 | 3.2 |
| 41 | 38.6 | 48.5 | 2.0 |

Simultaneous Thermal Analysis (STA)
The STA data for Form 1 are shown in FIG. 2.

Example 2—Form 2 of 1-({4-[(5-fluoro-2-oxopyridin-1-yl)methyl]phenyl}methyl)-N-[(3-fluoro-4-methoxypyridin-2-yl)methyl]-3-(methoxymethyl) pyrazole-4-carboxamide 1-({4-[(5-Fluoro-2-oxopyridin-1-yl)methyl]phenyl}methyl)-N-[(3-fluoro-4-methoxypyridin-2-yl)methyl]-3-(methoxymethyl)pyrazole-4-carboxamide was dissolved in 1:1 MeOH/water, with heating, to provide a 200 mg/mL solution. The solvent was allowed to evaporate under nitrogen to afford Form 2 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide.

An XRPD diffractogram (Method A) of Form 2 is shown in FIG. 3.

Peak position table:

| No. | Pos. [°2θ] | Height [cts] | Rel. Int. [%] |
|---|---|---|---|
| 1 | 5.7 | 200.7 | 54.3 |
| 2 | 7.5 | 29.5 | 8.0 |
| 3 | 9.9 | 134.5 | 36.4 |
| 4 | 13.0 | 369.8 | 100.0 |
| 5 | 15.0 | 205.4 | 55.5 |
| 6 | 16.0 | 75.7 | 20.5 |

-continued

Peak position table:

| No. | Pos. [°2θ] | Height [cts] | Rel. Int. [%] |
|---|---|---|---|
| 7 | 17.2 | 103.0 | 27.9 |
| 8 | 17.7 | 42.2 | 11.4 |
| 9 | 18.6 | 54.8 | 14.8 |
| 10 | 19.6 | 57.8 | 15.6 |
| 11 | 22.2 | 203.4 | 55.0 |
| 12 | 23.1 | 140.3 | 37.9 |
| 13 | 25.0 | 32.0 | 8.7 |
| 14 | 25.7 | 72.2 | 19.5 |
| 15 | 28.8 | 49.6 | 13.4 |

Example 3—Form 3 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide 1-({4-[(5-Fluoro-2-oxopyridin-1-yl)methyl]phenyl}methyl)-N-[(3-fluoro-4-methoxypyridin-2-yl)methyl]-3-(methoxymethyl)pyrazole-4-carboxamide (10 mg) was added to EtOH (50 µL) and the mixture heated until the solid had dissolved. The warm solution was then cooled rapidly by plunging into liquid nitrogen. The solvent was then evaporated under a flow of nitrogen to afford Form 3 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide.

An XRPD diffractogram (Method A) of Form 3 is shown in FIG. 4.

Peak position table:

| No. | Pos. [°2θ] | Height [cts] | Rel. Int. [%] |
|---|---|---|---|
| 1 | 4.7 | 18.7 | 2.2 |
| 2 | 5.3 | 16.8 | 2.0 |
| 3 | 7.0 | 848.9 | 100.0 |
| 4 | 9.5 | 147.1 | 17.3 |
| 5 | 10.3 | 166.1 | 19.6 |
| 6 | 10.8 | 108.6 | 12.8 |
| 7 | 11.4 | 68.6 | 8.1 |
| 8 | 12.0 | 68.0 | 8.0 |
| 9 | 13.0 | 18.4 | 2.2 |
| 10 | 14.1 | 246.1 | 29.0 |
| 11 | 15.0 | 70.5 | 8.3 |
| 12 | 16.0 | 65.6 | 7.7 |
| 13 | 16.3 | 170.5 | 20.1 |
| 14 | 17.2 | 71.3 | 8.4 |
| 15 | 17.8 | 100.7 | 11.9 |
| 16 | 18.2 | 260.7 | 30.7 |
| 17 | 18.6 | 71.3 | 8.4 |
| 18 | 19.8 | 64.9 | 7.6 |
| 19 | 20.2 | 103.0 | 12.1 |
| 20 | 20.9 | 53.3 | 6.3 |
| 21 | 21.5 | 85.4 | 10.1 |
| 22 | 22.4 | 96.6 | 11.4 |
| 23 | 23.4 | 167.3 | 19.7 |
| 24 | 24.1 | 344.1 | 40.5 |
| 25 | 24.4 | 235.3 | 27.7 |
| 26 | 25.3 | 379.9 | 44.8 |
| 27 | 25.6 | 182.6 | 21.5 |
| 28 | 26.2 | 141.3 | 16.6 |
| 29 | 26.7 | 92.0 | 10.8 |
| 30 | 28.0 | 71.8 | 8.5 |
| 31 | 29.9 | 41.2 | 4.9 |
| 32 | 33.1 | 17.9 | 2.1 |
| 33 | 35.8 | 13.7 | 1.6 |

Example 4—Form 4 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide A slurry of 1-({4-[(5-Fluoro-2-oxopyridin-1-yl)methyl]phenyl}methyl)-N-[(3-fluoro-4-methoxypyridin-2-yl)methyl]-3-(methoxymethyl)pyrazole-4-carboxamide (10 mg) in 90:10 IPA/water (50 µL) was prepared. The slurry was matured by temperature-cycling for 2 days by shaking on a platform whilst the atmospheric temperature was raised to 40° C. for four hrs then switching off the power to the heater/incubator for four hrs then repeating the temperature cycle in this manner up to 2 days.

The solvent was then evaporated, at ambient temperature, under a flow of nitrogen to afford Form 4 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide.

An XRPD diffractogram (Method A) of Form 4 is shown in FIG. 5.

Peak position table:

| No. | Pos. [°2θ] | Height [cts] | Rel. Int. [%] |
|---|---|---|---|
| 1 | 4.8 | 3604.2 | 100.0 |
| 2 | 7.8 | 193.9 | 5.4 |
| 3 | 9.5 | 404.2 | 11.2 |
| 4 | 10.3 | 66.7 | 1.9 |
| 5 | 11.0 | 1004.9 | 27.9 |
| 6 | 11.7 | 214.9 | 6.0 |
| 7 | 12.7 | 118.00 | 3.3 |
| 8 | 12.9 | 33.6 | 0.9 |
| 9 | 14.3 | 721.1 | 20.0 |
| 10 | 14.8 | 230.6 | 6.4 |
| 11 | 15.3 | 441.1 | 12.2 |
| 12 | 15.6 | 91.3 | 2.5 |
| 13 | 15.9 | 248.9 | 6.9 |
| 14 | 17.1 | 76.6 | 2.1 |
| 15 | 17.7 | 61.6 | 1.7 |
| 16 | 18.0 | 133.2 | 3.7 |
| 17 | 18.2 | 271.7 | 7.5 |
| 18 | 18.8 | 123.2 | 3.4 |
| 19 | 19.1 | 93.0 | 2.6 |
| 20 | 19.5 | 274.4 | 7.6 |
| 21 | 19.9 | 242.7 | 6.7 |
| 22 | 20.2 | 423.6 | 11.8 |
| 23 | 20.7 | 98.9 | 2.7 |
| 24 | 21.5 | 266.1 | 7.4 |
| 25 | 22.0 | 160.8 | 4.5 |
| 26 | 22.2 | 367.3 | 10.2 |
| 27 | 22.6 | 190.6 | 5.3 |
| 28 | 23.2 | 146.2 | 4.1 |
| 29 | 23.5 | 138.14 | 3.8 |
| 30 | 24.0 | 352.2 | 9.8 |
| 31 | 24.6 | 128.63 | 3.6 |
| 32 | 25.4 | 202.1 | 5.6 |
| 33 | 26.1 | 95.8 | 2.7 |
| 34 | 26.3 | 50.5 | 1.4 |
| 35 | 26.8 | 229.8 | 6.4 |
| 36 | 27.2 | 64.2 | 1.8 |
| 37 | 27.8 | 49.4 | 1.4 |
| 38 | 28.4 | 95.2 | 2.6 |
| 39 | 29.2 | 151.5 | 4.2 |
| 40 | 29.8 | 68.0 | 1.9 |
| 41 | 31.1 | 53.1 | 1.5 |
| 42 | 31.4 | 57.8 | 1.6 |
| 43 | 32.4 | 36.9 | 1.0 |
| 44 | 33.0 | 36.4 | 1.0 |
| 45 | 33.8 | 35.1 | 1.0 |
| 46 | 35.6 | 27.5 | 0.8 |
| 47 | 37.1 | 16.9 | 0.5 |
| 48 | 37.7 | 23.4 | 0.7 |
| 49 | 38.2 | 20.8 | 0.6 |
| 50 | 39.2 | 25.8 | 0.7 |

Example 5—Form 5 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide hydrochloride To 1-({4-[(5-fluoro-2-oxopyridin-1-yl)methyl]phenyl}methyl)-N-[(3-fluoro-4-methoxypyridin-2-yl)methyl]3-(methoxymethyl)pyrazole-4-carboxamide (15 mg) in THF (150 µL) was added 1.1 equivalents of 5M hydrochloric acid. The mixture was shaken well by hand, and the mixture temperature cycled between ambient and 40° C. for 18-24 hrs. The supernatant was decanted off, and the solid dried by evaporation under nitrogen to afford Form 5 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide hydrochloride.

An XRPD diffractogram (Method A) of Form 5 is shown in FIG. 6.

Form 5 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide hydrochloride was also formed by substituting the THF in the above procedure with acetone or acetonitrile.

Example 6—Form 6 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide hydrochloride To 1-({4-[(5-fluoro-2-oxopyridin-1-yl)methyl]phenyl}methyl)-N-[(3-fluoro-4-methoxypyridin-2-yl)methyl]3-(methoxymethyl)pyrazole-4-carboxamide (15 mg) in ethyl acetate (150 µL) was added 1.1 equivalents of 5 M hydrochloric acid. The mixture was shaken well by hand, and the mixture temperature cycled between ambient and 40° C. for 18-24 hrs. The solvent was allowed to evaporation under nitrogen to afford Form 6 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide hydrochloride.

An XRPD diffractogram (Method A) of Form 6 is shown in FIG. 7.

Example 7—Form 7 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide sulfate To 1-({4-[(5-fluoro-2-oxopyridin-1-yl)methyl]phenyl}methyl)-N-[(3-fluoro-4-methoxypyridin-2-yl)methyl]3-(methoxymethyl)pyrazole-4-carboxamide (15 mg) in acetone (150 µL) was added 1.1 equivalents of 6M sulfuric acid. The mixture was shaken well by hand, and the mixture temperature cycled between ambient and 40° C. for 18-24 hrs. The supernatant was decanted off, and the solid dried by evaporation under nitrogen to afford Form 7 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide sulfate.

An XRPD diffractogram (Method A) of Form 7 is shown in FIG. 8.

Form 7 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide sulfate was also formed by substituting the acetone in the above procedure with ethyl acetate, THF or acetonitrile.

Example 8—Form 8 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide phosphate To 1-({4-[(5-fluoro-2-oxopyridin-1-yl)methyl]phenyl}methyl)-N-[(3-fluoro-4-methoxypyridin-2-yl)methyl]3-(methoxymethyl)pyrazole-4-carboxamide (15 mg) in acetone (150 µL) was added 1.1 equivalents of 5M orthophosphoric acid. The mixture was shaken well by hand, and the mixture temperature cycled between ambient and 40° C. for 18-24 hrs. The supernatant was decanted off, and the solid dried by evaporation under nitrogen to afford Form 8 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide phosphate.

An XRPD diffractogram (Method A) of Form 8 is shown in FIG. 9.

Form 8 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide phosphate was also formed by substituting the acetone in the above procedure with acetonitrile.

Example 9—Form 9 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide mesylate To 1-({4-[(5-fluoro-2-oxopyridin-1-yl)methyl]phenyl}methyl)-N-[(3-fluoro-4-methoxypyridin-2-yl)methyl]3-(methoxymethyl)pyrazole-4-carboxamide (15 mg) in ethyl acetate (150 µL) was added 1.1 equivalents of methanesulfonic acid. The mixture was shaken well by hand, and the mixture temperature cycled between ambient and 40° C. for 18-24 hrs. The supernatant was decanted off, and the solid dried by evaporation under nitrogen to afford Form 9 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide mesylate.

An XRPD diffractogram (Method A) of Form 9 is shown in FIG. 10.

Form 9 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide mesylate was also formed by substituting the ethyl acetate in the above procedure with acetone.

Example 10—Form 10 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide mesylate To 1-({4-[(5-fluoro-2-oxopyridin-1-yl)methyl]phenyl}methyl)-N-[(3-fluoro-4-methoxypyridin-2-yl)methyl]3-(methoxymethyl)pyrazole-4-carboxamide (15 mg) in THF (150 µL) was added 1.1 equivalents of methanesulfonic acid. The mixture was shaken well by hand, and the mixture temperature cycled between ambient and 40° C. for 18-24 hrs. The supernatant was decanted off, and the solid dried by evaporation under nitrogen to afford Form 10 of 1-({4-[(5-fluoro-2-oxopyridin-1-yl)methyl]

phenyl}methyl)-N-[(3-fluoro-4-methoxypyridin-2-yl)methyl]-3-(methoxymethyl)pyrazole-4-carboxamide mesylate.

An XRPD diffractogram (Method A) of Form 10 is shown in FIG. 11.

Example 11—Form 11 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide tosylate To 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide (15 mg) in acetone (150 µL) was added 1.1 equivalents of p-toluenesulfonic acid. The mixture was shaken well by hand, and the mixture temperature cycled between ambient and 40° C. for 18-24 hrs. The supernatant was decanted off, and the solid dried by evaporation under nitrogen to afford Form 11 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide tosylate.

An XRPD diffractogram (Method A) of Form 11 is shown in FIG. 12.

Form 11 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide tosylate was also formed by substituting the acetone in the above procedure with ethyl acetate, THF or acetonitrile.

Example 12—Form 12 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide edisylate To 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide (15 mg) in acetonitrile (150 µL) was added 1.1 equivalents of 1,2-ethanedisulfonic acid. The mixture was shaken well by hand, and the mixture temperature cycled between ambient and 40° C. for 18-24 hrs. The supernatant was decanted off, and the solid dried by evaporation under nitrogen to afford Form 12 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide edisylate.

An XRPD diffractogram (Method A) of Form 12 is shown in FIG. 13.

Form 12 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide edisylate was also formed by substituting the acetonitrile in the above procedure with ethyl acetate, THF or acetone.

Example 13—Form 13 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide besylate To 1-({4-[(5-fluoro-2-oxopyridin-1-yl)methyl]phenyl}methyl)-N-[(3-fluoro-4-methoxypyridin-2-yl)methyl]3-(methoxymethyl)pyrazole-4-carboxamide (15 mg) in acetone (150 µL) was added 1.1 equivalents of benzenesulfonic acid (as a stock solution of benzenesulfonic acid (100 mg) in acetone (1 mL)). The mixture was shaken well by hand, and the mixture temperature cycled between ambient and 40° C. for 18-24 hrs. The supernatant was decanted off, and the solid dried by evaporation under nitrogen to afford Form 13 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide besylate.

An XRPD diffractogram (Method A) of Form 13 is shown in FIG. 14.

Form 13 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide besylate was also formed by substituting the acetone in the above procedure with ethyl acetate, THF or acetonitrile.

Example 14—Form 14 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide (200 g) in acetonitrile (2.35 kg) was stirred at 150 rpm and heated to 79° C. to yield a hazy solution. A polishing filtration was then performed. The resultant solution was maintained at a temperature of approximately 55° C. and seeded with Form 1 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide (1.01 g). Alternatively, the resultant solution could have been seeded with Form 14 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide. The resulting suspension was stirred for 30 mins at 50-55° C. before being cooled to 0-5° C. (at a rate of 0.5° C./min) and stirred for 30 mins. The solids were isolated by filtration, washed with cold (0-5° C.) acetonitrile and dried under vacuum to afford Form 14 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide.

An XRPD diffractogram (Method B) of Form 14 is shown in FIG. 15.

| Peak position table: | | | |
| --- | --- | --- | --- |
| No. | Pos. [°2θ] | Height [cts] | Rel. Int. [%] |
| 1 | 6.1 | 1350.0 | 3.3 |
| 2 | 9.6 | 1410.0 | 3.5 |
| 3 | 11.3 | 686.0 | 1.7 |
| 4 | 12.0 | 2050.0 | 5.1 |
| 5 | 12.2 | 5660.0 | 14.0 |
| 6 | 13.2 | 6890.0 | 17.0 |
| 7 | 14.2 | 1210.0 | 3.0 |
| 8 | 14.5 | 991.0 | 2.4 |
| 9 | 15.4 | 5740.0 | 14.2 |
| 10 | 16.8 | 446.0 | 1.1 |
| 11 | 18.0 | 20200.0 | 49.9 |
| 12 | 18.2 | 8280.0 | 20.4 |
| 13 | 18.6 | 3740.0 | 9.2 |
| 14 | 19.5 | 1560.0 | 3.9 |
| 15 | 20.7 | 12600.0 | 31.1 |
| 16 | 21.4 | 663.0 | 1.6 |
| 17 | 22.4 | 3440.0 | 8.5 |
| 18 | 23.2 | 40500.0 | 100.0 |
| 19 | 23.3 | 35300.0 | 87.2 |
| 20 | 24.2 | 19500.0 | 48.1 |
| 21 | 24.4 | 22800.0 | 56.3 |

Peak position table:

| No. | Pos. [°2θ] | Height [cts] | Rel. Int. [%] |
|---|---|---|---|
| 22 | 25.0 | 2450.0 | 6.0 |
| 23 | 25.7 | 10000.0 | 24.7 |
| 24 | 26.2 | 9560.0 | 23.6 |
| 25 | 26.6 | 1590.0 | 3.9 |
| 26 | 27.1 | 677.0 | 1.7 |
| 27 | 27.7 | 6300.0 | 15.6 |
| 28 | 28.3 | 4950.0 | 12.2 |
| 29 | 29.1 | 14000.0 | 34.6 |
| 30 | 29.9 | 903.0 | 2.2 |
| 31 | 30.5 | 5820.0 | 14.4 |
| 32 | 31.2 | 1320.0 | 3.3 |
| 33 | 32.2 | 855.0 | 2.1 |
| 34 | 33.3 | 1490.0 | 3.7 |
| 35 | 33.8 | 820.0 | 2.0 |
| 36 | 35.1 | 641.0 | 1.6 |
| 37 | 35.9 | 870.0 | 2.1 |
| 38 | 36.3 | 986.0 | 2.4 |
| 39 | 36.8 | 764.0 | 1.9 |
| 40 | 37.2 | 615.0 | 1.5 |
| 41 | 38.3 | 1140.0 | 2.8 |
| 42 | 39.3 | 230.0 | 0.6 |
| 43 | 39.7 | 781.0 | 1.9 |
| 44 | 41.3 | 750.0 | 1.9 |
| 45 | 42.3 | 467.0 | 1.2 |
| 46 | 43.2 | 573.0 | 1.4 |
| 47 | 43.4 | 693.0 | 1.7 |
| 48 | 44.5 | 383.0 | 0.9 |

Differential Scanning Calorimetry (DSC)
The DSC data for Form 14 are shown in FIG. 16.

Example 14A—Form 14 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide Form 5 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide hydrochloride (5.4 mg) was suspended in pH 7.4 citric acid-sodium phosphate buffer (0.5 mL) (prepared by transferring 0.1M citric acid solution (4.5 ml) to a 50 ml volumetric flask and making to volume with 0.2M disodium hydrogen phosphate). The suspension was shaken at 25° C./750 rpm for 24 hrs. The mixture was pH checked and adjusted periodically during the 24 hrs period with 0.2M NaOH to maintain within pH 7.4±0.1 range. The mixture was filtered and the residual solid was retained for XRPD. XRPD identified the solid residue as Form 14 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide.

Figure 17:
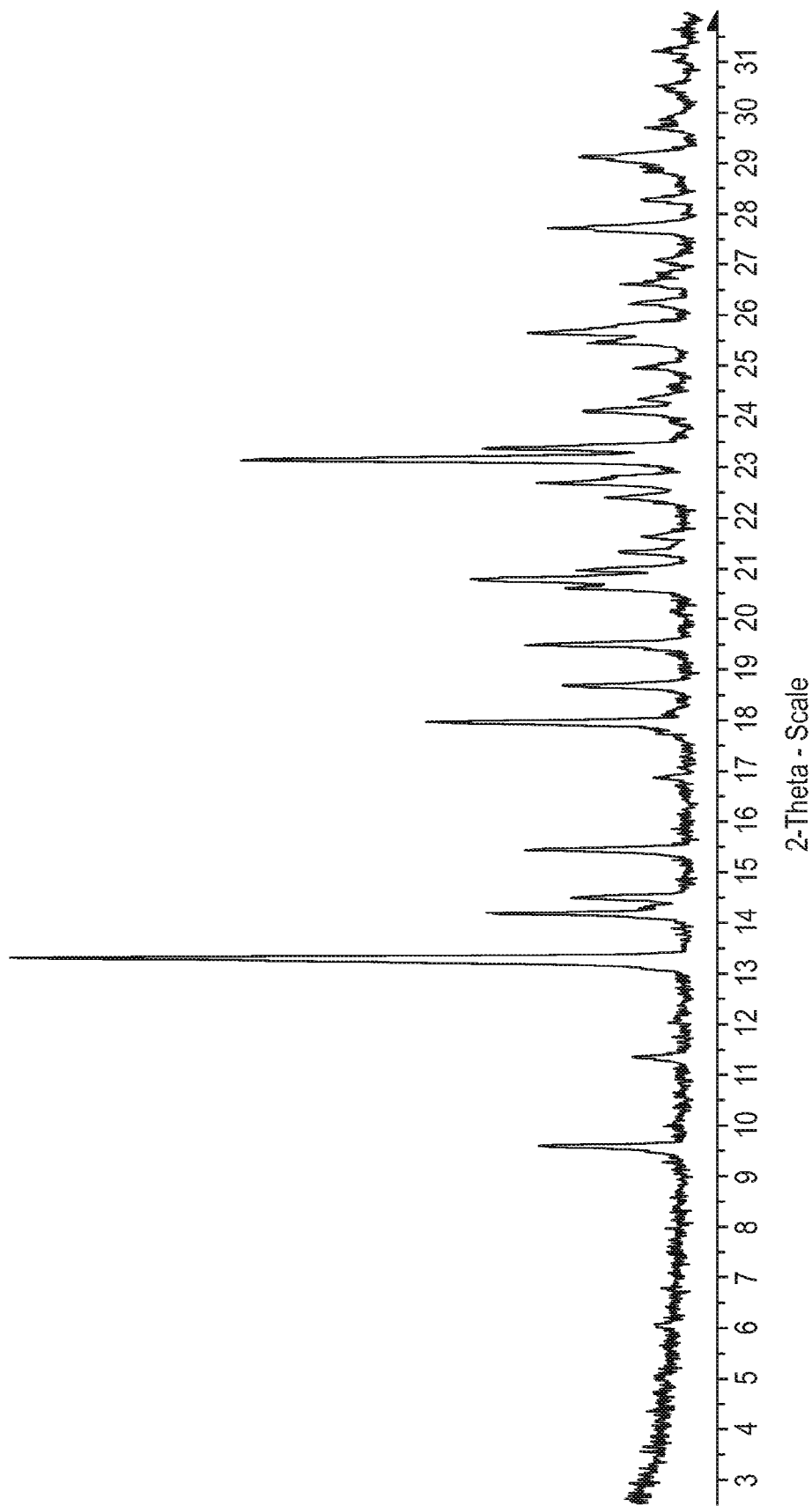
FIG. 17 X-ray powder diffraction pattern of Form 14 of the compound of Formula A (Example 14A).

An XRPD diffractogram (Method D) of Form 14 is shown in FIG. 17.

Peak position table:

| No. | Pos. [°2θ] | Rel. Int. [%] |
|---|---|---|
| 1 | 6 | 8.4 |
| 2 | 9.6 | 25.1 |
| 3 | 11.3 | 11.6 |
| 4 | 13.3 | 100 |
| 5 | 14.2 | 31.5 |
| 6 | 14.5 | 20.4 |
| 7 | 15.4 | 27.1 |
| 8 | 16.9 | 8.8 |
| 9 | 18 | 41.1 |
| 10 | 18.7 | 21.7 |
| 11 | 19.5 | 27.1 |
| 12 | 20.6 | 20.6 |
| 13 | 20.8 | 34.7 |
| 14 | 21 | 19.8 |
| 15 | 21.3 | 13.8 |
| 16 | 21.6 | 10.6 |
| 17 | 22.4 | 15.7 |
| 18 | 22.7 | 25.4 |
| 19 | 23.2 | 67.2 |
| 20 | 23.4 | 32.3 |
| 21 | 24.1 | 18.9 |
| 22 | 24.4 | 11 |
| 23 | 25 | 11.3 |
| 24 | 25.5 | 17.2 |
| 25 | 25.7 | 24.7 |
| 26 | 26.3 | 11.8 |
| 27 | 26.6 | 13.6 |
| 28 | 27.1 | 8.6 |
| 29 | 27.7 | 23.7 |
| 30 | 28.3 | 10.6 |
| 31 | 29.1 | 19.4 |
| 32 | 29.7 | 10 |
| 33 | 29.9 | 8 |
| 34 | 30.5 | 7.6 |
| 35 | 31.3 | 9 |

Example 15—Form 15 of 1-({4-[(5-fluoro-2-oxopyridin-1-yl)methyl]Phenyl}methyl)-N-[(3-fluoro-4-methoxypyridin-2-yl)methyl]-3-(methoxymethyl)pyrazole-4-carboxamide hydrochloride 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide (2.002 g) was suspended and stirred in acetonitrile (20 ml) at up to 70° C. for approximately 5 hours. To the suspension was added 1.1 equivalents of 5.8 M hydrochloric acid in acetonitrile (prepared by diluting 37% HCl with acetonitrile). The resulting solution was stirred for 15 minutes, then allowed to cool to rt. The resulting suspension was temperature cycled, in cycles of 4 hrs, in an incubator between rt and 40° C. for 23 hrs. The suspension was filtered, washed with acetonitrile and dried under vacuum to afford Form 15 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide hydrochloride.

An XRPD diffractogram (Method C) of Form 15 is shown in FIG. 18.

Peak position table:

| No. | Pos. [°2θ] | Rel. Int. [%] |
|---|---|---|
| 1 | 9.2 | 10.0 |
| 2 | 10.0 | 100.0 |
| 3 | 10.7 | 18.2 |
| 4 | 12.4 | 45.8 |
| 5 | 13.9 | 39.2 |
| 6 | 14.8 | 6.1 |
| 7 | 15.8 | 10.7 |
| 8 | 16.6 | 17.5 |
| 9 | 17.4 | 7.0 |
| 10 | 18.4 | 12.2 |
| 11 | 18.6 | 11.0 |

-continued

Peak position table:

| No. | Pos. [°2θ] | Rel. Int. [%] |
|---|---|---|
| 12 | 18.9 | 12.0 |
| 13 | 20.0 | 38.3 |
| 14 | 20.5 | 5.6 |
| 15 | 21.3 | 14.1 |
| 16 | 21.9 | 15.2 |
| 17 | 22.1 | 12.0 |
| 18 | 22.7 | 12.4 |
| 19 | 24.2 | 10.5 |
| 20 | 24.8 | 59.2 |
| 21 | 25.2 | 14.3 |
| 22 | 25.8 | 13.7 |
| 23 | 27.0 | 15.1 |
| 24 | 27.2 | 19.7 |
| 25 | 27.8 | 11.7 |
| 26 | 28.3 | 6.2 |
| 27 | 28.5 | 7.0 |
| 28 | 28.9 | 7.5 |
| 29 | 29.1 | 7.5 |
| 30 | 29.4 | 7.3 |
| 31 | 29.5 | 8.3 |
| 32 | 30.4 | 9.4 |
| 33 | 31.8 | 10.2 |

Thermogravimetric Analysis and Differential Scanning Calorimetry

The TGA and DSC data for Form 15 are shown in FIG. 19.

Example 15A—Form 15 of 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide hydrochloride 1-({4-[(5-fluoro-2-oxopyridin-1-yl)methyl]phenyl}methyl)-N-[(3-fluoro-4-methoxypyridin-2-yl)methyl]-3-(methoxymethyl)pyrazole-4-carboxamide (2.5 g) was dissolved in acetonitrile (50 mL) at 65° C. while being stirred. To the solution, 37% HCl in water (443 μl) was added. The mixture was maintained at 65° C. for 1 hrs. The sample was cooled over 16 hrs to 10° C. in a linear cooling rate. The material was dried under vacuum at rt for 16 hrs.

Figure 20:
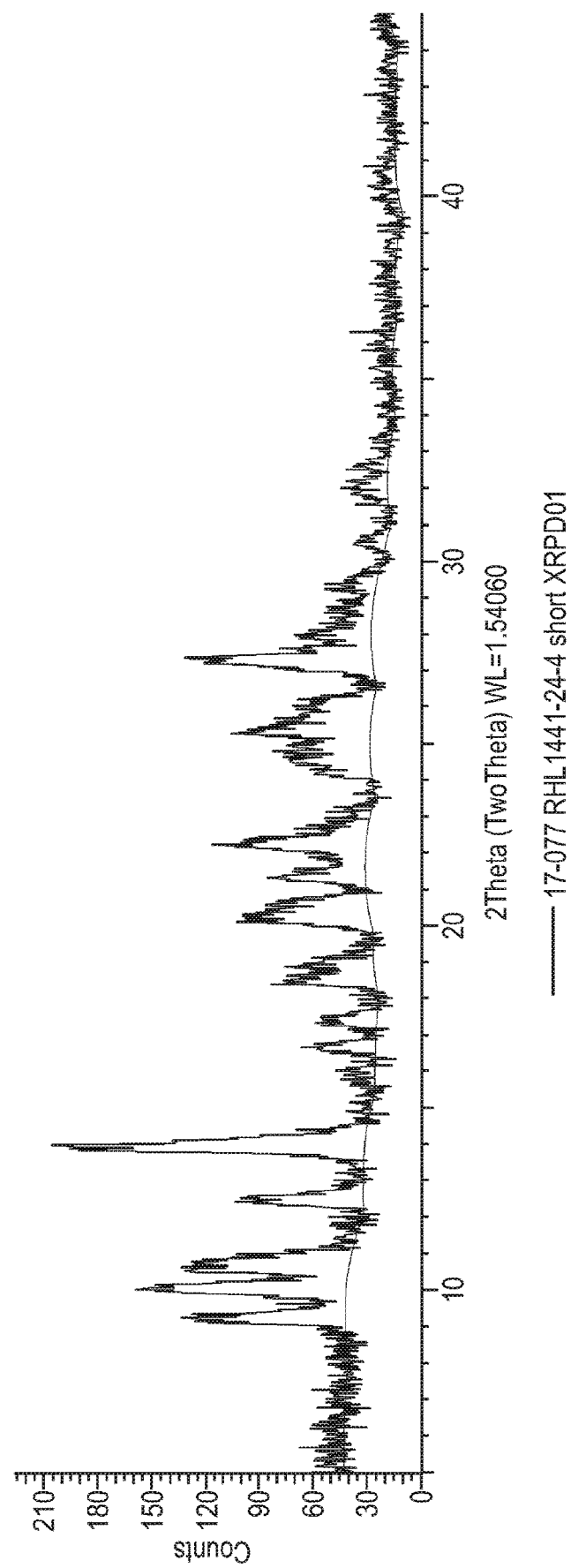
FIG. 20: X-ray powder diffraction pattern of Form 15 of the hydrochloride salt of the compound of Formula A (Example 15A).

An XRPD diffractogram (Method B) of Form 15 is shown in FIG. 20.

Biological Methods

The ability of the compound of formula A to inhibit plasma kallikrein may be determined using the following biological assays. Data for a reference compound, Example 41 of WO2016/083820 (N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide) are also provided for comparative purposes.

Determination of the $IC_{50}$ for Plasma Kallikrein Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human plasma kallikrein (Protogen) was incubated at 25° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

Data acquired from this assay are shown in Table 1.

Compounds were further screened for inhibitory activity against the related enzyme KLK1. The ability of the compounds to inhibit KLK1 may be determined using the following biological assay:

Determination of the $IC_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human KLK1 (Callbiochem) was incubated at 25° C. with the fluorogenic substrate H-DVal-Leu-Arg-AFC and various concentrations of the test compound. Residual enzyme activity (initial rate of reaction) was determined by measuring the change in optical absorbance at 410 nm and the $IC_{50}$ value for the test compound was determined.

Data acquired from this assay are shown in Table 1.

Compounds were also screened for inhibitory activity against the related enzyme FXIa. The ability of the compounds to inhibit FXIa may be determined using the following biological assay:

Determination of the % Inhibition for FXIa

FXIa inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human FXIa (Enzyme Research Laboratories) was incubated at 25° C. with the fluorogenic substrate Z-Gly-Pro-Arg-AFC and 40 μM of the test compound (or alternatively at various concentrations of the test compound in order to determine $IC_{50}$). Residual enzyme activity (initial rate of reaction) was determined by measuring the change in optical absorbance at 410 nm and the $IC_{50}$ value for the test compound was determined.

Data acquired from this assay are shown in Table 1.

Compounds were also screened for inhibitory activity against the related enzyme FXIIa. The ability of the compounds to inhibit FXIIa may be determined using the following biological assay:

Determination of the $IC_{50}$ for FXIIa

Factor XIIa inhibitory activity in vitro was determined using standard published methods (see e.g. Shori et al., Biochem. Pharmacol., 1992, 43, 1209; Baeriswyl et al., ACS Chem. Biol., 2015, 10 (8) 1861; Bouckaert et al., European Journal of Medicinal Chemistry 110 (2016) 181). Human Factor XIIa (Enzyme Research Laboratories) was incubated at 25° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

Data acquired from this assay are shown in Table 1.

TABLE 1

| Compound | $IC_{50}$ (human PKal) nM | $IC_{50}$ (human KLK1) nM | $IC_{50}$ (human FXIa) nM | % Inhibition @ 40 µM (human FXIa) | $IC_{50}$ (human FXIIa) nM |
|---|---|---|---|---|---|
| Example 41 of WO2016/083820 | 3.3 | >40,000 | >40,000 | 0 | >40,000 |
| Compound of Formula A | 6.7 | >40,000 | >40,000 | 7 | >40,000 |

Determination of Enzyme Selectivity

Human serine protease enzymes plasmin, thrombin and trypsin were assayed for enzymatic activity using an appropriate fluorogenic substrate. Protease activity was measured by monitoring the accumulation of liberated fluorescence from the substrate over 5 minutes. The linear rate of fluorescence increase per minute was expressed as percentage (%) activity. The Km for the cleavage of each substrate was determined by standard transformation of the Michaelis-Menten equation. The compound inhibitor assays were performed at substrate Km concentration and activities were calculated as the concentration of inhibitor giving 50% inhibition ($IC_{50}$) of the uninhibited enzyme activity (100%).

Data acquired from these assays are shown in Table 2 below:

TABLE 2

Selectivity data

| | $IC_{50}$ (nM) | | |
|---|---|---|---|
| Compound | Plasmin | Thrombin | Trypsin |
| Compound of Formula A | >40000 | >40000 | >40000 |

Solubility Data

Solubility was determined in water and 0.1N HCl (aq). Test compounds were incubated at 1 mg/mL for 24 hrs at 37° C. on a shaking platform (500 rpm). Samples were taken at 1, 4 and 24 hrs and centrifuged at 15,000 g for 10 min. Test compound concentration in the supernatant was determined by LCMS against a standard curve. The results are shown in Table 3 below.

TABLE 3

Solubility data

| Compound | 0.1N HCl (aq) (mg/mL) | Water (mg/mL) |
|---|---|---|
| Compound of Formula A | 0.94 | 0.29 |

In Vitro ADME Data

In vitro permeability was determined using the Caco-2 model for oral absorption. The methodology was adapted from standard published methods (Wang Z, Hop C. E., Leung K. H. and Pang J. (2000) J Mass Spectrom 35(1); 71-76). The Caco-2 monolayers were established in a Biocoat™ HTS fibrillar collagen 24 well multiwell insert system (1.0 µm, PET membrane, Corning 354803) in which 200,000 cells were seeded into each insert and maintained over 3 days before being utilised in the permeability assay. For the assay, 50 µM test compound is added to the apical side of the inserts and incubated for 1 hour at 37° C. on a shaking platform (120 rpm). Apical to basolateral transport was determined by measuring the test article in both compartments by LCMS following the 1 hour incubation. The integrity of the Caco-2 monolayers was confirmed by two methods, (i) comparison of pre- and post-experiment transepithelial electrical resistance (TEER) and, (ii) assessment of Lucifer Yellow flux. The results are shown in Table 4 below.

The metabolic stability was determined using standard published methods (Obach RS (1999) Drug Metab Dispos 27(11); 1350-135). Human liver microsomes (1 mg/mL; Corning) were incubated with 5 µM test compound at 37° C. on a shaking platform (150 rpm). Samples were taken at 0 and 60 min. The percentage test compound remaining at 60 minutes was determined by ratio of LCMS peak areas. The results are shown in Table 4 below.

TABLE 4

In vitro ADME data

| Compound | % remaining at 60 minutes | Caco-2 (Papp × $10^{-6}$ cm/s) |
|---|---|---|
| Example 41 of WO2016/083820 | Not determined | 9 |
| Compound of Formula A | 25% | 24 |

Pharmacokinetics

Pharmacokinetic studies of the compounds in Table 5 were performed to assess the pharmacokinetics following a single oral dose in male Sprague-Dawley rats. Two rats were given a single po dose of 5 mL/kg of a nominal 2 mg/mL (10 mg/kg) composition of test compound in vehicle. Following dosing, blood samples were collected over a period of 24 hrs. Sample times were 5, 15 and 30 minutes then 1, 2, 4, 6, 8 and 12 hrs. Following collection, blood samples were centrifuged and the plasma fraction analysed for concentration of test compound by LCMS. Oral exposure data acquired from these studies are shown in Table 5 below:

TABLE 5

Oral exposure data

| Compound | Vehicle | Dose po (mg/kg) | Cmax (ng/mL) | Tmax (min) |
|---|---|---|---|---|
| Example 41 of WO2016/083820 | 10% DMSO/10% cremophor/80% SWFI | 10.5 | 1534 | 180 |
| Compound of Formula A | 10% DMSO/10% cremophor/80% SWFI | 4.3 | 756 | 38 |

The invention claimed is:

1. A solid form of the hydrochloride salt of the compound of Formula A,

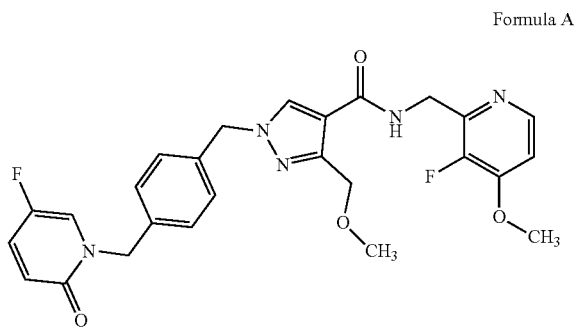 [SMILES: COCc1nn(Cc2ccc(Cn3cc(F)ccc3=O)cc2)cc1C(=O)NCc1nccc(OC)c1F]

Formula A having an X-ray powder diffraction pattern substantially the same as that shown in FIG. 6.

2. A pharmaceutical composition comprising a solid form of claim 1 and a pharmaceutically acceptable adjuvant, diluent and/or carrier.

3. A process for preparing the solid form of the hydrochloride salt of the compound of Formula A of claim 1, comprising crystallising said solid form from a solution of the hydrochloride salt of the compound of Formula A in a solvent or a mixture of solvents.

4. The process of claim 3, wherein the solvent or mixture of solvents comprises methanol, ethanol, isopropanol, acetone, methyl ethyl ketone, tetrahydrofuran or acetonitrile.

5. The process of claim 4, therein the solvent or mixture of solvents comprises a solvent methanol, ethanol, isopropanol or acetonitrile.

6. The solid form of claim 1, which exhibits at least the following characteristic X-ray powder diffraction peaks (Cu Kα radiation, expressed in degrees 2θ) at approximately 10.4, 15.6, 16.7, and 20.8.

7. The process of claim 3, wherein the solvent is THF, acetone or acetonitrile.

8. The process of claim 6, wherein the solvent is THF.

9. The process of claim 3, wherein the crystallising comprises temperature cycling.

10. The process of claim 8, wherein the temperature cycling comprises cycling the temperature of the solution between about 30 to 50° C. and ambient temperature.

11. The process of claim 9, wherein the temperature cycling comprises cycling the temperature of the solution between about 40° C. and ambient temperature.

12. The process of claim 10, wherein the temperature cycling is performed for about 18 to about 24 hours.

13. The process of claim 3, further comprising adding hydrochloric acid to a solution or suspension of the compound of Formula A in a solvent or mixture of solvents.

14. A process for preparing a pharmaceutical composition, comprising combining a solid form of claim 1 and one or more of a pharmaceutically acceptable carrier, diluent, or excipient.

15. A solid form of the hydrochloride salt of the compound of Formula A,

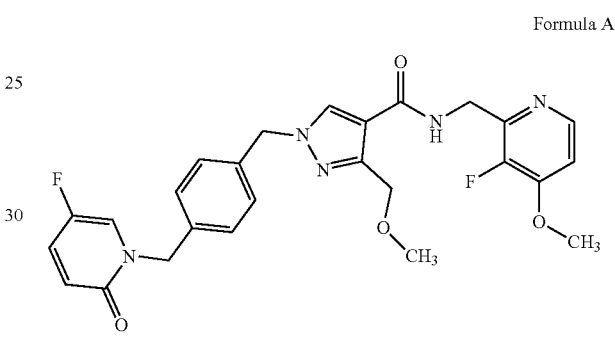

Formula A which exhibits at least the following characteristic X-ray powder diffraction peaks (Cu Kα radiation, expressed in degrees 2θ) at approximately 10.4, 15.6, 16.7, and 20.8.

* * * * *